US012745743B2

(12) United States Patent
Robles et al.

(10) Patent No.: US 12,745,743 B2
(45) Date of Patent: *Sep. 29, 2026

(54) MUSHROOM VARIETIES

(71) Applicant: Amycel, LLC, Watsonville, CA (US)

(72) Inventors: Christopher W. Robles, Watsonville, CA (US); Maykoe R. Abaunza, Memphis, TN (US)

(73) Assignee: Amycel, LLC, Watsonville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/305,675

(22) Filed: Aug. 20, 2025

(65) Prior Publication Data

US 2026/0053108 A1 Feb. 26, 2026

Related U.S. Application Data

(60) Provisional application No. 63/733,289, filed on Dec. 12, 2024, provisional application No. 63/685,196, filed on Aug. 20, 2024.

(51) Int. Cl.
*A01H 15/00* (2006.01)

(52) U.S. Cl.
CPC .................................... *A01H 15/00* (2013.01)

(58) Field of Classification Search
None
See application file for complete search history.

(56) References Cited

U.S. PATENT DOCUMENTS

| | | | | |
|---|---|---|---|---|
| 4,996,390 | A | 2/1991 | Dahlberg | |
| 5,304,721 | A | 4/1994 | Kerrigan et al. | |
| 7,608,760 | B2 | 10/2009 | Robles et al. | |
| 9,017,988 | B1 | 4/2015 | Kerrigan et al. | |
| 2010/0212042 | A1 | 8/2010 | Robles et al. | |
| 2015/0216127 | A1 | 8/2015 | Kerrigan et al. | |
| 2015/0216128 | A1 | 8/2015 | Kerrigan et al. | |
| 2020/0084993 | A1 | 3/2020 | Kerrigan et al. | |
| 2023/0265379 | A1* | 8/2023 | Amini | C12N 1/145 435/254.1 |
| 2026/0060156 | P1 | 2/2026 | Robles et al. | |
| 2026/0060157 | P1 | 2/2026 | Robles et al. | |
| 2026/0060158 | P1 | 2/2026 | Robles et al. | |

FOREIGN PATENT DOCUMENTS

| | | | |
|---|---|---|---|
| WO | WO-2015127195 | A1 | 8/2015 |
| WO | WO-2016116632 | A1 | 7/2016 |
| WO | WO-2018013603 | A1 | 1/2018 |

OTHER PUBLICATIONS

U.S. Appl. No. 19/305,681, filed Aug. 20, 2025, Robles, Christopher W.*

Sonnenberg et al., 2017, Appl Mircobiol Biotechnol, 101:1819-1829.*

Castle et al., (1987). "Restriction fragment length polymorphisms in the mushrooms. *Agaricus brunnescens* and *Agaricus bitorquis*," Appl Env Microbiol, 53:816-822.

Castle et al., (1988). "Crosses among Homokaryons from Commercial and Wild-Collected Strains of the Mushroom *Agaricus brunnescens* (=*A. bisporus*)," Appl. Environ. Microbiol., 54:1643-1648.

Hammond et al., (1976). "Carbohydrate metabolism in Agaricus bisporus (Lange) Sing: changes in soluble carbohydrates during growth of mycelium and sporophore," Microbiology, 93(2):309-320.

Herbraud et al., (1988). "Protoplast Production and Regeneration from Mycorrhizal Fungi and Their use for Isolation and Mutants," Can. J, Microbiol, 34: 157-161.

Invitation to pay additional fees received for International Patent Application No. PCT/US2025/042785 mailed on Nov. 21, 2025, 4 pages.

Kerrigan et al., (1993). "Meiotic Behavior and Linkage Relationships in the Secondarily Homothallic Fungus *Agaricus bisporus*," Genetics, 133:225-236.

Khush et al., (1992). "DNA Amplification Polymorphisms of the cultivated mushroom *Agaricus bisporus*," Appl. Env Micro biol, 59: 2971-2977.

Loftus et al., (1988). "DNA Polymorphisms in Commercial and Wild Strains of the Cultivated Mushroom, *Agaricus bisporus*," Theor. Appl. Genet., 76:712-718.

Mueller et al., (1999). "AFLP genotyping and fingerprinting," Trends Ecol Evol, 14:389-394.

Paran et al., (1993). "Development of reliable PCR-based markers linked to downy mildew resistance genes in lettuce," Theor. Appl. Genet., 85:985-993.

Roerink, (2023). "Mushroom Council's New 10-Year Trends Report Reveals Shifting, Growing Consumer Purchasing Patterns," available online at <https://www.mushroomcouncil.com/press-releases/seizing-the-mushroom-movement/>, 4 pages.

Sonnenberg et al., (1988). "An Efficient Protoplasting/Regeneration System for Agaricus bisporus and Agaricus bitorquis," Curr. Microbiolo., 17:285-291.

Wakui, (2013) "[Analysis of single nucleotide polymorphisms (SNPs)]," Rinsho Byori., 61(11):1008-1017. English abstract.

(Continued)

*Primary Examiner* — Jason Deveau Rosen

(74) *Attorney, Agent, or Firm* — Morrison & Foerster LLP

(57) ABSTRACT

New and unique brown varieties of the mushroom *Agaricus bisporus* Imbach were produced by crossing the progeny of brown mushrooms and off-white hybrid mushrooms to bridging cross strains. The resultant hybrids, named 'RO10425', 'RO14176', and 'RO12756', exhibit distinct and stable characteristics. Hybrid 'RO10425' exhibits a lighter cap color, thicker cap flesh, and rounder cap, especially when compared to available brown mushroom varieties. 'RO10425' also exhibits fast mushroom development and high yield. Hybrid 'RO14176' exhibits a light cap color, thicker cap flesh, rounder cap, faster mushroom development, and higher yield, especially when compared to available brown mushroom varieties. Hybrid 'RO12756' exhibits a light cap color, thicker cap flesh, rounder cap, faster mushroom development, and high yield, especially when compared to available brown mushroom varieties.

6 Claims, 10 Drawing Sheets
(10 of 10 Drawing Sheet(s) Filed in Color)

(56) References Cited

OTHER PUBLICATIONS

Unpublished U.S. Appl. No. 19/305,679, filed Aug. 20, 2025, titled "Mushroom Variety 'RO10425'," (Copy not submitted herewith pursuant to the waiver of 37 C.F.R. § 1.98(a)(2)(iii)).
Unpublished U.S. Appl. No. 19/305,681, filed Aug. 20, 2025, titled "Mushroom Variety 'RO14176'," (Copy not submitted herewith pursuant to the waiver of 37 C.F.R. § 1.98(a)(2)(iii)).
Unpublished U.S. Appl. No. 19/305,683, filed Aug. 20, 2025, titled "Mushroom Variety 'RO12756'," (Copy not submitted herewith pursuant to the waiver of 37 C.F.R. § 1.98(a)(2)(iii)).
International Search Report and Written Opinion received for International Patent Application No. PCT/US2025/042785 mailed on Jan. 21, 2026, 17 pages.

* cited by examiner

'RO14176'

'RO14176'

'RO10425'

‘RO10425’

MUSHROOM VARIETIES

CROSS-REFERENCE TO RELATED APPLICATIONS

This application claims the benefit of U.S. Provisional Application No. 63/685,196, filed Aug. 20, 2024, and U.S. Provisional Application No. 63/733,289, filed Dec. 12, 2024, which are hereby incorporated by reference in their entirety.

FIELD

The present disclosure relates to the field of agricultural mycology. More specifically, the disclosure relates to novel mushroom varieties with desirable characteristics, along with the methods of breeding said mushroom varieties.

Latin Name

Genus and species: The mushroom cultivars of this disclosure are identified as *Agaricus bisporus* Imbach.

Varietal Denomination

Variety denomination: The variety denominations are 'RO10425', 'RO14176', and 'RO12756'.

BACKGROUND OF THE INVENTION

The cultivated white button variety of *Agaricus bisporus*, known as *A. bisporus* (Lange) Imbach (syn. *A. brunnescens* Peck), is the predominant mushroom species in cultivation in the world today. After many years in which commercial mushroom sales in the United States were restricted primarily to white-capped *A. bisporus* mushrooms, there has been a recent trend toward increased sales of brown-capped *A. bisporus* mushrooms of various types and other so-called exotic strains (species other than *A. bisporus*). Improved agronomic characteristics can be introduced into the hybrid strains that can influence producer profitability. For instance, strains may have different ancestry, which will be reflected directly by the genotype and indirectly, in some cases, by the phenotypical characteristics. Generally speaking, strains may be differentiated on the basis of traits associated with the hybrid strains, such as, but not limited to, cap shape, surface texture, flesh thickness, color, shelf life, basidial spore number, sporelessness, resistance to infection by, symptoms of, or transmission of bacterial, viral or fungal diseases, amongst many other traits, to give some examples Many of these traits directly contribute to factors that influence productivity, revenue capture, reduced costs, crop performance, and consumer and market demand.

In the endeavor to produce new mushroom varieties possessing desirable and improved characteristics, a preferred method is the crossing of homokaryons, 'homokaryons' being a multinucleate haploid fungal culture possessing a single line (somatic lineage) that is capable of undergoing plasmogamy with one or more other homokaryons. Each genetically different homokaryon is representative of a parent line in a resultant heterokaryon. The degree of success of each strain and the profitability of producers can be improved by the appropriate selection of the parental lines. Additionally, improved visual appeal and improved shelf-life, amongst many other characteristics, can also contribute to increased sales for mushroom growers in the world today. Thus, there are many characteristics by which a novel strain might be judged as superior in a particular production facility or a sales market, regionally or globally.

It is also well understood that an industry relying extensively only on a single genetic lineage is at increased risk of unpredictable, catastrophic crop failure on a worldwide scale due to the spread of diseases. To alleviate this type of problem, development and cultivation of new hybrid strains with independent lineages will help to act as a disease break. Further, it is highly desirable to simultaneously provide both genetic diversification and commercially acceptable improved crop characteristics. Thus, the need continues to exist for new brown hybrid strains of *Agaricus bisporus* with improved and preferred characteristics.

BRIEF SUMMARY OF THE INVENTION

It is an object of the disclosure to provide brown varieties of *Agaricus bisporus* mushroom with improved commercial characteristics relative to existing brown commercial mushrooms. Strains of the new brown varieties, as well as qualities of these new varieties, are described herein.

The following traits have been repeatedly observed and are determined to be the unique characteristics of the novel brown *Agaricus bisporus* mushroom strains. Specifically, it is an object of the disclosure to provide mushrooms that have one or more (most preferably all) of these following characteristics (relative to brown *Agaricus bisporus* now being marketed).

These characteristics in combination distinguish 'RO12756' as a new and distinct brown variety cultivar:

1. Faster or as fast timing to reach pinset, first break, and second break as marketed brown varieties.
2. High yield, especially during the second and third break.
3. Cap apex flesh thicker than marketed brown varieties.
4. Cap edge flesh thicker than marketed brown varieties.
5. Soft cap firmness.
6. Light brown cap color.
8. Stipes more wide or as wide as marketed brown varieties.
9. Higher or as high tray coverage as marketed brown varieties.
10. Incompatibility with other available brown strains.

There are additionally multiple characteristics that in combination distinguish 'RO14176' as a new and distinct brown variety, including:

1. Faster or as fast timing to reach pinset, first break, and second break as marketed brown varieties.
2. Higher or as high yield in first break, second break, third break, and overall yield as marketed brown varieties.
3. Medium-dark brown cap color.
4. Higher tray coverage than marketed brown varieties.
5. Cap apex flesh thicker than marketed brown varieties.
6. Cap edge flesh thicker than marketed brown varieties.
7. Round cap shape.
8. Cap height taller or as tall as marketed brown varieties.
9. Incompatibility with other available brown strains.
10. Descent from a commercial off-white hybrid *Agaricus bisporus* mushroom variety.
11. Descent from a bridging cross-strain.

There are additionally multiple characteristics that in combination distinguish 'RO10425' as a new and distinct brown variety, including:

1. Faster or similar timing to reach pinset and harvestable maturity.
2. High yield, especially during the second break.
3. Medium-dark brown cap color.
4. Incompatibility with other available brown strains.
5. Descent from a commercial off-white hybrid *Agaricus bisporus* mushroom variety.

6. Descent from a bridging cross strain.
7. Round cap shape.
8. Cap apex flesh thicker than marketed brown varieties.
9. Cap edge flesh thicker than marketed brown varieties.

These and other objects of the disclosure have been accomplished by providing a hybrid *Agaricus bisporus* mushroom strain obtained by crossing a mushroom of wild strain AA-0096 or a progeny thereof with a second *Agaricus bisporus* strain comprising a commercial off-white hybrid strain, wherein the mushroom of the disclosure (1) has (a) at least one genetic characteristic of wild strain AA-0096 not present in the second *Agaricus bisporus* strain, (b) at least one genetic characteristic of the second *Agaricus bisporus* strain not present in wild strain AA-0096, and (c) at least one genetic characteristic of the bridging cross strain and (2) has at least one physical characteristic selected from the group consisting of pinset speed, cap color, cap roundness, cap apex flesh thickness, cap edge flesh thickness, cap texture, tray coverage, incompatibility with other strains, speed of harvestable yield in each break, and overall yield that is statistically better than the corresponding physical characteristic of comparison strains 'BR06' or 'B14528'.

Another feature of the present disclosure includes new brown hybrid mushrooms having improved agronomic traits leading favorably to increased consumer and market demand, productivity, crop performance, and revenue. Of particular interest and novel advantage are the following traits exhibited by 'RO10425':

1. Higher yield at later breaks, which enable growers to achieve higher yield per unit area compared to other commercial brown mushrooms.
2. Faster developmental timing, which enables growers to increase their efficiency by allowing them to pick off mushrooms before the end of the growing cycle. Faster strains might also allow for more crops per year. Traits herein related to developmental timing include Days to Pinset, Days to 1st Break, Days to 2nd Break, and Percent Harvested Speed.
3. Thick-fleshed morphology, which reflects higher quality than other commercial brown mushrooms. This morphology remains more consistent at later breaks for 'RO10425' when compared to other commercial varieties, and this increases visual appeal of sliced product. Pre-sliced button mushrooms have been growing in popularity over the last 10+ years; a 10-year report on mushroom sales trends demonstrated that sliced product has eclipsed whole product fresh mushroom sales, encompassing over 50% of fresh brown mushrooms sold in 2023 in the United States (Roerink, A. (2023, October). Ten-year Trends in Fresh Mushroom Sales. Mushroom Council. Available at www[dot]mushroomcouncil[dot]org/wp-content/uploads/2023/10/Ten-Year-Fresh-Mushroom-Trends[dot]pdf).

A further feature of the present disclosure is novel breeding pedigrees having beneficial characteristics unique to the new hybrid strains differentiating them from other commercial brown strains.

One aspect of the present disclosure provides a hybrid *Agaricus bisporus* mushroom strain selected from the group consisting of 'RO10425', 'RO14176', and 'RO12756', representative culture of which having been deposited under ATCC Nos. PTA-127856, PTA-127855, and PTA-127857 respectively. Also provided is a hybrid mushroom produced by the hybrid mushroom strain. Additionally provided is a mushroom part from the hybrid mushroom. In some embodiments, the mushroom part is a fruiting body, cap, stipe, basidium, spore, mycelium, mixed or unmixed spawn, inoculated substrate, protoplast, gill, cell, or product produced from the mushroom.

Another aspect of the present disclosure provides a method of producing a hybrid mushroom culture of *Agaricus bisporus*, the method comprising the steps of: (a) providing a first homokaryon selected from a wild strain, designated AA-0096, or a progeny thereof, wherein said wild strain AA-0096 is available from ATCC under Accession No. PTA-6903; (b) providing a second homokaryon selected from a commercial off-white hybrid strain, which is compatible with first homokaryon; (c) crossing the first homokaryon with the second homokaryon to form a first culture of intermediate hybrid homokaryons; (d) backcrossing the first culture to the second homokaryon to form a second culture of intermediate hybrid homokaryons; and (e) crossing the second culture to a bridging cross strain to form the hybrid mushroom culture, designated 'RO10425', a representative culture of which having been deposited under ATCC Accession No. PTA-127856. In some embodiments, the bridging cross strain is '4×29', representative sample of '4×29' being available under ATCC Accession No. PTA-6877. In some embodiments, the commercial off-white hybrid strain is derived from a U1 mushroom strain. In some embodiments, the method further includes the steps of producing at least one hybrid mushroom, said steps including: (f) inoculating a mushroom growth medium with the hybrid mushroom culture; (g) maintaining said inoculated growth medium under conditions conducive to mushroom fruiting; and (h) collecting at least one hybrid mushroom from said growth medium.

One aspect of the present disclosure provides a *Agaricus bisporus* mushroom strain designated 'RO10425', representative culture of which having been deposited under ATCC Accession No. PTA-127856. In some embodiments, the commercial off-white hybrid strain is derived from a U1 mushroom strain. In some embodiments, a hybrid mushroom produced by the method of any preceding embodiment or produced by the hybrid mushroom strain of any preceding embodiment has at least one physical characteristic selected from the group consisting of: lighter cap color as exhibited by a higher L* (lighter) value, lower a* (greener) value, and lower b* (bluer) value; higher yield in the second break; rounder cap; and thicker cap flesh as exhibited by thicker cap apex flesh and thicker cap edge flesh when compared to the corresponding physical characteristics of 'BR06', 'BR06' having representative sample accessible under ATCC under Accession No. PTA-6876. In some embodiments, a hybrid mushroom produced by the method of any preceding embodiment or produced by the hybrid mushroom strain of any preceding embodiment has at least one physical characteristic selected from the group consisting of: lighter cap color as exhibited by a higher L* (lighter) value, lower a* (greener) value, and lower b* (bluer) value; higher yield; rounder cap; and thicker cap flesh as exhibited by thicker cap apex flesh and thicker cap edge flesh when compared to the corresponding physical characteristics of 'B14528', 'B14528' having representative sample accessible under NRRL Accession No. 50900. Also provided is a mushroom part from the hybrid mushroom of any preceding embodiment. In some embodiments, the mushroom part is a fruiting body, cap, stipe, basidium, spore, mycelium, mixed or unmixed spawn, inoculated substrate, protoplast, gill, cell, or product produced from the mushroom.

Another aspect of the present disclosure includes a method of producing a hybrid mushroom culture of *Agaricus bisporus*, the method comprising the steps of: (a) providing a first homokaryon selected from a hybrid mushroom strain designated 'RO10425', or a progeny thereof, representative sample of 'RO10425' having been deposited under ATCC under Accession No. PTA-127856; (b) providing a second homokaryon selected from the cross of a bridging cross strain and a commercial off-white hybrid strain, which is compatible with first homokaryon; and (c) crossing the first homokaryon with the second homokaryon to form the hybrid mushroom culture, designated 'RO12756', a culture of which has been deposited under ATCC Accession No. PTA-127857. In some embodiments, the bridging cross strain is '4×29', representative sample of '4×29' being available under ATCC Accession No. PTA-6877. In some embodiments, the commercial off-white hybrid is distinct from the hybrid mushroom strain 'RO10425'. In some embodiments, the commercial off-white hybrid strain is derived from a U1 mushroom strain. In some embodiments, the method further includes the steps of producing at least one hybrid mushroom, said steps including: (d) inoculating a mushroom growth medium with the hybrid mushroom culture; (e) maintaining said inoculated growth medium under conditions conducive to mushroom fruiting; and (f) collecting at least one hybrid mushroom from said growth medium.

Another aspect of the present disclosure provides a hybrid *Agaricus bisporus* mushroom strain designated 'RO12756', representative culture of which having been deposited under ATCC Accession No. PTA-127857. Another aspect provides a hybrid *Agaricus bisporus* mushroom strain, wherein the hybrid strain is a cross of a parental hybrid *Agaricus bisporus* mushroom strain with hybrid mushroom strain designated 'RO10425', wherein the parental hybrid strain is a cross of a bridging cross strain to a commercial off-white hybrid strain, and wherein a representative culture of said strain 'RO10425' is available from ATCC under Accession No. PTA-127856. Still another aspect provides a hybrid *Agaricus bisporus* mushroom strain, wherein the hybrid strain is a cross of a parental hybrid *Agaricus bisporus* mushroom strain with hybrid mushroom strain designated 'RO10425', wherein the parental hybrid strain is derived from a U1 type off-white hybrid, and wherein a representative culture of said strain 'RO10425' is available from ATCC under Accession No. PTA-127856. In some embodiments, the commercial off-white hybrid strain is derived from a U1 mushroom strain. In some embodiments, a hybrid mushroom produced by the method of any preceding embodiment or produced by the hybrid mushroom strain of any preceding embodiment has at least one physical characteristic selected from the group consisting of: light brown cap color as exhibited by a higher L* (lighter) value, lower a* (greener) value, and lower b* (bluer) value; as flat or flatter cap shape; thicker cap flesh as exhibited by thicker cap apex flesh and thicker cap edge flesh; as high or higher tray coverage; softer cap firmness; shorter cap height relative to cap diameter; as thick or thicker cap flesh relative to cap diameter; and as thick or thicker stipes relative to cap diameter when compared to the corresponding physical characteristics of 'B14528', 'B14528' having representative sample accessible under NRRL Accession No. 50900. In some embodiments, a hybrid mushroom produced by the method of any preceding embodiment or produced by the hybrid mushroom strain of any preceding embodiment has at least one physical characteristic selected from the group consisting of faster speed to reach pinset and harvestable maturity; as flat or flatter cap shape; thicker cap flesh as exhibited by thicker cap apex flesh and thicker cap edge flesh; as high or higher tray coverage; as high or higher percent of 2nd break yield harvested by 24 days after casing; as high or higher 3rd break yield by 32 days after casing; higher overall 3rd break yield; higher overall yield across all breaks; light brown cap color exhibited by a higher L* (lighter) value, lower a* (greener) value, and lower b* (bluer) value; softer cap firmness; shorter cap height relative to cap diameter; as thick or thicker cap flesh relative to cap diameter; and as thick or thicker stipes relative to cap diameter when compared to the corresponding physical characteristics of 'BR06', 'BR06' having representative sample accessible under ATCC under Accession No. PTA-6876. Also provided herein is a mushroom or part of a mushroom grown from the hybrid mushroom of any preceding embodiment. In some embodiments, the mushroom part is a fruiting body, cap, stipe, basidium, spore, mycelium, mixed or unmixed spawn, inoculated substrate, protoplast, gill, cell, or product produced from the mushroom.

Also provided herein is the use of a spore, protoplast, homokaryon, or tissue culture of 'RO14176'; a spore, protoplast, homokaryon, or tissue culture of 'RO10425'; or a spore, protoplast, homokaryon, or tissue culture of 'RO12756', said use including isolation of the spore, protoplast, homokaryon, or tissue culture by the method of any preceding embodiment, representative sample of 'RO10425' having been deposited under ATCC Accession No. PTA-127856; representative sample of 'RO14176' having been deposited under ATCC Accession No. PTA-127855; and representative sample of 'RO12756' having been deposited under ATCC Accession No. PTA-127857.

Another aspect discloses a method of producing a heterokaryotic hybrid mushroom culture of *Agaricus bisporus*, the method comprising the steps of: (a) providing a first homokaryon selected from a wild strain, designated AA-0096, or a progeny thereof, wherein said wild strain AA-0096 is available from ATCC under Accession No. PTA-6903; (b) providing a second homokaryon selected from a commercial off-white hybrid strain, which is compatible with first homokaryon; (c) crossing the first homokaryon with the second homokaryon to form a first culture of intermediate hybrid homokaryons; (d) backcrossing the first culture to the second homokaryon to form a second culture of intermediate hybrid homokaryons; (e) crossing the second culture to a bridging cross strain to form a hybrid mushroom culture, designated 'RO10425', a culture of which has been deposited under ATCC Accession No. PTA-127856; (f) allowing the hybrid mushroom culture, designated 'RO10425', to undergo plasmogamy; and (g) selecting a heterokaryotic single spore isolate from the result of the plasmogamy, said heterokaryotic single spore isolate designated 'RO14176', thereby producing the heterokaryotic hybrid mushroom culture. In some embodiments, the bridging cross strain is '4×29', representative sample of '4×29' being available under ATCC Accession No. PTA-6877. In some embodiments, wherein the commercial off-white hybrid strain is derived from a U1 mushroom strain. In some embodiments, the method further includes the steps of producing at least one hybrid mushroom, said steps including: (h) inoculating a mushroom growth medium with the hybrid mushroom culture; (i) maintaining said inoculated growth medium under conditions conducive to mushroom fruiting; and (j) collecting at least one heterokaryotic hybrid mushroom from said growth medium.

Also provided herein, in another aspect, is a hybrid *Agaricus bisporus* mushroom strain designated 'RO14176', a culture of which having been deposited under ATCC Accession No. PTA-127855. In some embodiments, a hybrid mushroom produced by the method of any preceding embodiment or produced by the hybrid mushroom strain of any preceding embodiment has at least one physical characteristic selected from the group consisting of faster timing to reach pinset and harvestable maturity; medium-dark brown cap color as exhibited by a higher L* (lighter) value, lower a* (greener) value, and lower b* (bluer) value; rounder cap shape; higher tray coverage; softer cap firmness; higher yield; and thicker cap flesh as exhibited by thicker cap apex flesh and thicker cap edge flesh when compared to the corresponding physical characteristics of 'BR06', 'BR06' having representative sample accessible under ATCC under Accession No. PTA-6876. In some embodiments, a hybrid mushroom produced by the method of any preceding embodiment or produced by the hybrid mushroom strain of any preceding embodiment has at least one physical characteristic selected from the group consisting of faster timing to reach second break; medium-dark brown cap color as exhibited by a higher L* (lighter) value, lower a* (greener) value, and lower b* (bluer) value; rounder cap shape; higher tray coverage; larger stipe diameter; and thicker cap flesh as exhibited by thicker cap apex flesh and thicker cap edge flesh when compared to the corresponding physical characteristics of 'B14528', 'B14528' having representative sample accessible under NRRL Accession No. 50900.

Also provided herein is a mushroom part from the hybrid mushroom produced by the method of any preceding embodiment or the hybrid mushroom strain of any preceding embodiment. In some embodiments, the mushroom part is a fruiting body, cap, stipe, basidium, spore, mycelium, mixed or unmixed spawn, inoculated substrate, protoplast, gill, cell, or product produced from the mushroom.

Still another aspect of the present disclosure includes a method of producing a hybrid mushroom culture of *Agaricus bisporus*, the method including the steps of: (a) providing a hybrid mushroom strain designated 'RO10425', or a progeny thereof, representative sample of 'RO10425' having been deposited under ATCC Accession No. PTA-127856; (b) producing at least one heterokaryotic single spore isolate (SSI) from the hybrid mushroom strain designated 'RO10425'; (c) selecting, from among the at least one SSI, a desirable single spore isolate; and (d) producing the hybrid mushroom culture from the selected single spore isolate, wherein the hybrid mushroom culture is designated 'RO14176', representative sample of 'RO14176' having been deposited under ATCC Accession No. PTA-127855. In some embodiments, the method further includes the steps of producing at least one hybrid mushroom, said steps including (e) inoculating a mushroom growth medium with the hybrid mushroom culture; (f) maintaining said inoculated growth medium under conditions conducive to mushroom fruiting; and (g) collecting at least one hybrid mushroom from said growth medium. Also provided by the present disclosure is a hybrid mushroom produced by the method of any preceding embodiment or the hybrid mushroom strain of any preceding embodiment. In some embodiments, the mushroom part is a fruiting body, cap, stipe, basidium, spore, mycelium, mixed or unmixed spawn, inoculated substrate, protoplast, gill, cell, or product produced from the mushroom.

In some embodiments of the method of any preceding embodiment, the method further includes providing the hybrid mushroom culture, additional hybrid mushroom culture, or a hybrid mushroom culture produced by the heterokaryotic single spore isolate in mushroom products selected from the group consisting of mycelium, spawn, inoculum, casing inoculum, fresh mushrooms, processed mushrooms, parts of mushrooms, mushroom extracts and fractions, mushroom pieces, and colonized substrates including grain, compost, and friable particulate matter; or further includes providing the hybrid mushroom culture in derived cultures selected from the group consisting of homokaryons, heterokaryons, aneuploids, somatic subcultures, tissue explants cultures, protoplasts, dormant spores, germinating spores, inbred descendants, transgenic cultures, and cultures having a genome incorporating a single locus conversion.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF THE INVENTION

Figure 1:
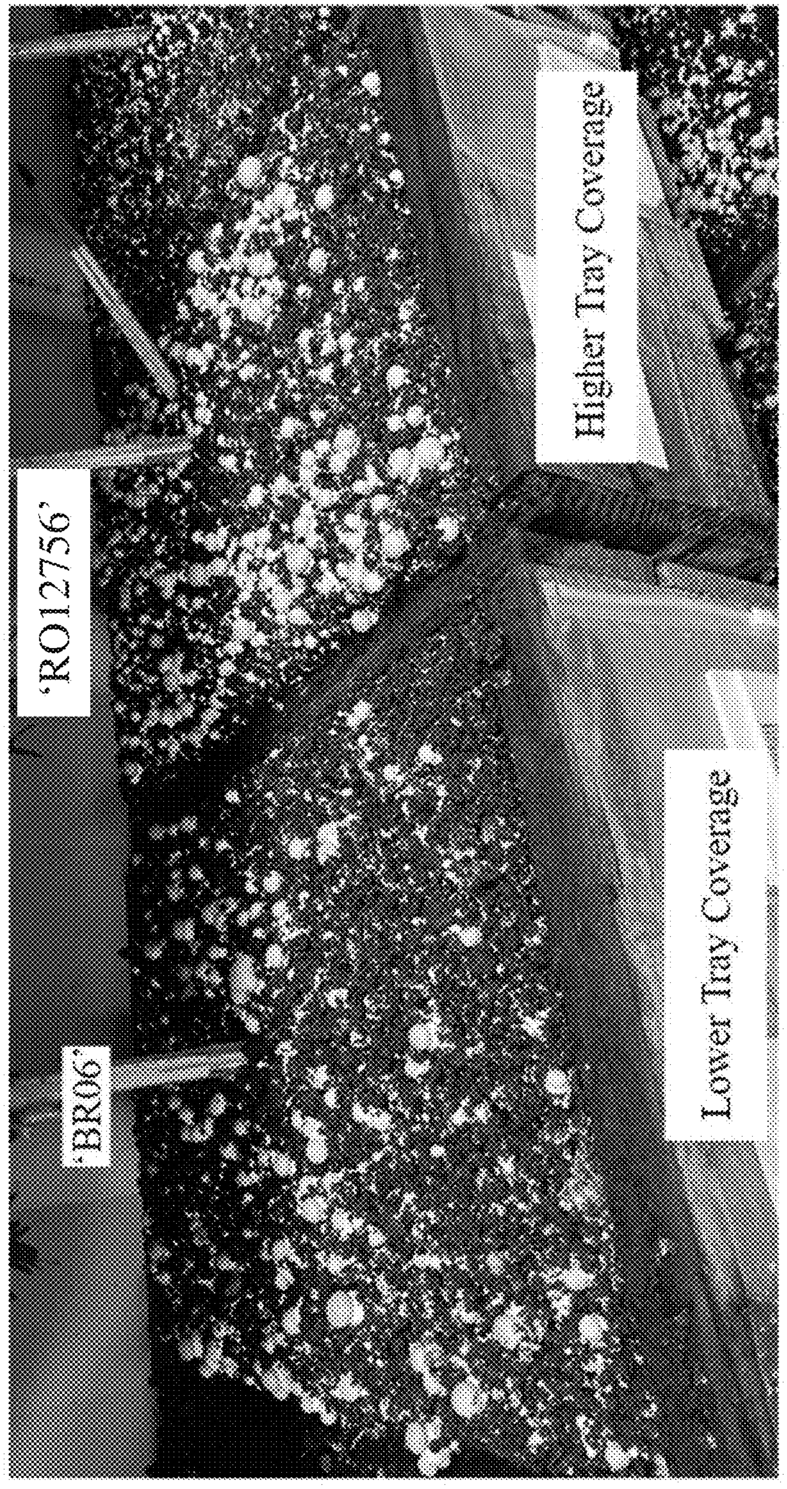
FIG. 1 shows a representative comparison of *Agaricus bisporus* variety 'BR06' (left) and variety 'RO12756' (right) tray coverage at first break. 'BR06' displays lower tray coverage, and 'RO12756' displays higher tray coverage.

It is an object of the disclosure to provide brown varieties of *Agaricus bisporus* mushroom with improved commercial characteristics relative to existing brown commercial mushrooms.

The term “break” as used herein may refer to a flush of fruiting bodies, or a length of time attributed to a period of mushroom growth and harvesting.

*Agaricus bisporus* mushrooms to be marketed as cremini or baby bellas are generally considered to be of harvestable maturity when the caps have reached approximately 3-5 cm in diameter and the veil tissue covering the gills has not yet opened.

The present disclosure of hybrid mushrooms arose from a breeding program that crossed compatible homokaryons collected from wild brown strains, sometimes a bridging cross strain, and a commercial white mushroom strain. One bridging cross strain was produced by crossing compatible homokaryons from a commercial strain of *Agaricus bisporus* and a commercial off-white hybrid mushroom strain. Furthermore, subsequent hybrid strains can be produced by crossing cultures of compatible homokaryons selected from these commercial brown mushroom strains, to induce and/or eliminate certain parental characteristics in the hybrid strains. The specific wild mushroom strain of *A. bisporus* used to provide the desired genetic and phenotypical characteristics is known as AA-0096. The wild strain AA-0096 described in the scientific literature has unique genetic characteristics. Strain AA-0096, also known as BP-1 and ARP-023, is available from the American Type Culture Collection (ATCC) under the accession number 76562 as a non-patent deposit. This strain was re-deposited by the current inventors under the Budapest Treaty governing the deposit of organisms for patent purposes at the American Type Culture Collection, Rockville, MD, USA, under ATCC Accession No. PTA-6903. Hybrid strains obtained by crossing intermediate hybrid strains (or bridging cross strains) of *A. bisporus* and commercial off-white hybrid strains, and successive hybrids obtained by crossing such hybrids with other commercial off-white hybrid strains, can be cultivated to have at least one of the improved genetic and phenotypic characteristics described herein by beneficially using the procedures described herein.

The description of the varied embodiments of this disclosure presented herein, and the availability of the aforementioned strains from their deposits or in the commercial marketplace, enable one skilled in the art to practice the current disclosure using standard methods of mushroom breeding and/or production. In one embodiment of the present disclosure, cloning processes that produce genetically identical crops of mushroom, and crossing processes that produce non-genetically identical progeny, described herein, facilitate the implementation of embodiments of this disclosure and the production of hybrid mushrooms. Further progeny (as well as later crosses derived from these progeny) can be cultivated with desirable characteristics using general breeding techniques.

Breeding Techniques

Methods of the production of mushroom strains, either as direct progeny (clones) of a given strain or as hybrid progeny by crossing with a second strain, are well known. Patent Application No. US 2015/0216127 A1 “Mushroom Line J1Q102-S69 and Methods and Uses Thereof”, Patent Application No. US 2015/0216128 A1 titled “Hybrid Mushroom Strain J1 1500 and Descendants Thereof”, U.S. Pat. No. 9,017,988 B1 entitled “Hybrid Mushroom. Strain B14528 and Descendants Thereof”, U.S. Pat. No. 5,304,721, entitled “Method for the Production of High Proportions of Homokaryons in Breeding Stock of the Mushroom *Agaricus bisporus*”, U.S. Pat. No. 4,996,390 entitled “Novel Interspecific Mushroom Strains”, publications in the scientific literature such as “An Efficient Protoplasting/Regeneration System for *Agaricus bisporus* and *Agaricus bitorquis*.” Curr. Microbiolo., 17:285-291, 1988, by Sonnenberg et al., “Protoplast Production and Regeneration from Mycorrhizal Fungi and Their Use for Isolation and Mutants,” Can. J, Microbiol, 34:157-161, 1988 by Herbraud et al., “DNA Polymorphisms in Commercial and Wild Strains of the Cultivated Mushroom, *Agaricus bisporus*” Theor. Appl. Genet., 76:712-718, 1988 by Loftus et al., “The Genetics and the Breeding of Species *Agaricus*” by Elliott, “Crosses among Homokaryons from Commercial and Wild-Collected Strains of the Mushroom *Agaricus brunnescens* (=*A. bisporus*),” Appl. Environ. Microbiol. 54:1643-1648, 1988, by Castle et al., and books like The Biology and Technology of the Cultivated Mushroom, by Flegg et al., John Wiley and Sons, 1985, pp. 111-139.

Given the availability of mushroom breeding techniques, a person skilled in the art of mushroom production can practice the disclosure and the production of brown hybrid mushrooms and descendants thereof.

In some embodiments, a culture of selected homokaryons collected from a brown commercial strain of *A. bisporus* is first crossed with compatible homokaryons from an off-white commercial white strain to form a first hybrid strain, also referred to as an intermediate or a bridging cross strain. In some embodiments, the off-white commercial mushroom strain is derived from a ‘U1’ mushroom strain, referring to cultivar line ‘Horst U1’ developed in 1980. The homokaryons are usually collected from the natural process of spore formation, but they are also obtained through a technique called protoplasting. Homokaryons or heterokaryons collected from spores are called Single Spore Isolates (SSI or ssi), and those created from protoplasting are called Protoplasts (p). The fundamental difference between these two types of homokaryons is that the SSIs have gone through a meiosis step, and protoplasts have not. SSIs are collected from spore prints, and protoplasts are created from the enzymatic removal of the mycelial fungal cell wall. In some embodiments, SSIs are labeled slow growers (sg). In some embodiments, SSIs are utilized for breeding of hybrid mushrooms. In some embodiments, protoplasts are utilized for breeding of hybrid mushrooms.

In some embodiments, spores from wild mushroom strain designated AA-0096 are used. In some embodiments, spores from at least one commercial off-white hybrid variety are used.

Essentially Derived Varieties

Heterokaryotic spores of initial parental strain retain the great majority of the parental genotype (Kerrigan et. al., Genetics, 133, 225-236, 1993). A group of strains either developed by cloning or by spore culture, or by any other means of 'essential derivation,' from a single progenitor, as opposed to outbreeding, is called a derived lineage group. In general, an Essentially Derived Variety (EDV) is a variety that is predominantly derived from an initial variety or from an EDV of an initial variety and retains the essential characteristics of the initial variety except where the differences that arise are solely from such a derivation. EDVs incorporate elements of (1) relatedness, (2) methods of derivation, (3) and empirical tests. In the art of mushroom strain development, a strain or culture predominantly or entirely derived from a single initial strain or culture, or from the modification of an initial culture using methods including somatic selection, tissue culture selection, selfing, mating among sibling lines, including intramixis (reproduction via single spores and multiple spores and mating of sibling offspring lines), back-mating to the initial variety, or mutagenesis and/or genetic transformation of the initial variety to produce a distinct culture in which the genotype of the resulting culture remains predominantly identical to the initial variety, is an EDV. In one or more embodiments, an Essentially Derived Variety of *A. bisporus* strain or intermediate strain or hybrid strain may be used. It is to be noted that the usage of the term "derived" in many techniques and processes described herein is not in any way congruent with "Essentially Derived Variety".

Novelty of the New Hybrid Strains

In addition to novel pedigree lines, unique genetics help differentiate the brown hybrid mushrooms of this breeding program from existing commercial mushrooms. New or improved phenotypic traits also help distinguish these brown hybrids from other commercial brown or white type mushrooms.

The new hybrid strains described herein possess several traits that give them marketable advantages over other commercial brown strains, including the following:

1. Higher yield at later breaks, which enable growers to achieve higher yield per unit area compared to other commercial brown mushrooms.
2. Faster developmental timing, which enables growers to increase their efficiency by allowing them to pick off mushrooms before the end of the growing cycle. Faster strains might also allow for more cropping cycles per year. Traits herein related to developmental timing include Days to Pinset, Days to 1st Break, Days to 2nd Break, and Percent Harvested Speed.
3. Thick-fleshed morphology, which reflects higher quality than other commercial brown mushrooms. This morphology remains more consistent at later breaks for 'RO10425' when compared to other commercial varieties, and this increases visual appeal of sliced product. Pre-sliced button mushrooms have been growing in popularity over the last 10+ years; a 10-year report on mushroom sales trends demonstrated that sliced product has eclipsed whole product fresh mushroom sales, encompassing over 50% of fresh brown mushrooms sold in 2023 in the United States (Roerink, A. (2023, October). Ten-year Trends in Fresh Mushroom Sales. Mushroom Council. Available at www[dot]mushroom-council[dot]org/wp-content/uploads/2023/10/Ten-Year-Fresh-Mushroom-Trends[dot]pdf).

Genetics of the New Hybrid Strains

Mushrooms within the scope of the present disclosure that are called "clones", can be prepared by any of the known cloning processes (as well as those that may be discovered in the future) from a mushroom of the disclosure. These clones are prepared without a sexual crossing process and have the same genetic and physical characteristics as their parents. A "genetic trait" is any property of the genetic material of a mushroom strain (usually a gene sequence) that can be measured by a conventional analytical technique. Examples of genetic traits include RAPD, RFLP, AFLP, SNPs, or SCAR bands, as they appear on gels using standard analytical techniques. These well-known analytical techniques are described in numerous scientific publications, including the following:

SCAR: Paran, I. and R. W. Michelmore (1993). Development of reliable PCR-based markers linked to downy mildew resistance genes in lettuce. Theor. Appl. Genet. 85: 985-993.

RAPD: Khush, R. S., Becker, E. and M. Wach (1992). DNA Amplification Polymorphisms of the cultivated mushroom *Agaricus bisporus*. Appl. Env Microbiol 59: 2971-2977.

RFLP: Castle, A J., P. A. Horgen and J. B Anderson 1987. Restriction fragment length polymorphisms in the mushrooms. *Agaricus brunnescens* and *Agaricus* bitorquis. Appl Env Microbiol 53: 816-822

AFLP: Mueller U G and Wolfenbarger L L (1999) AFLP genotyping and fingerprinting. Trends Ecol Evol 14: 389-394.

SNP: Wakui M. (2013) [Analysis of single nucleotide polymorphisms (SNPs)]. Rinsho Byori. 2013 November; 61(11):1008-17. Japanese. PMID: 24450106.

Heterokaryotic spore collection and analysis is another valuable resource for genetic analysis, as this allows the examination of spores that are likely very similar to clones described above, due to their unusual meiosis undertaken.

Superiority of the New Hybrid Strains

Following the methods described herein, strains derived herein exhibit improved characteristics over the commercially available brown varieties 'BR06' and/or 'B14528'. These improvements may include thicker cap flesh, faster timing to reach pinset and harvestable maturity, higher tray coverage, a unique brown cap color, softer cap firmness, thicker stipes and cap flesh relative to cap diameter, higher compost colonization levels, faster development of harvestable mushrooms, and higher overall yield.

These improvements are due to the introduction of a wild parent, AA-0096, to commercial off-white hybrid strains and subsequent crosses and selection, as well as the inclusion of both commercial and wild brown mushroom strains. These improvements are in addition to the many traits that have made UI derived off-white hybrids successful commercial mushroom strains. Mushrooms with improved cap color, yield, and percent harvested speed will attract a higher price than conventional brown mushroom strains.

Mushroom Breeding and Hybridization

In mushroom breeding, mycelial (=vegetative) cultures of two compatible progenitors (typically these are haploid homokaryotic strains called homokaryons) must come into physical contact so that one or more fusion zones can occur between the progenitors. Within those fusion zones nuclei from the two progenitors become associated. In *Agaricus bisporus*, a novel, hybrid mycelium ultimately containing two compatible haploid nuclear types (one from each of the two progenitors) plus one mitochondrial type (from either one of the progenitors) emerges. This novel hybrid mycelium can be isolated and propagated to provide the new hybrid culture, which can be further subdivided and propagated for commercial or other purposes.

It should be recognized that the mushrooms of the present disclosure are hybrids (equivalent to crosses), as they are formed by the hybridization of at least two independently derived strains, since they were formed by hybridizing the wild strain AA-0096 with a second, commercialized strain of *A. bisporus* (with the second strain, in some embodiments, being itself a cross between at least two other identified strains of *A. bisporus*). The term 'hybrid mushroom' may be used herein to represent the product of a cross between a wild *A. bisporus* strain and a commercial strain, often including a cross between a brown mushroom strain and an off-white hybrid variety. Differences in terminology (and in the specific techniques used alongside the terminology) are merely indicative of the variety of terminology and techniques used in the mushroom production field.

After parental homokaryotic spores germinated into mycelia, single spore isolates (SSIs) were selected, preferentially those exhibiting slow mycelial growth. The slowly growing mycelia of SSIs usually contain one nuclear type, are thus homokaryotic, and are suitable for crossing, and thus for breeding. Slow growers are denoted as "sg". Some homokaryons were obtained through protoplasting; this technique involves treating the vegetative mycelia of the heterokaryons to damage the fungal cell wall, then selecting colonies of protoclones that are each derived from a single, regenerated protoplast. All crosses were initially cultivated on a small scale, and spores were collected for the parents of the crosses to produce the hybrids described herein.

One useful feature in the breeding programs for these novel mushroom varieties is the use of a bridging cross strain, which is a hybrid variety produced from crossing a commercial brown variety with a commercial white variety. The particular bridging cross strain of note in these breeding programs is known as the 4×29 strain. Strain 4×29 has been previously deposited under the provisions of the Budapest Treaty with the American Type Culture Collection, Rockville, Md., USA, ATCC accession No. PTA-6877 (deposited on Jul. 20, 2005). Strain 4×29 is the product of crossing a commercial brown strain with a commercial white strain. The '29' of this strain is a unique homokaryon collected from an off-white hybrid strain.

The varieties, mushrooms, strains, and cultures disclosed herein are understood to comprise parts of mushrooms, such as the fruiting body, cap, stipe, basidium, spore, mycelium, mixed or unmixed spawn, inoculated substrate, protoplast, gill, cell, or product produced from the mushroom. In some embodiments, the mushroom part from the hybrid mushroom produced by any method disclosed herein is a spore. In some embodiments, the mushroom part produced from a mushroom strain disclosed herein is a spore. In some embodiments, 'RO14176' is a mushroom part produced from the hybrid mushroom of 'RO10425'. In some embodiments, the mushroom part produced from the hybrid mushroom of 'RO10425' is 'RO14176'.

EXAMPLES

Example 1: Characterization of 'RO10425'

The following example describes the characterization of strain 'RO10425' compared to a related variety and commercial varieties.

Methodology

In the descriptions and tables that follow, numerous traits are calculated/measured as follows in Table 1.

Figure 2:
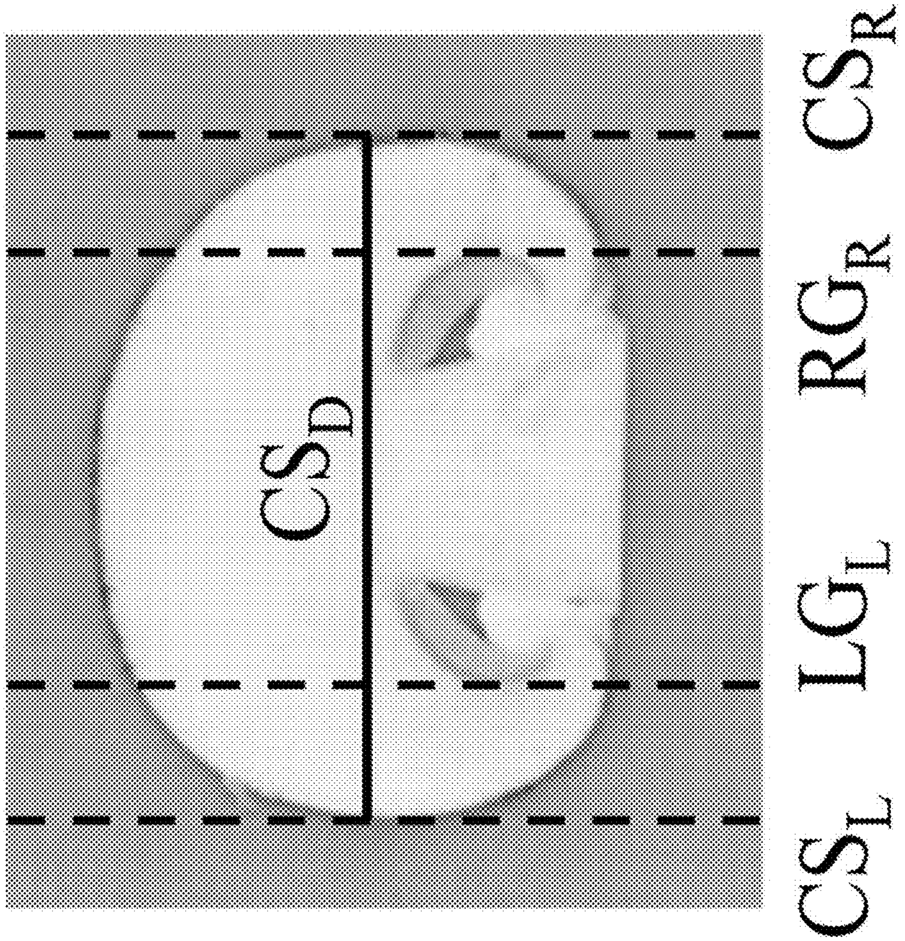
FIG. 2 shows a longitudinal slice of a mushroom of variety 'RO14176' with markings added to illustrate the calculation of Cap Edge Flesh Thickness, where Cap Edge Flesh Thickness is calculated by $((LG_L-CS_L)+(CS_R-RG_R))/CS_D$. $LG_L$=left-most x-coordinate of the left gill, $CS_L$=left-most x-coordinate of the cross-section, $CS_R$=right-most x-coordinate of the cross-section, $RG_R$=right-most x-coordinate of the right gill, and $CS_D$=diameter of the cross-section.
Figure 3:
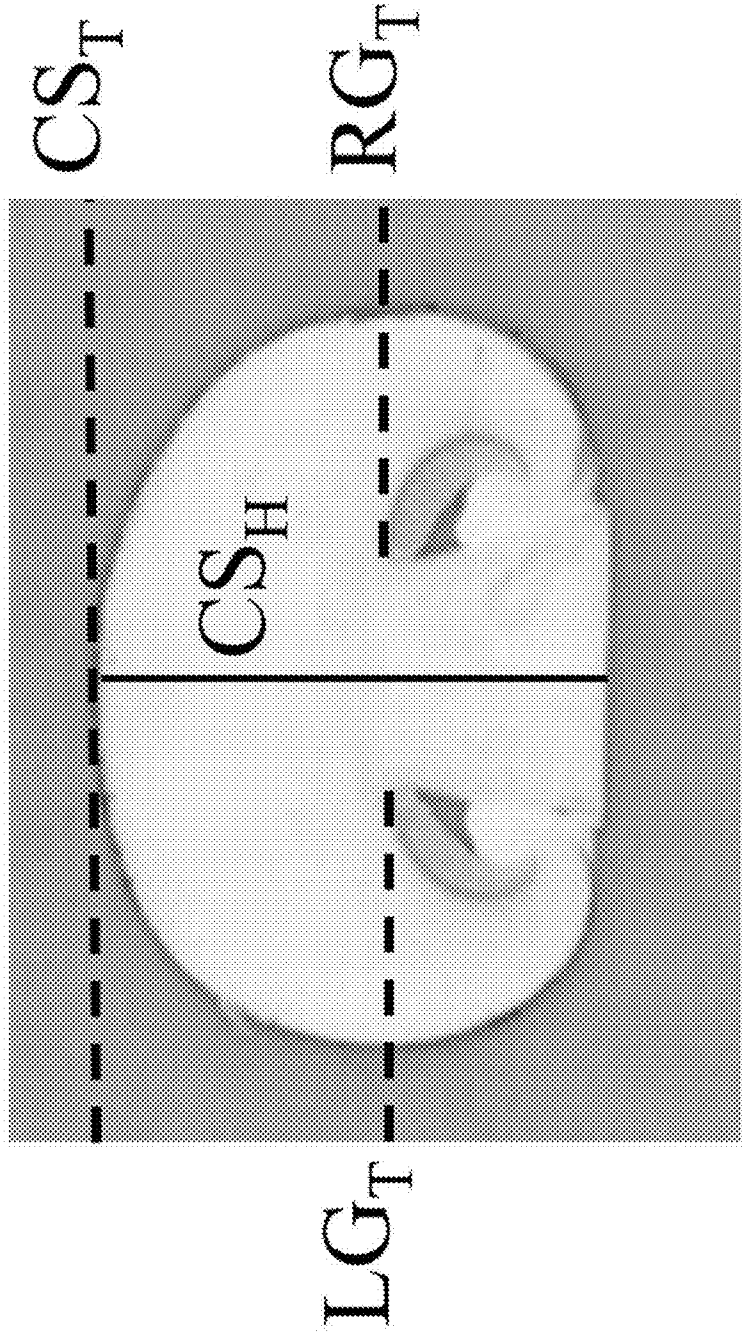
FIG. 3 shows a longitudinal slice of a mushroom of variety 'RO14176' with markings added to illustrate the calculation of Cap Apex Flesh Thickness, where Cap Apex Flesh Thickness is calculated by $(CS_T-((LG_T+RG_T)/2))/CS_H$. $CS_T$=the top-most y-coordinate of the cross-section, $LG_T$=the top-most y-coordinate of the left gill, $RG_T$=the top-most y-coordinate of the right gill, and $CS_H$=the height of the cross-section.

Visual depictions of the measurements used for calculating Cap Apex Flesh Thickness are shown in FIG. 3. Visual depictions of the measurements used for calculating Cap Edge Flesh Thickness are shown in FIG. 2.

Mushrooms were harvested at Stage 3 as described by Hammond & Nichols (Hammond, J. B. W., & Nichols, R. (1976). Carbohydrate metabolism in *Agaricus bisporus* (Lange) Sing.: changes in soluble carbohydrates during growth of mycelium and sporophore. Microbiology, 93(2), 309-320), when cap diameters were approx. 3-5 cm with the veil still intact. To reduce confounding effects introduced by different trials, developmental timing and yield traits were compared only from trials where all strains being compared were present together.

Images of mushroom caps and longitudinal cross-sections were captured using a Canon Rebel SL1 camera (Canon, Inc., Toyko, Japan) in a custom-built photo box with standardized lighting conditions. The camera was calibrated for color consistency using a ColorChecker gray balance card (Calibrite LLC, Wilmington, DE). L*, a* and b* values were captured across the surface of each mushroom cap and cross-section using ImageJ (Schneider, C. A., Rasband, W. S., & Eliceiri, K. W. (2012). NIH Image to ImageJ: 25 years of image analysis. Nature Methods, 9(7), 671-675). Images captured in 2024 and 2025 were used for analysis. Extreme outliers were excluded from the data, defined as those falling 3 times the interquartile range (IQR) above the 75th percentile for that trait or more than 3 times the IQR below the 25th percentile for that trait.

All statistical analyses were carried out in the R programming language (R Core Team, (2013). R: A language and environment for statistical computing. R Foundation for Statistical Computing, Vienna, Austria. www[dot]R-project [dot]org/). Levene's test was performed using the 'car' package (Fox, J., & Weisberg, S. (2018). An R companion to applied regression. SAGE Publications), Shapiro-Wilk tests and Tukey HSD were performed using the 'stats' package (R Core Team (2013)), and standard ANOVAs, Kruskal-Wallis tests and Dunn's tests were performed using the 'rstatix' package (Kassambara, A (2023). rstatix: Pipe-Friendly Framework for Basic Statistical Tests. R package version 0.7.2, rpkgs[dot]datanovia[dot]com/rstatix/).

TABLE 1

| Trait | Tool | Measurement Scale | Timing |
|---|---|---|---|
| Cap Color Darkness | visually assessed | 0 to 5 (from white to dark brown), tray-level measurement | 1st break**, 2nd break** |
| Cap Color a* Value (Green-Red) | image analysis | −128 to +127 (from pure green to pure red), individual mushroom-level measurement | 1st break**, 2nd break** |
| Cap Color b* Value (Blue-Yellow) | image analysis | −128 to +127 (from pure blue to pure yellow), individual mushroom-level measurement | 1st break**, 2nd break** |
| Cap Color L* Value (Dark-Light) | image analysis | 0 to 100 (from pure black to pure white), individual mushroom-level measurement | 1st break**, 2nd break** |
| Cap Diameter | image analysis | millimeters (mm), individual mushroom-level measurement | 1st break**, 2nd break* |

TABLE 1-continued

| Trait | Tool | Measurement Scale | Timing |
|---|---|---|---|
| Cap Firmness | manual squeeze test | 1 to 5 (from very soft to very firm), tray-level measurement | 1st break**, 2nd break** |
| Cap Apex Flesh Thickness | calculated ratio and image analysis | distance from top of gills to top of cap of mushroom, relative to cap height, individual mushroom-level measurement | 1st break**, 2nd break* |
| Cap Edge Flesh Thickness | calculated ratio and image analysis | sum of distances from outer edge of each gill to outer edges of cap of mushroom, relative to cap diameter, individual mushroom-level measurement | 1st break**, 2nd break** |
| Cap Flesh Thickness | hand-measurement | millimeters (mm), distance from top of gill-stipe connection (at center of stipe) to top of cap, individual mushroom-level measurement | 1st break**, 2nd break** |
| Cap Height | image analysis | millimeters (mm), distance from base of cap to top of cap, individual mushroom-level measurement | 1st break**, 2nd break** |
| Cap Roundness (Calculated) | image analysis | Unitless ratio (0-1), calculated as $4 * CS_A/(\pi * CS_D^2)$, where $CS_A$ = area of the cross-section, and $CS_D$ = diameter of the cross-section; assessed with image analysis, individual mushroom-level measurement | 1st break**, 2nd break** |
| Cap Roundness (Visual) | visually assessed | 1 to 5 (from very flat to spherical), tray-level measurement | 1st break**, 2nd break** |
| Compatibility | calculated ratio | pounds per square foot ($lb/ft^2$) and kilograms per square meter ($kg/m^2$), weight of 1st break mushrooms yielded relative to area of tray, tray-level measurement | 1st break** |
| Compost Colonization | visually assessed | 0 to 5 (from no colonization to robust colonization), tray-level measurement | before 1st break (10 days after spawning) |
| Days to 1st Break | visually assessed | number of days elapsed after casing at which at least half of tray is of harvestable maturity for 1st break, tray-level measurement | 1st break** |
| Days to 2nd Break | visually assessed | number of days elapsed after casing at which at least half of tray is of harvestable maturity for 2nd break, tray-level measurement | 2nd break** |
| Days to Pinset | visually assessed | number of days elapsed after casing at which pins first reach 5 mm, tray-level measurement | before 1st break |
| Percent Harvested Speed | calculated ratio | % of yield harvested by a designated date within break, yield at date within break/total yield for break, trial-level measurement | 17 days after casing (1st break), 24 days after casing (2nd break), 32 days after casing (3rd break) |
| Relative Cap Flesh Thickness | calculated ratio | Cap Flesh Thickness Value/Cap Diameter Value, individual mushroom-level measurement | 1st break**, 2nd break** |
| Relative Cap Height | calculated ratio | Cap Height Value/Cap Diameter Value, individual mushroom-level measurement | 1st break**, 2nd break** |
| Relative Stipe Diameter | calculated ratio | Stipe Diameter Value/Cap Diameter Value, individual mushroom-level measurement | 1st break**, 2nd break** |
| Stipe Diameter | hand-measurement | millimeters (mm), stipe diameter at base of cap, individual mushroom-level measurement | 1st break**, 2nd break** |
| Tray Coverage | visually assessed | 0 to 5 (from no coverage to full coverage), tray-level measurement | 1st break**, 2nd break** |
| Yield (Each Break) | weighing | $kg/m^2$, tray-level measurement; or $lb/ft^2$, tray-level measurement | Assessed cumulatively throughout 1st, 2nd, and 3rd breaks |
| Yield (Total) | weighing | $kg/m^2$, tray-level measurement; or $lb/ft^2$, tray-level measurement | Assessed cumulatively across 1st, 2nd, and 3rd breaks |

**= at date when at least half of tray is of harvestable maturity in break

Results

Objective Description of the Variety 'RO10425'

The following detailed description sets forth the breeding procedures and the characteristics of new cultivar designated 'RO10425'. The strain is maintained and propagated as vegetative mycelium. Spawn (inoculum for the substrate compost) is prepared from the vegetative mycelium. The variety has shown uniformity and stability for the traits, within the limits of expected environmental influence for the traits.

All homokaryons utilized are strains of *Agaricus bisporus.*

Two initial homokaryotic strains were used for breeding. Wild brown strain AA-0096 was crossed with a commercial off-white hybrid mushroom strain.

More specifically, in a first cross, an AA-0096 slow growing SSI (sg) was crossed with a commercial off-white hybrid protoplast (p).

A progeny homokaryon resultant from this cross was then selected and backcrossed to the commercial off-white hybrid parent strain. A homokaryon produced by the backcrossing was then selected and crossed to a homokaryon of a bridging cross strain. This cross produced 'RO10425'.

There are multiple characteristics of 'RO10425' distinguishable from other varieties, such as a different cap color, rounder cap shape, thicker cap apex flesh, thicker cap edge flesh, and higher or as high yield at second break compared to other available brown commercial strains. Other characteristics of 'RO10425' distinguishable from other varieties are described below (compared to commercial line 'BR06', commercial line 'B14528', and related variety 'RO14176').

Figure 9:
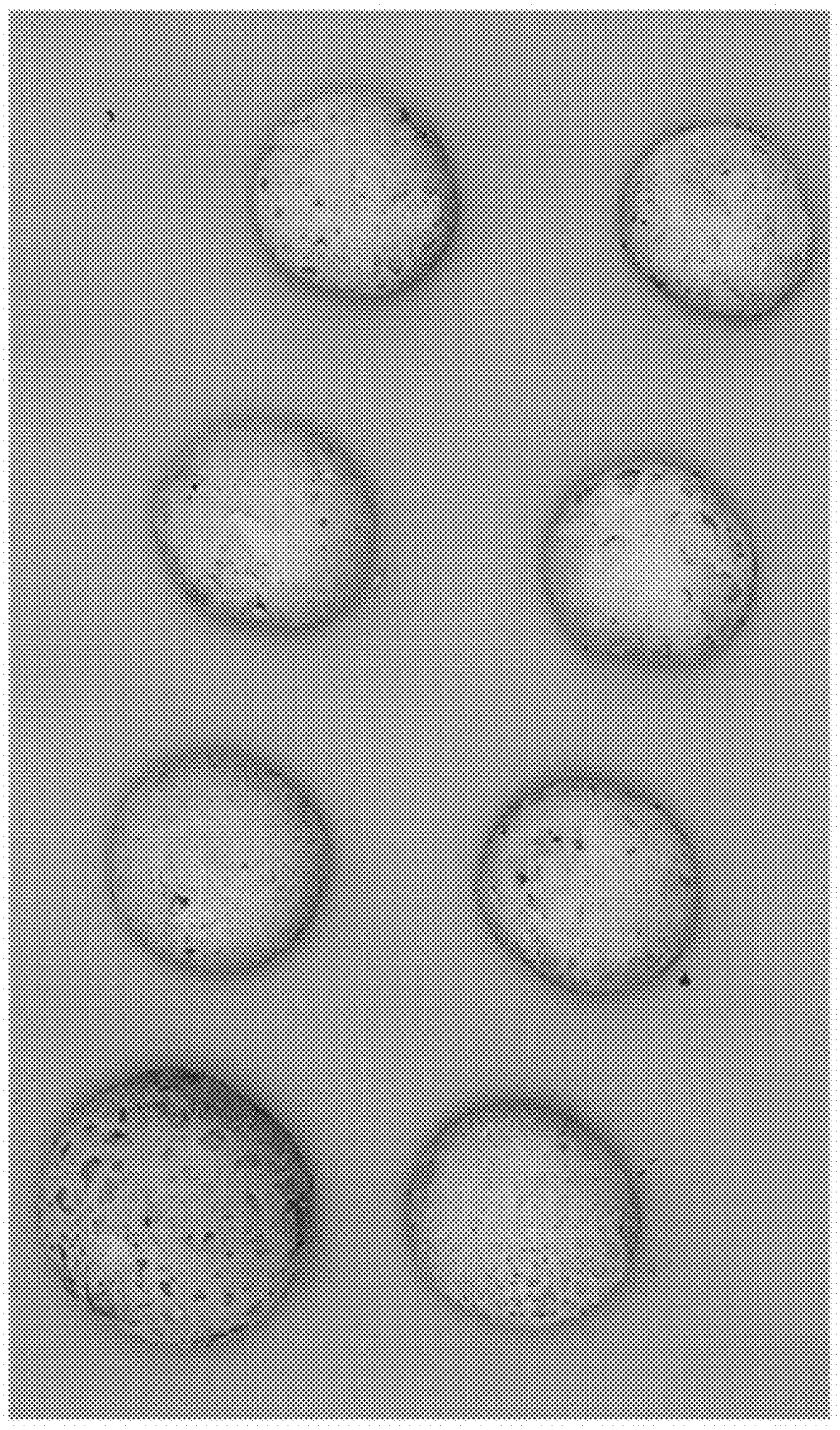
FIG. 9 shows multiple mushroom caps of variety ‘RO10425’ from a top-down view.
Figure 10:
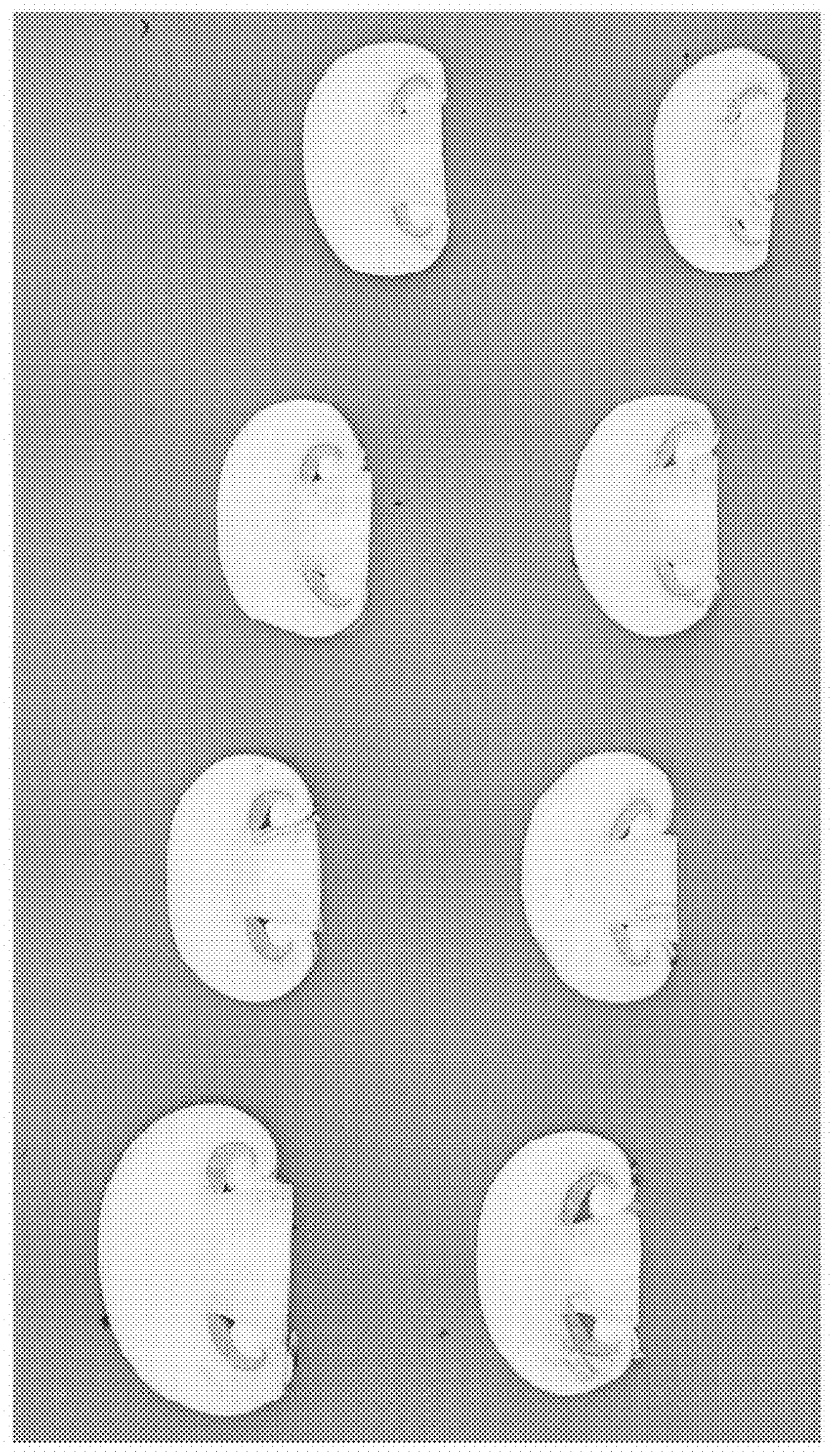
FIG. 10 shows multiple longitudinal slices of mushrooms of variety ‘RO10425’.

FIG. 9 and FIG. 10 show mushroom caps and longitudinal slices, respectively, of strain 'RO10425'.

Comparison to Other Mushroom Varieties

Initial Trials

Tray-Level Comparisons

In further evidence of the distinctness and superiority of mushroom strain 'RO10425', provided below are the results of trials conducted across multiple strains' yielded trays of mushrooms. These tray trials compare yield at each break. Characteristics were measured from 15 trays of strain 'RO10425' mushrooms and 23 trays of strain 'BR06' mushrooms (Table 2A and 2B), and corresponding measurements were taken from 24 trays of strain 'RO14176' mushrooms (Table 3A and 3B).

Table 2A below provides qualitative comparisons between mushroom strain 'RO10425' and strain 'BR06'. Column 1 lists the tray-level characteristic (as described in Table 1), column 2 shows the qualitative descriptor for the characteristic for mushroom strain 'RO10425' relative to 'BR06', and column 3 shows the qualitative descriptor for mushroom strain 'BR06' relative to 'RO10425'.

TABLE 2A

| Characteristic | 'RO10425' | 'BR06' |
|---|---|---|
| First Break | | |
| Yield (lb/ft$^2$) | Lower | Higher |
| Second Break | | |
| Yield (lb/ft$^2$) | Similar | Similar |
| Third Break | | |
| Yield (lb/ft$^2$) | Higher | Lower |
| All Breaks Combined | | |
| Yield (lb/ft$^2$) | Similar | Similar |

Table 2B below provides quantitative comparisons between mushroom strain 'RO10425' and strain 'BR06'. Column 1 lists the tray-level characteristics (as described in Table 1), column 2 shows the average value of the characteristic for mushroom strain 'RO10425', column 3 shows the standard deviation of the characteristic for mushroom strain 'RO10425', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate $p<0.05$.

TABLE 2B

| | 'RO10425' | | 'BR06' | | |
|---|---|---|---|---|---|
| Characteristic | Average | St. Dev. | Average | St. Dev. | p-value |
| First Break | | | | | |
| Yield (lb/ft$^2$) | 1.61 | 0.64 | 2.54 | 1.29 | **1.33E−02** |
| Second Break | | | | | |
| Yield (lb/ft$^2$) | 1.69 | 0.48 | 1.47 | 0.51 | 1.92E−01 |
| Third Break | | | | | |
| Yield (lb/ft$^2$) | 1.32 | 0.41 | 0.75 | 0.50 | **8.12E−04** |
| All Breaks Combined | | | | | |
| Yield (lb/ft$^2$) | 4.62 | 0.61 | 4.76 | 1.24 | 6.79E−01 |

Table 3A below provides qualitative comparisons between mushroom strain 'RO10425' and strain 'RO14176'. Column 1 lists the tray-level characteristic (as described in Table 1), column 2 shows the qualitative descriptor for the characteristic for mushroom strain 'RO10425' relative to 'RO14176', and column 3 shows the qualitative descriptor for mushroom strain 'RO14176' relative to 'RO10425'.

TABLE 3A

| Characteristic | 'RO10425' | 'RO14176' |
|---|---|---|
| First Break | | |
| Yield (lb/ft$^2$) | Lower | Higher |
| Second Break | | |
| Yield (lb/ft$^2$) | Similar | Similar |
| Third Break | | |
| Yield (lb/ft$^2$) | Higher | Lower |
| All Breaks Combined | | |
| Yield (lb/ft$^2$) | Lower | Higher |

Table 3B below provides quantitative comparisons between mushroom strain 'RO10425' and strain 'BR06'. Column 1 lists the tray-level characteristics (as described in Table 1), column 2 shows the average value of the characteristic for mushroom strain 'RO10425', column 3 shows the standard deviation of the characteristic for mushroom strain 'RO10425', column 4 shows the average value of the characteristic for mushroom strain 'RO14176', column 5 shows the standard deviation of the characteristic for mushroom strain 'RO14176', and column 6 shows the p-values of two-sample, two-sided t-tests. Bolded p-values indicate p<0.05.

TABLE 3B

| | 'RO10425' | | 'RO14176' | | |
|---|---|---|---|---|---|
| Characteristic | Average | St. Dev. | Average | St. Dev. | p-value |
| First Break | | | | | |
| Yield (lb/ft$^2$) | 1.61 | 0.64 | 2.54 | 0.83 | **7.01E−04** |
| Second Break | | | | | |
| Yield (lb/ft$^2$) | 1.69 | 0.48 | 1.91 | 0.52 | 1.91E−01 |
| Third Break | | | | | |
| Yield (lb/ft$^2$) | 1.32 | 0.41 | 0.92 | 0.38 | **3.41E−03** |
| All Breaks Combined | | | | | |
| Yield (lb/ft$^2$) | 4.62 | 0.61 | 5.37 | 1.08 | **1.94E−02** |

Individual Mushroom-Level Comparisons

In additional evidence of the distinctness and superiority of mushroom strain 'RO10425', provided below is a summary of precise quantitative measurements of individual mushrooms at first and second breaks. These data compare Cap L* Value, Cap a* Value, and Cap b* Values in the International Commission on Illumination (CIELAB) color space, Cap Diameter, Cap Height, Cap Flesh Thickness, Stipe Diameter, Relative Cap Height, Relative Cap Flesh Thickness, and Relative Stipe Diameter (as described in Table 1). Measurements from 49 first break and 37 second break 'RO10425' mushrooms were compared to 80 first break and 40 second break 'BR06' mushrooms (Tables 4A and 4B).

Table 4A below provides qualitative comparisons between mushroom strain 'RO10425' and strain 'BR06'. Column 1 lists the mushroom-level characteristics (as described in Table 1), column 2 shows the qualitative descriptor for the characteristic for mushroom strain 'RO10425' relative to 'BR06', and column 3 shows the qualitative descriptor for mushroom strain 'BR06' relative to 'RO10425'.

TABLE 4A

| Characteristic | 'RO10425' | 'BR06' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Similar | Similar |
| Cap Height | Similar | Similar |
| Cap Flesh Thickness | Similar | Similar |
| Stipe Diameter | Larger | Smaller |
| Relative Cap Height | Similar | Similar |
| Relative Cap Flesh Thickness | Thicker | Thinner |
| Relative Stipe Diameter | Larger | Smaller |
| Second Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Larger | Smaller |
| Cap Height | Taller | Shorter |
| Cap Flesh Thickness | Thicker | Thinner |
| Stipe Diameter | Larger | Smaller |

TABLE 4A-continued

| Characteristic | 'RO10425' | 'BR06' |
|---|---|---|
| Relative Cap Height | Similar | Similar |
| Relative Cap Flesh Thickness | Similar | Similar |
| Relative Stipe Diameter | Similar | Similar |

Table 4B below provides quantitative comparisons between mushroom strain 'RO10425' and strain 'BR06'. Column 1 lists the mushroom-level characteristics (as described in Table 1), column 2 shows the average value of the characteristic for mushroom strain 'RO10425', column 3 shows the standard deviation of the characteristic for mushroom strain 'RO10425', column 4 shows the average value of the characteristic for mushroom strain 'BR06', column 5 shows the standard deviation of the characteristic for mushroom strain 'BR56', and column 6 shows the p-values of two-sample, two-sided t-tests. Bolded p-values indicate p<0.05.

TABLE 4B

| | 'RO10425' | | 'BR06' | | |
|---|---|---|---|---|---|
| Characteristic | Average | St. Dev. | Average | St. Dev. | p-value |
| First Break | | | | | |
| Cap L* Value (dark-light) | 65.84 | 5.15 | 62.20 | 5.58 | **3.22E−04** |
| Cap a* Value (green-red) | 7.51 | 0.99 | 9.43 | 1.15 | **5.94E−17** |
| Cap b* Value (blue-yellow) | 26.03 | 1.29 | 28.67 | 1.63 | **7.91E−17** |
| Cap Diameter | 43.45 | 3.41 | 44.05 | 3.80 | 3.70E−01 |
| Cap Height | 27.09 | 1.99 | 27.45 | 1.99 | 3.27E−01 |
| Cap Flesh Thickness | 15.03 | 1.42 | 14.57 | 1.46 | 8.09E−02 |
| Stipe Diameter | 21.66 | 2.08 | 20.03 | 2.08 | **3.18E−05** |
| Relative Cap Height | 0.62 | 0.03 | 0.62 | 0.04 | 9.82E−01 |
| Relative Cap Flesh Thickness | 0.35 | 0.04 | 0.33 | 0.03 | **1.61E−02** |
| Relative Stipe Diameter | 0.56 | 0.05 | 0.53 | 0.03 | **1.02E−03** |
| Second Break | | | | | |
| Cap L* Value (dark-light) | 64.44 | 2.79 | 62.19 | 3.79 | **4.12E−03** |
| Cap a* Value (green-red) | 7.05 | 0.79 | 7.99 | 1.07 | **3.86E−05** |
| Cap b* Value (blue-yellow) | 26.48 | 1.15 | 27.01 | 1.06 | **3.64E−02** |
| Cap Diameter | 45.20 | 3.51 | 41.98 | 4.43 | **7.39E−04** |
| Cap Height | 28.78 | 2.27 | 26.81 | 2.89 | **1.42E−03** |
| Cap Flesh Thickness | 15.19 | 1.61 | 14.30 | 1.53 | **1.54E−02** |
| Stipe Diameter | 20.90 | 2.02 | 18.74 | 3.24 | **8.38E−04** |
| Relative Cap Height | 0.64 | 0.04 | 0.64 | 0.03 | 8.37E−01 |
| Relative Cap Flesh Thickness | 0.34 | 0.04 | 0.34 | 0.02 | 5.52E−01 |
| Relative Stipe Diameter | 0.46 | 0.04 | 0.45 | 0.05 | 8.97E−02 |

Additional analyses were performed on the measurements taken across individual mushrooms of each variety at multiple breaks, in order to compare more generalized mushroom traits irrespective of whether the mushrooms belonged to the first vs. second break of harvesting. The same characteristics described above (see Table 1) were measured from 86 mushrooms of strain 'RO10425' across the first and second break, and corresponding measurements were taken from 150 mushrooms of strain 'BR06' across the first and second break (Table 5A and 5B).

Table 5A below provides qualitative comparisons between mushroom strain 'RO10425' and strain 'BR06' made irrespective of break. Column 1 lists the mushroom-level characteristics (as described in Table 1), column 2 shows the qualitative descriptor for the characteristic for mushroom strain 'RO10425' relative to 'BR06', and column 3 shows the qualitative descriptor for mushroom strain 'BR06' relative to 'RO10425'.

TABLE 5A

| Characteristic | 'RO10425' | 'BR06' |
|---|---|---|
| Cap L* Value (dark-light) | Lighter | Darker |
| Cap a* Value (green-red) | Greener | Redder |
| Cap b* Value (blue-yellow) | Bluer | Yellower |
| Cap Diameter | Larger | Smaller |
| Cap Height | Taller | Shorter |
| Cap Flesh Thickness | Thicker | Thinner |
| Stipe Diameter | Larger | Smaller |
| Relative Cap Height | Taller | Shorter |
| Relative Cap Flesh Thickness | Thicker | Thinner |
| Relative Stipe Diameter | Larger | Smaller |

Table 5B below provides quantitative comparisons between mushroom strain 'RO10425' and strain 'BR06'. Column 1 lists the mushroom-level characteristics (as described in Table 1), column 2 shows the average value of the characteristic for mushroom strain 'RO10425', column 3 shows the standard deviation of the characteristic for mushroom strain 'RO10425', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate p<0.05.

TABLE 5B

| | 'RO10425' | | 'BR06' | | |
|---|---|---|---|---|---|
| Characteristic | Average | St. Dev. | Average | St. Dev. | p-value |
| Cap L* Value (dark-light) | 65.24 | 4.33 | 62.86 | 4.95 | **2.49E−04** |
| Cap a* Value (green-red) | 7.31 | 0.93 | 8.77 | 1.31 | **3.90E−17** |
| Cap b* Value (blue-yellow) | 26.22 | 1.24 | 28.31 | 1.61 | **5.99E−21** |
| Cap Diameter | 44.20 | 3.55 | 42.84 | 4.00 | **9.33E−03** |
| Cap Height | 27.82 | 2.26 | 26.53 | 2.59 | **1.55E−04** |
| Cap Flesh Thickness | 15.10 | 1.50 | 14.01 | 1.68 | **1.12E−06** |
| Stipe Diameter | 21.33 | 2.07 | 18.70 | 2.98 | **6.06E−12** |
| Relative Cap Height | 0.63 | 0.03 | 0.62 | 0.04 | **4.84E−02** |
| Relative Cap Flesh Thickness | 0.34 | 0.04 | 0.33 | 0.03 | **9.34E−04** |
| Relative Stipe Diameter | 0.48 | 0.04 | 0.44 | 0.05 | **1.96E−12** |

Tables 6A and 6B compare instant strain 'RO10425' and related strain 'RO14176'. Table 6A below provides qualitative comparisons between mushroom strain 'RO10425' and strain 'RO14176'. Measurements from 49 first break and 37 second break 'RO10425' mushrooms were compared to 80 first break and 40 second break 'RO14176' mushrooms (Tables 6A and 6B). Column 1 lists the mushroom-level characteristics (as described in Table 1), column 2 shows the qualitative descriptor for the characteristic for mushroom strain 'RO10425' relative to 'RO14176', and column 3 shows the qualitative descriptor for mushroom strain 'RO14176' relative to 'RO10425'.

TABLE 6A

| Characteristic | 'RO10425' | 'RO14176' |
|---|---|---|
| First Break | | |
| Cap L* Value (dark-light) | Similar | Similar |
| Cap a* Value (green-red) | Similar | Similar |
| Cap b* Value (blue-yellow) | Similar | Similar |
| Cap Diameter | Similar | Similar |
| Cap Height | Shorter | Taller |
| Stipe Diameter | Larger | Smaller |
| Relative Cap Height | Shorter | Taller |
| Relative Cap Flesh Thickness | Similar | Similar |
| Relative Stipe Diameter | Larger | Smaller |
| Second Break | | |
| Cap L* Value (dark-light) | Similar | Similar |
| Cap a* Value (green-red) | Redder | Greener |
| Cap b* Value (blue-yellow) | Yellower | Bluer |
| Cap Diameter | Larger | Smaller |
| Cap Height | Similar | Similar |
| Stipe Diameter | Larger | Smaller |
| Relative Cap Height | Shorter | Taller |
| Relative Cap Flesh Thickness | Thinner | Thicker |
| Relative Stipe Diameter | Similar | Similar |

Table 6B below provides quantitative comparisons between mushroom strain 'RO10425' and strain 'RO14176'. Column 1 lists the mushroom-level characteristics (as described in Table 1), column 2 shows the average value of the characteristic for mushroom strain 'RO10425', column 3 shows the standard deviation of the characteristic for mushroom strain 'RO10425', column 4 shows the average value of the characteristic for mushroom strain 'RO14176', column 5 shows the standard deviation of the characteristic for mushroom strain 'RO14176', and column 6 shows the p-values of two-sample, two-sided t-tests. Bolded p-values indicate p<0.05.

TABLE 6B

| | 'RO10425' | | 'RO14176' | | |
|---|---|---|---|---|---|
| Characteristic | Average | St. Dev. | Average | St. Dev. | p-value |
| First Break | | | | | |
| Cap L* Value (dark-light) | 65.84 | 5.15 | 65.91 | 4.79 | 9.38E−01 |
| Cap a* Value (green-red) | 7.51 | 0.99 | 7.49 | 1.05 | 9.32E−01 |
| Cap b* Value (blue-yellow) | 26.03 | 1.29 | 26.35 | 1.35 | 1.82E−01 |
| Cap Diameter | 43.45 | 3.41 | 43.53 | 3.27 | 9.01E−01 |
| Cap Height | 27.09 | 1.99 | 27.89 | 2.12 | **3.55E−02** |
| Cap Flesh Thickness | 15.03 | 1.42 | 15.33 | 1.36 | 2.42E−01 |
| Stipe Diameter | 21.66 | 2.08 | 19.99 | 1.90 | **7.06E−06** |
| Relative Cap Height | 0.62 | 0.03 | 0.64 | 0.03 | **2.43E−03** |
| Relative Cap Flesh Thickness | 0.35 | 0.04 | 0.35 | 0.03 | 3.25E−01 |
| Relative Stipe Diameter | 0.50 | 0.04 | 0.46 | 0.04 | **4.71E−07** |
| Second Break | | | | | |
| Cap L* Value (dark-light) | 64.44 | 2.79 | 65.61 | 3.67 | 1.24E−01 |
| Cap a* Value (green-red) | 7.05 | 0.79 | 6.36 | 0.76 | **2.32E−04** |
| Cap b* Value (blue-yellow) | 26.48 | 1.15 | 25.05 | 1.46 | **1.07E−05** |
| Cap Diameter | 45.20 | 3.51 | 41.88 | 2.68 | **1.23E−05** |
| Cap Height | 28.78 | 2.27 | 28.22 | 2.12 | 2.65E−01 |
| Cap Flesh Thickness | 15.19 | 1.61 | 15.75 | 1.61 | 1.31E−01 |
| Stipe Diameter | 20.90 | 2.02 | 19.16 | 2.29 | **6.92E−04** |
| Relative Cap Height | 0.64 | 0.04 | 0.67 | 0.04 | **7.23E−05** |
| Relative Cap Flesh Thickness | 0.34 | 0.04 | 0.38 | 0.04 | **1.79E−05** |
| Relative Stipe Diameter | 0.46 | 0.04 | 0.46 | 0.05 | 6.21E−01 |

Figure 6:
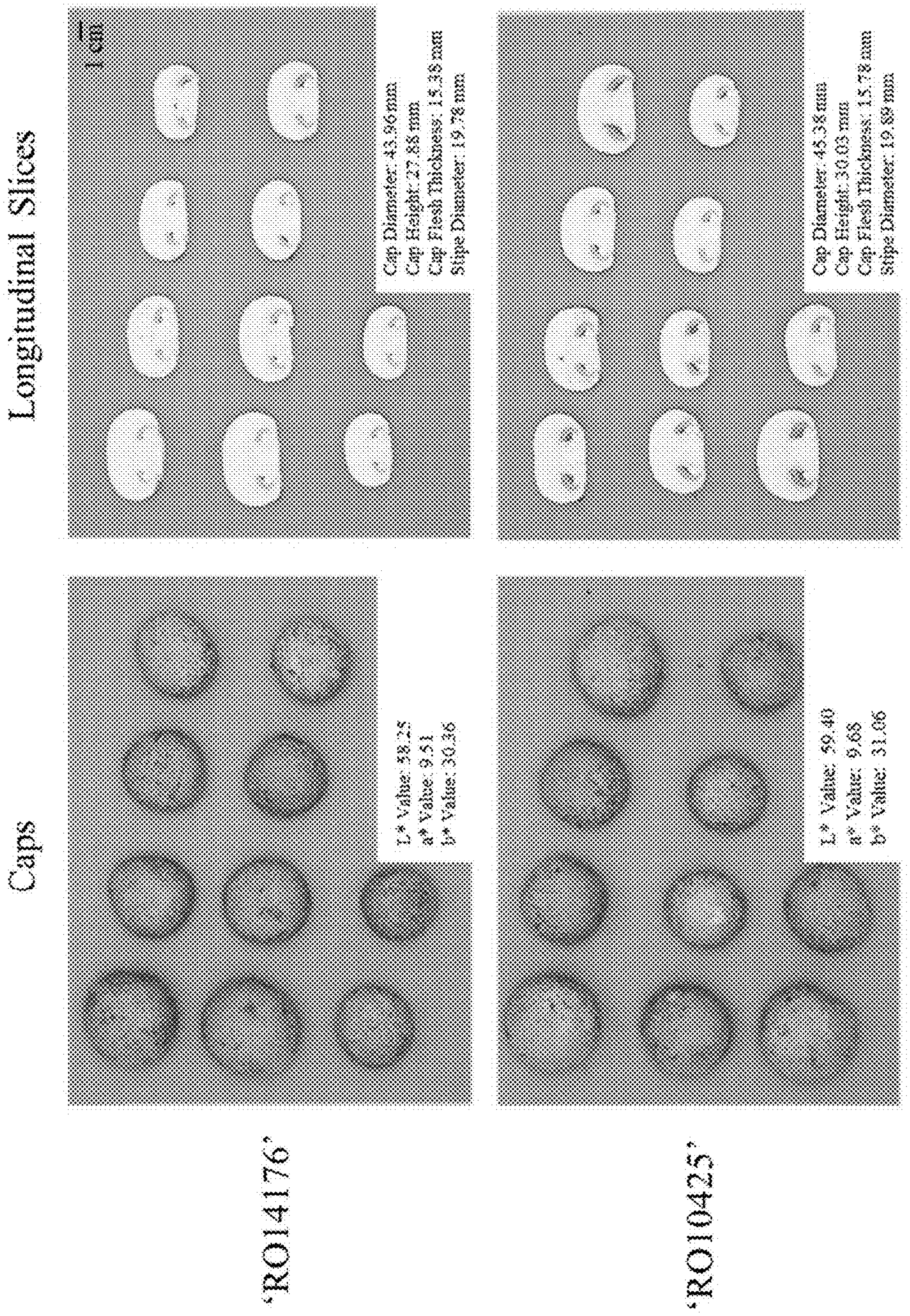
FIG. 6 shows comparisons between mushrooms of variety 'RO14176' (top row) and variety 'RO10425' (bottom row). The top left panel shows caps of 10 representative mushrooms from variety 'RO14176' and their average L*, a*, and b* values. The top right panel shows a longitudinal slice of each mushroom cap in the top left panel with the 10 mushrooms' average cap diameter, cap height, cap flesh thickness, and stipe diameters reported in millimeters. The bottom left panel shows caps of 10 representative mushrooms from variety 'RO10425' and their average L*, a*, and b* values. The bottom right panel shows a longitudinal slice of each mushroom cap in the bottom left panel with the 10 mushrooms' average cap diameter, cap height, cap flesh thickness, and stipe diameters reported in millimeters. Mushrooms pictured were grown in the same room, under the same environmental conditions, and were harvested from the same trial in April 2025. All photos have the same scale. Scale bar=1 cm.

FIG. 6 shows representative caps and longitudinal sections of caps from mushrooms of strain 'RO10425' compared to mushrooms of strain 'RO14176'.

Additional analysis was conducted for measurements taken across individual mushrooms of each variety at multiple breaks, in order to compare more generalized mushroom traits irrespective of whether the mushrooms belonged to the first vs. second break of harvesting. The same characteristics described above (see Table 1) were measured from 86 mushrooms of strain 'RO10425' across the first and second break, and corresponding measurements were taken from 170 mushrooms of strain 'RO14176' across the first and second break (Table 7A and 7B). Table 7A below provides qualitative comparisons between mushroom strain 'RO10425' and strain 'RO14176'. Column 1 lists the mushroom-level characteristics (as described in Table 1), column 2 shows the qualitative descriptor for the characteristic for mushroom strain 'RO10425' relative to 'RO14176', and column 3 shows the qualitative descriptor for mushroom strain 'RO14176' relative to 'RO10425'.

TABLE 7A

| Characteristic | 'RO10425' | 'RO14176' |
|---|---|---|
| Cap L* Value (dark-light) | Darker | Lighter |
| Cap a* Value (green-red) | Redder | Greener |
| Cap b* Value (blue-yellow) | Similar | Similar |
| Cap Diameter | Larger | Shorter |
| Cap Height | Taller | Shorter |
| Cap Flesh Thickness | Similar | Similar |
| Stipe Diameter | Larger | Smaller |
| Relative Cap Height | Shorter | Taller |
| Relative Cap Flesh Thickness | Similar | Similar |
| Relative Stipe Diameter | Larger | Smaller |

Table 7B below provides quantitative comparisons between mushroom strain 'RO10425' and strain 'RO14176'. Column 1 lists the mushroom-level characteristics (as described in Table 1), column 2 shows the average value of the characteristic for mushroom strain 'RO10425', column 3 shows the standard deviation of the characteristic for mushroom strain 'RO10425', column 4 shows the average value of the characteristic for mushroom strain 'RO14176', column 5 shows the standard deviation of the characteristic for mushroom strain 'RO14176', and column 6 shows the p-values of two-sample, two-sided t-tests. Bolded p-values indicate p<0.05.

TABLE 7B

| | 'RO10425' | | 'RO14176' | | |
|---|---|---|---|---|---|
| Characteristic | Average | St. Dev. | Average | St. Dev. | p-value |
| Cap L* Value (dark-light) | 65.24 | 4.33 | 67.15 | 4.61 | **1.60E−03** |
| Cap a* Value (green-red) | 7.31 | 0.93 | 6.93 | 1.09 | **6.45E−03** |
| Cap b* Value (blue-yellow) | 26.22 | 1.24 | 26.44 | 1.59 | 2.60E−01 |
| Cap Diameter | 44.20 | 3.55 | 42.36 | 3.30 | **5.22E−05** |
| Cap Height | 27.82 | 2.26 | 27.14 | 2.37 | **2.88E−02** |
| Cap Flesh Thickness | 15.10 | 1.50 | 14.70 | 1.84 | 7.93E−02 |
| Stipe Diameter | 21.33 | 2.07 | 18.53 | 2.68 | **1.68E−15** |
| Relative Cap Height | 0.63 | 0.03 | 0.64 | 0.04 | **2.54E−02** |
| Relative Cap Flesh Thickness | 0.34 | 0.04 | 0.35 | 0.04 | 3.75E−01 |
| Relative Stipe Diameter | 0.48 | 0.04 | 0.44 | 0.05 | **2.98E−11** |

Additional Trials

Tray-Level Comparisons

Several additional trials were conducted for characterizing 'RO10425'. Table 8 below provides qualitative comparisons between mushroom strain 'RO10425' and strain 'BR06'. Traits of particular interest are bolded. Column 1 lists the tray-level characteristics (as described in Table 1), column 2 shows the qualitative descriptor for the characteristic for mushroom strain 'RO10425' relative to 'BR06', and column 3 shows the qualitative descriptor for mushroom strain 'BR06' relative to 'RO10425'.

TABLE 8

| Characteristic | 'RO10425' | 'BR06' |
|---|---|---|
| Before First Break | | |
| **Days to Pinset** | Similar | Similar |
| First Break | | |
| **Days to 1st Break** | Similar | Similar |
| **Percent Harvested Speed** | Similar | Similar |
| **Yield (kg/m$^2$)** | Similar | Similar |
| Second Break | | |
| **Days to 2nd Break** | Similar | Similar |
| **Yield (kg/m$^2$)** | Higher | Lower |
| Third Break | | |
| **Yield (kg/m$^2$)** | Similar | Similar |
| All Breaks Combined | | |
| **Yield (kg/m$^2$)** | Similar | Similar |

The calculations that informed these qualitative descriptors are shown in Table 10.

Table 9 below provides qualitative comparisons between mushroom strain 'RO10425' and strain 'B14528'. Column 1 lists the tray-level characteristic (as described in Table 1), column 2 shows the qualitative descriptor for the characteristic for mushroom strain 'RO10425'relative to 'B14528', and column 3 shows the qualitative descriptor for mushroom strain 'B14528' relative to 'RO10425'.

TABLE 9

| Characteristic | 'RO10425' | 'B14528' |
|---|---|---|
| Before First Break | | |
| **Days to Pinset** | Similar | Similar |
| First Break | | |
| **Days to 1st Break** | Similar | Similar |
| **Percent Harvested Speed** | Similar | Similar |
| **Yield (kg/m$^2$)** | Similar | Similar |
| Second Break | | |
| **Days to 2nd Break** | Similar | Similar |
| **Yield (kg/m$^2$)** | Similar | Similar |
| Third Break | | |
| **Yield (kg/m$^2$)** | Similar | Similar |
| All Breaks Combined | | |
| **Yield (kg/m$^2$)** | Similar | Similar |

The calculations that informed these qualitative descriptors are shown in Table 10.

The first part of analyzing trait measurements in the additional trials herein included making comparisons between all three of instant strain 'RO10425', comparative strain 'BR06', and comparative strain 'B14528'. For these three strains, a Shapiro-Wilk test and a Levene test were performed first to assess if the data satisfy the assumptions of normality and equal variances among groups, respectively, of a standard ANOVA. The Shapiro-Wilk test and Levene test determined that most of these traits satisfied neither assumption. Therefore, a Kruskal-Wallis test (Kruskal, W. H., & Wallis, W. A. (1952). Use of ranks in one-criterion variance analysis. Journal of the American statistical Association, 47(260), 583-621), a non-parametric variation of ANOVA that does not assume normality, equal variances among groups, or equal sample sizes among groups, was performed. Medians and interquartile ranges (IQR) were reported, as these metrics are robust to non-normal distributions. Means are also reported for consistency with normally-distributed traits.

The Shapiro-Wilk test and Levene test determined that most developmental timing traits (Days to Pinset, Days to 1st Break, and Days to 2nd Break) and yield traits were not normally distributed and variances among groups were not equal. The Kruskal-Wallis test and Dunn post-hoc test ("Dunn's Test"; Dunn, O. J. (1964). Multiple comparisons using rank sums. Technometrics, 6(3), 241-252) were used in these cases. When the Kruskal-Wallis test results were significant based on a threshold of $p<0.05$, Dunn's test was performed post-hoc to make pairwise strain comparisons (Dunn, 1964). P-values were adjusted using the Bonferroni correction to minimize risk of Type 1 error (false significance). An exception to this trend was Percent Harvested Speed, which was normally distributed and exhibited equal variance for all strains. For assessing Percent Harvested Speed, a standard ANOVA was used and a Tukey Honestly Significant Difference (HSD) test was performed post-hoc for pairwise strain comparisons. Standard deviations multiplied by 100 for consistency alongside percentages ("SD*100") were reported for this trait. This testing was performed on groups of three strains, as displayed in Table 10, but the other results herein using this test show a pairwise subset of the tests for consistency with the initial trials.

In Table 10, column 1 shows each trait and the strains compared for said trait, column 2 shows the mean value for that strain's measurements of that trait, column 3 shows the median value of the same measurements, column 4 shows the interquartile range ("IQR") for the same measurements, column 5 shows the number of trials conducted, and column 6 shows the statistical significance group calculated for that strain for that trait according to Dunn's Test. Traits of particular interest are bolded.

TABLE 10

| Variety | Mean | Median | IQR | Number of Trials | Significance Group (Dunn's Test) |
|---|---|---|---|---|---|
| | | Before First Break **Days to Pinset** | | | |
| 'RO10425' | 12.00 | 12.00 | 2.00 | 4 | a |
| 'B14528' | 12.00 | 12.00 | 1.75 | 4 | a |
| 'BR06' | 12.40 | 12.00 | 1.00 | 4 | a |
| | | First Break **Days to 1st Break** | | | |
| 'RO10425' | 18.00 | 18.00 | 1.00 | 4 | a |
| 'B14528' | 17.60 | 18.00 | 1.75 | 4 | a |
| 'BR06' | 18.10 | 18.00 | 1.00 | 4 | a |
| | | **Yield (kg/m$^2$)** | | | |
| 'RO10425' | 10.64 | 10.64 | 1.76 | 3 | a |
| 'B14528' | 9.81 | 9.52 | 4.44 | 3 | a |
| 'BR06' | 10.30 | 8.35 | 5.57 | 3 | a |
| | | Second Break **Days to 2nd Break** | | | |
| 'RO10425' | 24.90 | 25.00 | 1.75 | 4 | a |
| 'B14528' | 24.80 | 25.00 | 1.00 | 4 | a |
| 'BR06' | 25.30 | 26.00 | 1.00 | 4 | a |

TABLE 10-continued

| | | | | | |
|---|---|---|---|---|---|
| | | **Yield (kg/m$^2$)** | | | |
| 'RO10425' | 8.74 | 8.10 | 3.27 | 3 | a |
| 'B14528' | 7.13 | 6.93 | 1.51 | 3 | ab |
| 'BR06' | 6.20 | 5.86 | 1.61 | 3 | a |
| | | Third Break **Yield (kg/m$^2$)** | | | |
| 'RO10425' | 3.66 | 3.52 | 0.78 | 3 | ab |
| 'B14528' | 5.81 | 5.42 | 1.81 | 3 | b |
| 'BR06' | 2.64 | 1.95 | 2.10 | 3 | a |
| | | All Breaks Combined **Yield (kg/m$^2$)** | | | |
| 'RO10425' | 23.05 | 23.14 | 4.25 | 3 | a |
| 'B14528' | 22.75 | 22.61 | 2.29 | 3 | a |
| 'BR06' | 19.14 | 18.70 | 5.52 | 3 | a |
| Percent Harvested Speed (measured in First Break) | | | SD * 100 | | Significance Group (Tukey HSD) |
| 'RO10425' | 36.7% | 34.8% | 32.70 | 3 | a |
| 'B14528' | 36.2% | 45.2% | 25.00 | 3 | a |
| 'BR06' | 28.9% | 12.9% | 37.70 | 3 | a |

Individual Mushroom-Level Comparisons

In additional evidence of the distinctness and superiority of mushroom strain 'RO10425', provided below is a summary of precise quantitative measurements of individual mushrooms at first and second breaks. These data compare Cap L* Value, Cap a* Value, and Cap b* Values in the International Commission on Illumination (CIELAB) color space, Cap Apex Flesh Thickness, Cap Edge Flesh Thickness, and Cap Roundness (Calculated) (as described in Table 1). Measurements were taken for hundreds of mushrooms per trait, noted as sample size (n) in Tables 11B and 12B.

Table 11A below provides qualitative comparisons between mushroom strain 'RO10425' and strain 'BR06'. Traits of particular interest are bolded. Column 1 lists the mushroom-level characteristics (as described in Table 1), column 2 shows the qualitative descriptor for the characteristic for mushroom strain 'RO10425' relative to 'BR06', and column 3 shows the qualitative descriptor for mushroom strain 'BR06' relative to 'RO10425'.

TABLE 11A

| Characteristic | 'RO10425' | 'BR06' |
|---|---|---|
| | First Break | |
| Cap L* Value (dark-light) | Lighter | Darker |
| Cap a* Value (green-red) | Greener | Redder |
| Cap b* Value (blue-yellow) | Bluer | Yellower |
| **Cap Apex Flesh Thickness** | Thicker | Thinner |
| **Cap Edge Flesh Thickness** | Thicker | Thinner |
| **Cap Roundness (Calculated)** | Rounder | Flatter |
| | Second Break | |
| Cap L* Value (dark-light) | Lighter | Darker |
| Cap a* Value (green-red) | Greener | Redder |
| Cap b* Value (blue-yellow) | Bluer | Yellower |
| **Cap Apex Flesh Thickness** | Thicker | Thinner |
| **Cap Edge Flesh Thickness** | Thicker | Thinner |
| **Cap Roundness (Calculated)** | Rounder | Flatter |

Table B shows additional quantitative comparisons between mushroom strain 'RO10425' and strain 'BR06'. Column 1 shows each trait and the strains compared for said trait, column 2 shows the mean value for that strain's measurements of that trait, column 3 shows the median value of the same measurements, column 4 shows the interquartile range ("IQR") for the same measurements, column 5 shows the number of trials conducted, and column 6 shows the statistical significance group calculated for that strain for that trait according to Dunn's Test.

TABLE 11B

| Variety | Mean | Median | IQR | Number of Mushrooms (n) | Significance Group (Dunn's Test) |
|---|---|---|---|---|---|
| | | First Break<br>Cap L* Value (dark-light) | | | |
| 'RO10425' | 65.66 | 65.22 | 7.34 | 209 | a |
| 'BR06' | 63.30 | 62.74 | 9.83 | 797 | b |
| | | Cap a* Value (green-red) | | | |
| 'RO10425' | 7.35 | 7.43 | 1.97 | 209 | a |
| 'BR06' | 8.67 | 8.96 | 2.58 | 787 | b |
| | | Cap b* Value (blue-yellow) | | | |
| 'RO10425' | 28.43 | 28.58 | 3.10 | 209 | a |
| 'BR06' | 28.72 | 29.04 | 3.17 | 776 | b |
| | | **Cap Apex Flesh Thickness** | | | |
| 'RO10425' | 0.55 | 0.55 | 0.04 | 166 | a |
| 'BR06' | 0.52 | 0.52 | 0.05 | 541 | b |
| | | **Cap Edge Flesh Thickness** | | | |
| 'RO10425' | 0.30 | 0.31 | 0.05 | 166 | a |
| 'BR06' | 0.21 | 0.21 | 0.09 | 537 | b |
| | | **Cap Roundness (Calculated)** | | | |
| 'RO10425' | 0.64 | 0.63 | 0.05 | 166 | a |
| 'BR06' | 0.61 | 0.61 | 0.04 | 541 | b |
| | | Second Break<br>Cap L* Value (dark-light) | | | |
| 'RO10425' | 68.82 | 69.47 | 8.20 | 157 | a |
| 'BR06' | 65.68 | 65.49 | 5.90 | 340 | b |
| | | Cap a* Value (green-red) | | | |
| 'RO10425' | 6.15 | 6.26 | 2.55 | 157 | a |
| 'BR06' | 7.21 | 7.31 | 2.42 | 340 | b |
| | | Cap b* Value (blue-yellow) | | | |
| 'RO10425' | 27.69 | 27.46 | 2.54 | 157 | a |
| 'BR06' | 28.15 | 28.49 | 2.86 | 340 | b |
| | | **Cap Apex Flesh Thickness** | | | |
| 'RO10425' | 0.55 | 0.55 | 0.04 | 157 | a |
| 'BR06' | 0.51 | 0.52 | 0.07 | 362 | b |
| | | **Cap Edge Flesh Thickness** | | | |
| 'RO10425' | 0.32 | 0.32 | 0.05 | 157 | a |
| 'BR06' | 0.23 | 0.23 | 0.09 | 362 | b |
| | | **Cap Roundness (Calculated)** | | | |
| 'RO10425' | 0.61 | 0.61 | 0.05 | 157 | a |
| 'BR06' | 0.60 | 0.59 | 0.06 | 363 | b |

Table 12A below provides qualitative comparisons between mushroom strain 'RO10425' and strain 'B14528'. Traits of interest are bolded in Tables 12A and 12B. Column 1 lists the individual mushroom-level characteristic (as described in Table 1), column 2 shows the qualitative descriptor for the characteristic for mushroom strain 'RO10425' relative to 'B14528', and column 3 shows the qualitative descriptor for mushroom strain 'B14528' relative to 'RO010425'.

TABLE 12A

| Characteristic | 'RO10425' | 'B14528' |
|---|---|---|
| | First Break | |
| Cap L* Value (dark-light) | Lighter | Darker |
| Cap a* Value (green-red) | Greener | Redder |
| Cap b* Value (blue-yellow) | Bluer | Yellower |
| **Cap Apex Flesh Thickness** | Thicker | Thinner |
| **Cap Edge Flesh Thickness** | Thicker | Thinner |
| **Cap Roundness (Calculated)** | Rounder | Flatter |
| | Second Break | |
| Cap L* Value (dark-light) | Similar | Similar |
| Cap a* Value (green-red) | Similar | Similar |
| Cap b* Value (blue-yellow) | Similar | Similar |
| **Cap Apex Flesh Thickness** | Thicker | Thinner |
| **Cap Edge Flesh Thickness** | Thicker | Thinner |
| **Cap Roundness (Calculated)** | Rounder | Flatter |

Table 12B below provides quantitative comparisons between mushroom strain 'RO10425' and strain 'B14528', which resulted in the qualitative descriptors of Table 12A. Column 1 shows each individual mushroom-level trait (as described in Table 1) and the strains compared for said trait, column 2 shows the mean value for that strain's measurements of that trait, column 3 shows the median value of the same measurements, column 4 shows the interquartile range ("IQR") for the same measurements, column 5 shows the number of mushrooms assessed (n), and column 6 shows the statistical significance group calculated for that strain for that trait according to Dunn's Test.

TABLE 12B

| Variety | Mean | Median | IQR | Number of Mushrooms (n) | Significance Group (Dunn's Test) |
|---|---|---|---|---|---|
| | | First Break<br>Cap L* Value (dark-light) | | | |
| 'RO10425' | 65.66 | 65.22 | 7.34 | 209 | a |
| 'B14528' | 64.06 | 64.13 | 6.56 | 340 | c |
| | | Cap a* Value (green-red) | | | |
| 'RO10425' | 7.35 | 7.43 | 1.97 | 209 | a |
| 'B14528' | 8.26 | 8.31 | 2.13 | 340 | c |
| | | Cap b* Value (blue-yellow) | | | |
| 'RO10425' | 28.43 | 28.58 | 3.10 | 209 | a |
| 'B14528' | 30.31 | 30.16 | 3.39 | 340 | c |
| | | **Cap Apex Flesh Thickness** | | | |
| 'RO10425' | 0.55 | 0.55 | 0.04 | 166 | a |
| 'B14528' | 0.47 | 0.46 | 0.06 | 387 | c |
| | | **Cap Edge Flesh Thickness** | | | |
| 'RO10425' | 0.30 | 0.31 | 0.05 | 166 | a |
| 'B14528' | 0.22 | 0.22 | 0.08 | 387 | b |
| | | **Cap Roundness (Calculated)** | | | |
| 'RO10425' | 0.64 | 0.63 | 0.05 | 166 | a |
| 'B14528' | 0.61 | 0.61 | 0.05 | 389 | b |
| | | Second Break<br>Cap L* Value (dark-light) | | | |
| 'RO10425' | 68.82 | 69.47 | 8.20 | 157 | a |
| 'B14528' | 68.56 | 69.02 | 6.54 | 170 | a |
| | | Cap a* Value (green-red) | | | |
| 'RO10425' | 6.15 | 6.26 | 2.55 | 157 | a |
| 'B14528' | 6.09 | 5.96 | 2.05 | 170 | a |

TABLE 12B-continued

| Variety | Mean | Median | IQR | Number of Mushrooms (n) | Significance Group (Dunn's Test) |
|---|---|---|---|---|---|
| Cap b* Value (blue-yellow) | | | | | |
| 'RO10425' | 27.69 | 27.46 | 2.54 | 157 | a |
| 'B14528' | 27.37 | 27.78 | 3.22 | 170 | a |
| **Cap Apex Flesh Thickness** | | | | | |
| 'RO10425' | 0.55 | 0.55 | 0.04 | 157 | a |
| 'B14528' | 0.46 | 0.46 | 0.05 | 198 | c |
| **Cap Edge Flesh Thickness** | | | | | |
| 'RO10425' | 0.32 | 0.32 | 0.05 | 157 | a |
| 'B14528' | 0.23 | 0.23 | 0.06 | 198 | b |
| **Cap Roundness (Calculated)** | | | | | |
| 'RO10425' | 0.61 | 0.61 | 0.05 | 157 | a |
| 'B14528' | 0.60 | 0.60 | 0.05 | 198 | b |

As conducted in initial trials, comparisons were made between instant strain 'RO10425' and related strain 'RO14176'. Tables 13A below provides qualitative comparisons between mushroom strain 'RO10425' and strain 'RO14176'. Column 1 lists the mushroom-level characteristics (as described in Table 1), column 2 shows the qualitative descriptor for the characteristic for mushroom strain 'RO10425' relative to 'RO14176', and column 3 shows the qualitative descriptor for mushroom strain 'RO14176' relative to 'RO10425'.

TABLE 13A

| Characteristic | 'RO10425' | 'RO14176' |
|---|---|---|
| First Break | | |
| Cap L* Value (dark-light) | Darker | Lighter |
| Cap a* Value (green-red) | Redder | Greener |
| Cap b* Value (blue-yellow) | Similar | Similar |
| Cap Diameter | Similar | Similar |
| Cap Height | Similar | Similar |
| Cap Flesh Thickness | Similar | Similar |
| Stipe Diameter | Larger | Smaller |
| Relative Cap Height | Similar | Similar |
| Relative Cap Flesh Thickness | Similar | Similar |
| Relative Stipe Diameter | Larger | Smaller |
| Second Break | | |
| Cap L* Value (dark-light) | Similar | Similar |
| Cap a* Value (green-red) | Similar | Similar |
| Cap b* Value (blue-yellow) | Similar | Similar |
| Cap Diameter | Similar | Similar |
| Cap Height | Similar | Similar |
| Cap Flesh Thickness | Similar | Similar |
| Stipe Diameter | Larger | Smaller |
| Relative Cap Height | Similar | Similar |
| Relative Cap Flesh Thickness | Similar | Similar |
| Relative Stipe Diameter | Larger | Smaller |

Table 13B below provides quantitative comparisons between mushroom strain 'RO10425' and strain 'RO14176' that informed the qualitative comparisons of Table 13A. In Table 13B, Column 1 lists the mushroom-level characteristics (as described in Table 1), column 2 shows the average value of the characteristic for mushroom strain 'RO10425', column 3 shows the standard deviation of the characteristic for mushroom strain 'RO10425', column 4 shows the average value of the characteristic for mushroom strain 'RO14176', column 5 shows the standard deviation of the characteristic for mushroom strain 'RO14176', and column 6 shows the p-values of two-sample, two-sided t-tests. Bolded p-values indicate $p<0.05$.

TABLE 13B

| | 'RO10425' | | 'RO14176' | | |
|---|---|---|---|---|---|
| Characteristic | Average | St. Dev. | Average | St. Dev. | p-value |
| First Break | | | | | |
| Cap L* Value (dark-light) | 65.17 | 5.27 | 66.97 | 4.84 | **1.18E−05** |
| Cap a* Value (green-red) | 7.55 | 1.68 | 6.89 | 1.63 | **6.95E−07** |
| Cap b* Value (blue-yellow) | 28.52 | 2.09 | 28.46 | 2.07 | 6.92E−01 |
| Cap Diameter | 43.18 | 3.81 | 43.25 | 3.94 | 8.21E−01 |
| Cap Height | 27.67 | 2.65 | 27.87 | 2.19 | 3.44E−01 |
| Cap Flesh Thickness | 15.26 | 1.61 | 15.19 | 1.73 | 6.44E−01 |
| Stipe Diameter | 21.66 | 2.08 | 19.92 | 2.43 | **1.94E−06** |
| Relative Cap Height | 0.65 | 0.04 | 0.65 | 0.04 | 3.41E−01 |
| Relative Cap Flesh Thickness | 0.35 | 0.03 | 0.35 | 0.05 | 1.66E−01 |
| Relative Stipe Diameter | 0.50 | 0.04 | 0.45 | 0.05 | **1.50E−09** |
| Second Break | | | | | |
| Cap L* Value (dark-light) | 68.82 | 5.25 | 69.32 | 4.59 | 3.11E−01 |
| Cap a* Value (green-red) | 6.15 | 1.63 | 6.02 | 1.64 | 4.26E−01 |
| Cap b* Value (blue-yellow) | 27.69 | 1.91 | 27.50 | 2.11 | 3.19E−01 |
| Cap Diameter | 43.19 | 4.08 | 42.56 | 3.62 | 1.08E−01 |
| Cap Height | 26.65 | 2.49 | 26.28 | 2.29 | 1.31E−01 |
| Cap Flesh Thickness | 14.51 | 1.34 | 14.24 | 1.60 | 6.04E−02 |
| Stipe Diameter | 20.90 | 2.02 | 17.80 | 2.58 | **4.81E−11** |
| Relative Cap Height | 0.62 | 0.04 | 0.62 | 0.05 | 3.57E−01 |
| Relative Cap Flesh Thickness | 0.34 | 0.03 | 0.34 | 0.04 | 9.52E−01 |
| Relative Stipe Diameter | 0.46 | 0.04 | 0.42 | 0.05 | **1.84E−06** |

One of the advantages of the strain 'RO10425' is its incompatibility with other commercial strains. Table 14 below provides results of compatibility tests between strain 'RO010425' and commercial strain 'BR36', commercial strain 'B14528', related strain 'RO12756', and related strain 'RO14176'. These results indicate that strain 'RO10425' is incompatible with strain 'BR06', strain 'B14528', and related strain 'RO12756', while strain 'RO10425' is compatible with related strain 'RO14176'. This was true regardless of which tested strain served as the compost variety and which tested strain served as the casing variety.

TABLE 14

| Strains (compost variety/ | Mean | | Median | | SD | | | Significance |
|---|---|---|---|---|---|---|---|---|
| casing variety) | lb/ft$^2$ | kg/m$^2$ | lb/ft$^2$ | kg/m$^2$ | lb/ft$^2$ | kg/m$^2$ | Trials | Group |
| RO10425'/'RO10425' | 2.71 | 13.23 | 2.86 | 13.94 | 0.50 | 2.44 | 3 | a |
| RO12756'/'RO12756' | 2.62 | 12.79 | 2.61 | 12.74 | 0.41 | 2.00 | 3 | a |
| RO14176'/'RO14176' | 2.66 | 12.99 | 2.41 | 11.77 | 0.61 | 2.98 | 3 | a |
| BR06'/'BR06' | 2.62 | 12.79 | 2.46 | 11.99 | 1.15 | 5.61 | 2 | a |
| B14528'/'B14528' | 2.93 | 14.31 | 2.92 | 14.23 | 0.34 | 1.66 | 1 | a |

TABLE 14-continued

| Strains (compost variety/ casing variety) | Mean lb/ft$^2$ | Mean kg/m$^2$ | Median lb/ft$^2$ | Median kg/m$^2$ | SD lb/ft$^2$ | SD kg/m$^2$ | Trials | Significance Group |
|---|---|---|---|---|---|---|---|---|
| RO10425'/'RO14176', 'RO14176'/'RO10425' | 2.43 | 11.86 | 2.75 | 13.40 | 0.77 | 3.76 | 1 | a |
| RO10425'/'B14528', 'B14528'/'RO10425' | 0.71 | 3.47 | 0.65 | 3.15 | 0.17 | 0.83 | 1 | b |
| RO12756'/'RO10425', 'RO10425'/'RO12756' | 0.91 | 4.44 | 1.04 | 5.08 | 0.35 | 1.71 | 1 | b |
| RO10425'/'BR06', 'BR06'/'RO10425' | 0.80 | 3.91 | 0.92 | 4.47 | 0.51 | 2.49 | 1 | b |

Example 2: Characterization of 'RO14176'

The following example describes the characterization of strain 'RO14176' compared to commercial varieties.

Methodology

The measurements and calculations were conducted as in Example 1.

Results

Objective Description of the Variety 'RO14176'

The following detailed description sets forth the breeding procedures and the characteristics of new cultivar designated 'RO14176'. The strain is maintained and propagated as vegetative mycelium. Spawn (inoculum for the substrate compost) is prepared from the vegetative mycelium. The variety has shown uniformity and stability for the traits, within the limits of environmental influence for the traits.

All homokaryons utilized are strains of *Agaricus bisporus*.

Two initial strains were used for breeding. Wild brown strain AA-0096 was crossed with commercial off-white hybrid mushroom strain Amycel® XXX. More specifically, in a first cross, an AA-0096 slow growing SSI (sg) homokaryon was crossed with an Amycel® XXX protoplast (p) homokaryon. A progeny homokaryon resultant from this cross was then selected and backcrossed to Amycel® XXX. A homokaryon produced by the backcrossing was then selected and crossed to a homokaryon of a '4×29', a representative sample of which being available under ATCC Accession No. PTA-6877. This cross produced 'RO10425', a representative culture of which having been deposited under ATCC Accession No. PTA-127856. 'RO14176' was produced as a heterokaryon SSI derived from strain 'RO10425'. [00112]'RO14176' sets pins and produces harvestable mushrooms at first break and second break as fast or faster than available brown commercial strains. 'RO14176' additionally exhibits higher yield at third break, and higher overall yield, than available brown commercial strains. 'RO14176' also exhibits rounder cap shape, thicker cap apex flesh, thicker cap edge flesh, and a new cap color compared to available brown commercial strains. 'RO14176' additionally exhibits Percent Harvested Speed faster or as fast as other available brown commercial strains.

Other characteristics of 'RO14176' distinguishable from other varieties are described below (compared to commercial line 'BR06' and commercial line 'B14528').

Figure 7:
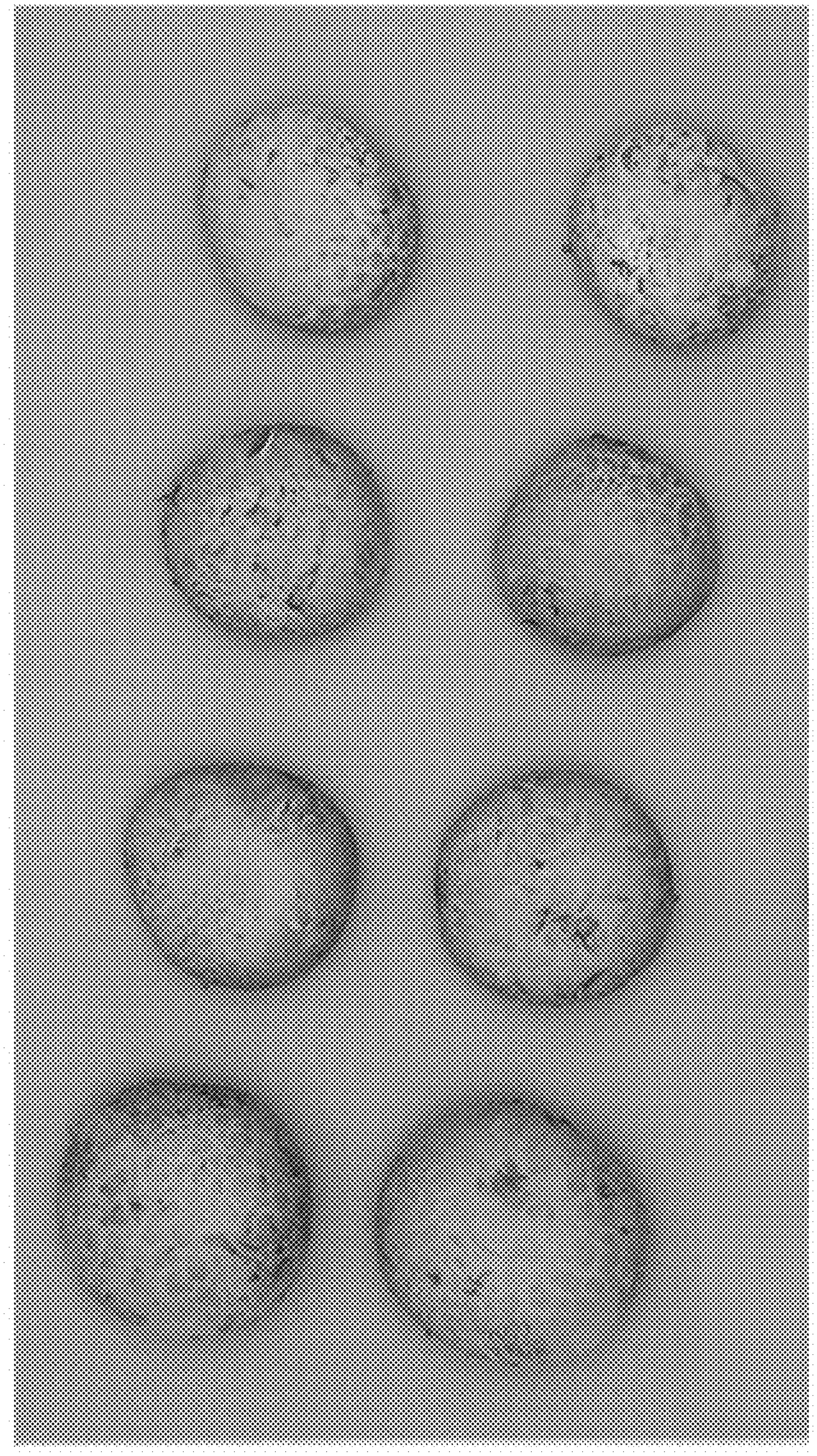
FIG. 7 shows multiple mushroom caps of variety ‘RO14176’ from a top-down view.
Figure 8:
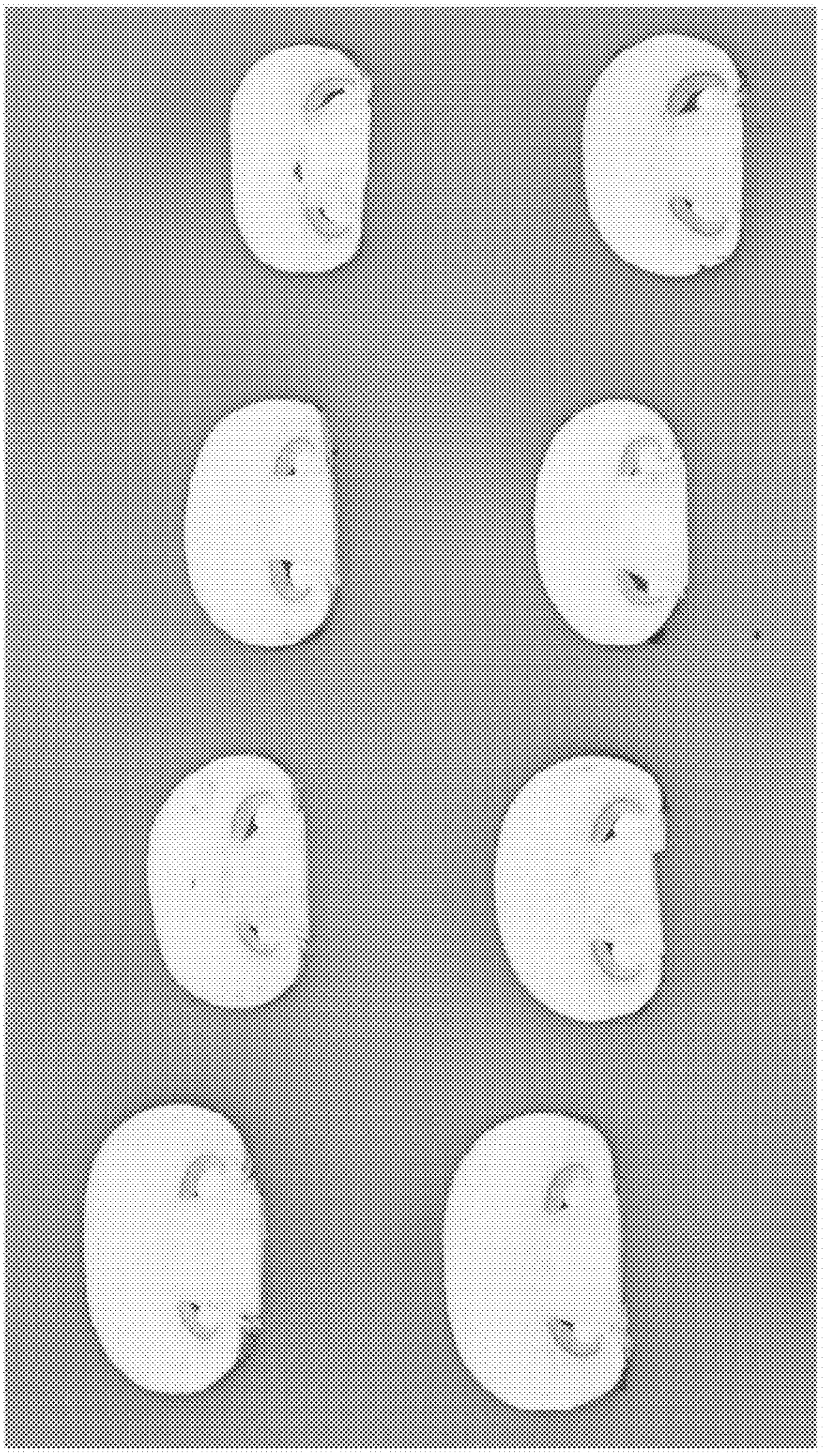
FIG. 8 shows multiple longitudinal slices of mushrooms of variety ‘RO14176’.

FIG. 7 and FIG. 8 show mushroom caps and longitudinal slices, respectively, of strain 'RO14176'.

Comparisons to Commercial Mushroom Varieties

Initial Trials

Tray-Level Comparisons

In further evidence of the distinctness and superiority of mushroom strain 'RO14176', provided below are the results of trials conducted across multiple strains' yielded trays of mushrooms. These trials compare timing for trays to reach pinset and harvestable maturity, tray coverage, cap color darkness, cap firmness, cap roundness (visual), and yield at each break. Characteristics were measured from 46 trays of strain 'RO14176' mushrooms for yield traits and from 26 trays of strain 'RO14176' mushrooms for other traits. Corresponding measurements were taken from 38 trays of strain 'BR06' mushrooms for yield traits and 19 trays of strain 'BR06' mushrooms for other traits (Table 15A and 15B), and corresponding measurements were taken from 17 trays of strain 'B14528' mushrooms (Table 16A and 16B).

Table 15A below provides qualitative comparisons between mushroom strain 'RO14176' and strain 'BR06'. Column 1 lists the tray-level characteristic (as described in Table 1), column 2 shows the qualitative descriptor for the characteristic for mushroom strain 'RO14176' relative to 'BR06', and column 3 shows the qualitative descriptor for mushroom strain 'BR06' relative to 'RO14176'.

TABLE 15A

| Characteristic | 'RO14176' | 'BR06' |
|---|---|---|
| Before First Break | | |
| Days to Pinset | Faster | Slower |
| First Break | | |
| Days to 1st Break | Faster | Slower |
| Tray Coverage | Higher | Lower |
| Cap Color Darkness | Lighter | Darker |
| Cap Firmness | Softer | Firmer |
| Cap Roundness (Visual) | Rounder | Flatter |
| Yield (lb/ft$^2$) | Similar | Similar |
| Second Break | | |
| Days to 2nd Break | Similar | Similar |
| Tray Coverage | Similar | Similar |
| Cap Color Darkness | Lighter | Darker |
| Cap Firmness | Softer | Firmer |
| Cap Roundness (Visual) | Flatter | Rounder |
| Yield (lb/ft$^2$) | Higher | Lower |
| Third Break | | |
| Yield (lb/ft$^2$) | Similar | Similar |
| All Breaks Combined | | |
| Yield (lb/ft$^2$) | Higher | Lower |

Table 15B below provides initial quantitative comparisons between mushroom strain 'RO14176' and strain 'BR06'. Column 1 lists the tray-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate p<0.05.

TABLE 15B

| Characteristic | 'RO14176' Average | 'RO14176' St. Dev. | 'BR06' Average | 'BR06' St. Dev. | p-value |
|---|---|---|---|---|---|
| Before First Break | | | | | |
| Days to Pinset | 11.23 | 0.82 | 12.68 | 1.42 | **8.25E-05** |
| First Break | | | | | |
| Days to 1st Break | 17.46 | 1.03 | 18.53 | 1.71 | **1.27E-02** |
| Tray Coverage | 3.88 | 0.91 | 3.16 | 1.30 | **3.27E-02** |
| Cap Color Darkness | 3.85 | 0.37 | 4.21 | 0.42 | **3.46E-03** |
| Cap Firmness | 3.69 | 0.47 | 4.68 | 0.48 | **1.57E-08** |
| Cap Roundness (Visual) | 3.38 | 0.50 | 2.95 | 0.23 | **9.07E-04** |
| Yield ($lb/ft^2$) | 2.47 | 0.80 | 2.16 | 1.36 | 2.00E-01 |
| Second Break | | | | | |
| Days to 2nd Break | 24.42 | 0.86 | 24.95 | 0.91 | 5.48E-02 |
| Tray Coverage | 3.81 | 0.49 | 3.42 | 1.22 | 1.49E-01 |
| Cap Color Darkness | 3.58 | 0.50 | 4.05 | 0.23 | **4.15E-04** |
| Cap Firmness | 3.81 | 0.40 | 4.44 | 0.51 | **3.61E-05** |
| Cap Roundness (Visual) | 2.69 | 0.47 | 2.94 | 0.24 | **4.24E-02** |
| Yield ($lb/ft^2$) | 1.93 | 0.42 | 1.47 | 0.63 | **1.68E-04** |
| Third Break | | | | | |
| Yield ($lb/ft^2$) | 1.00 | 0.33 | 0.87 | 0.47 | 1.66E-01 |
| All Breaks Combined | | | | | |
| Yield ($lb/ft^2$) | 5.39 | 0.92 | 4.51 | 1.44 | **9.79E-04** |

Table 16A below provides qualitative comparisons between mushroom strain 'RO14176' and strain 'B14528'. Column 1 lists the tray-level characteristic (as described in Table 1), column 2 shows the qualitative descriptor for the characteristic for mushroom strain 'RO14176' relative to 'B14528', and column 3 shows the qualitative descriptor for mushroom strain 'B14528' relative to 'RO14176'.

TABLE 16A

| Characteristic | 'RO14176' | 'B14528' |
|---|---|---|
| Before First Break | | |
| Days to Pinset | Similar | Similar |
| First Break | | |
| Days to 1st Break | Similar | Similar |
| Tray Coverage | Similar | Similar |
| Cap Color Darkness | Similar | Similar |
| Cap Firmness | Similar | Similar |
| Cap Roundness (Visual) | Rounder | Flatter |
| Yield ($lb/ft^2$) | Similar | Similar |
| Second Break | | |
| Days to 2nd Break | Faster | Slower |
| Tray Coverage | Higher | Lower |
| Cap Color Darkness | Similar | Similar |
| Cap Firmness | Similar | Similar |
| Cap Roundness (Visual) | Similar | Similar |
| Yield ($lb/ft^2$) | Similar | Similar |
| Third Break | | |
| Yield ($lb/ft^2$) | Similar | Similar |
| All Breaks Combined | | |
| Yield ($lb/ft^2$) | Similar | Similar |

Table 16B below provides initial quantitative comparisons between mushroom strain 'RO14176' and strain 'B14528'. Column 1 lists the tray-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'B14528', column 5 shows the standard deviation of the characteristic for mushroom strain 'B14528', and column 6 shows the p-values of two-sample, two-sided t-tests. Bolded p-values indicate p<0.05.

TABLE 16B

| Characteristic | 'RO14176' Average | 'RO14176' St. Dev. | 'B14528' Average | 'B14528' St. Dev. | p-value |
|---|---|---|---|---|---|
| Before First Break | | | | | |
| Days to Pinset | 11.23 | 0.82 | 11.41 | 0.87 | 4.92E-01 |
| First Break | | | | | |
| Days to 1st Break | 17.46 | 1.03 | 17.47 | 0.51 | 9.73E-01 |
| Tray Coverage | 3.88 | 0.91 | 3.59 | 0.87 | 2.94E-01 |
| Cap Color Darkness | 3.85 | 0.37 | 3.82 | 0.39 | 8.49E-01 |
| Cap Firmness | 3.69 | 0.47 | 3.88 | 0.33 | 1.56E-01 |
| Cap Roundness (Visual) | 3.38 | 0.50 | 2.88 | 0.33 | **7.05E-04** |
| Yield ($lb/ft^2$) | 2.47 | 0.80 | 2.39 | 0.54 | 7.11E-01 |
| Second Break | | | | | |
| Days to 2nd Break | 24.42 | 0.86 | 25.12 | 0.86 | **1.30E-02** |
| Tray Coverage | 3.81 | 0.49 | 3.47 | 0.51 | **3.67E-02** |
| Cap Color Darkness | 3.58 | 0.50 | 3.76 | 0.56 | 2.60E-01 |
| Cap Firmness | 3.81 | 0.40 | 3.82 | 0.39 | 8.99E-01 |
| Cap Roundness (Visual) | 2.69 | 0.47 | 2.82 | 0.39 | 3.47E-01 |
| Yield ($lb/ft^2$) | 1.93 | 0.42 | 1.74 | 0.38 | 1.09E-01 |
| Third Break | | | | | |
| Yield ($lb/ft^2$) | 1.00 | 0.33 | 1.18 | 0.38 | 6.16E-02 |
| All Breaks Combined | | | | | |
| Yield ($lb/ft^2$) | 5.39 | 0.92 | 5.31 | 0.76 | 7.45E-01 |

Individual Mushroom-Level Comparisons

In additional evidence of the distinctness and superiority of mushroom strain 'RO14176', provided below is a summary of precise quantitative measurements of individual mushrooms at first and second breaks. These data compare Cap L* Value, Cap a* Value, and Cap b* Values in the International Commission on Illumination (CIELAB) color space, Cap Diameter, Cap Height, Cap Flesh Thickness, Stipe Diameter, Relative Cap Height, Relative Cap Flesh Thickness, and Relative Stipe Diameter (as described in Table 1). Measurements from 210 first break and 130 second break 'RO14176' mushrooms were compared to 350 first break and 130 second break 'BR06' mushrooms (Tables 17A and 17B) and 90 first break and 40 second break 'B14528' mushrooms (Tables 18A and 18B).

Table 17A below provides qualitative comparisons between mushroom strain 'RO14176' and strain 'BR06'. Column 1 lists the mushroom-level characteristics (as described in Table 1), column 2 shows the qualitative descriptor for the characteristic for mushroom strain 'RO14176' relative to 'BR06', and column 3 shows the qualitative descriptor for mushroom strain 'BR06' relative to 'RO14176'.

TABLE 17A

| Characteristic | 'RO14176' | 'BR06' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Larger | Smaller |
| Cap Height | Taller | Shorter |
| Cap Flesh Thickness | Thicker | Thinner |
| Stipe Diameter | Larger | Smaller |
| Relative Cap Height | Taller | Shorter |
| Relative Cap Flesh Thickness | Thicker | Thinner |
| Relative Stipe Diameter | Similar | Similar |
| Second Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Smaller | Larger |
| Cap Height | Similar | Similar |
| Cap Flesh Thickness | Thicker | Thinner |
| Stipe Diameter | Smaller | Larger |
| Relative Cap Height | Taller | Shorter |
| Relative Cap Flesh Thickness | Thicker | Thinner |
| Relative Stipe Diameter | Smaller | Larger |

Table 17B below provides initial quantitative comparisons between mushroom strain 'RO14176' and strain 'BR06'. Column 1 lists the mushroom-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate $p<0.05$.

TABLE 17B

| | 'RO14176' | | 'BR06' | | |
|---|---|---|---|---|---|
| Characteristic | Average | St. Dev. | Average | St. Dev. | p-value |
| First Break | | | | | |
| Cap L* Value (dark-light) | 65.73 | 4.23 | 63.49 | 6.52 | **1.00E−05** |
| Cap a* Value (green-red) | 7.64 | 1.00 | 8.53 | 1.85 | **2.45E−10** |
| Cap b* Value (blue-yellow) | 26.84 | 1.43 | 28.15 | 2.48 | **7.83E−12** |
| Cap Diameter | 43.93 | 3.61 | 42.78 | 4.41 | **1.45E−03** |
| Cap Height | 28.15 | 2.18 | 25.75 | 2.35 | **1.27E−29** |
| Cap Flesh Thickness | 15.37 | 1.96 | 13.25 | 1.46 | **1.88E−44** |
| Stipe Diameter | 19.92 | 2.43 | 19.25 | 2.47 | **1.19E−03** |
| Relative Cap Height | 0.64 | 0.03 | 0.60 | 0.04 | **4.25E−33** |
| Relative Cap Flesh Thickness | 0.35 | 0.04 | 0.31 | 0.03 | **3.34E−39** |
| Relative Stipe Diameter | 0.45 | 0.05 | 0.45 | 0.06 | 5.18E−01 |
| Second Break | | | | | |
| Cap L* Value (dark-light) | 68.87 | 3.95 | 64.27 | 3.81 | **5.37E−20** |
| Cap a* Value (green-red) | 6.66 | 0.95 | 8.20 | 1.14 | **1.67E−27** |
| Cap b* Value (blue-yellow) | 26.77 | 1.64 | 28.31 | 1.65 | **1.08E−13** |
| Cap Diameter | 42.13 | 3.35 | 43.26 | 4.15 | **1.32E−02** |
| Cap Height | 26.36 | 2.27 | 25.80 | 2.61 | 5.55E−02 |
| Cap Flesh Thickness | 14.15 | 1.77 | 13.46 | 1.52 | **6.12E−04** |
| Stipe Diameter | 17.80 | 2.58 | 18.97 | 3.67 | **2.54E−03** |
| Relative Cap Height | 0.63 | 0.05 | 0.60 | 0.04 | **1.01E−07** |
| Relative Cap Flesh Thickness | 0.34 | 0.04 | 0.31 | 0.03 | **1.18E−07** |
| Relative Stipe Diameter | 0.42 | 0.05 | 0.44 | 0.08 | **3.93E−02** |

Table 18A below provides qualitative comparisons between mushroom strain 'RO14176' and strain 'B14528'. Column 1 lists the mushroom-level characteristics (as described in Table 1), column 2 shows the qualitative descriptor for the characteristic for mushroom strain 'RO14176' relative to 'B14528', and column 3 shows the qualitative descriptor for mushroom strain 'B14528' relative to 'RO14176'.

TABLE 18A

| Characteristic | 'RO14176' | 'B14528' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Similar | Similar |
| Cap Height | Taller | Shorter |
| Cap Flesh Thickness | Thicker | Thinner |
| Stipe Diameter | Larger | Smaller |
| Relative Cap Height | Taller | Shorter |
| Relative Cap Flesh Thickness | Thicker | Thinner |
| Relative Stipe Diameter | Larger | Smaller |
| Second Break | | |
| Cap L* Value (dark-light) | Similar | Similar |
| Cap a* Value (green-red) | Greener | Redder |
| Cap b* Value (blue-yellow) | Bluer | Yellower |
| Cap Diameter | Smaller | Larger |
| Cap Height | Similar | Similar |
| Cap Flesh Thickness | Thicker | Thinner |
| Stipe Diameter | Similar | Similar |
| Relative Cap Height | Taller | Shorter |
| Relative Cap Flesh Thickness | Thicker | Thinner |
| Relative Stipe Diameter | Similar | Similar |

Table 18B below provides initial quantitative comparisons between mushroom strain 'RO14176' and strain 'B14528'. Column 1 lists the mushroom-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'B14528', column 5 shows the standard deviation of the characteristic for mushroom strain 'B14528', and column 6 shows the p-values of two-sample, two-sided t-tests. Bolded p-values indicate $p<0.05$.

TABLE 18B

| | 'RO14176' | | 'B14528' | | |
|---|---|---|---|---|---|
| Characteristic | Average | St. Dev. | Average | St. Dev. | p-value |
| First Break | | | | | |
| Cap L* Value (dark-light) | 65.73 | 4.23 | 64.48 | 5.25 | **2.98E−02** |
| Cap a* Value (green-red) | 7.64 | 1.00 | 8.03 | 1.65 | **1.30E−02** |
| Cap b* Value (blue-yellow) | 26.84 | 1.43 | 29.38 | 1.50 | **3.68E−34** |
| Cap Diameter | 43.93 | 3.61 | 43.84 | 3.80 | 8.49E−01 |
| Cap Height | 28.15 | 2.18 | 26.60 | 1.97 | **1.91E−08** |
| Cap Flesh Thickness | 15.37 | 1.96 | 12.91 | 0.93 | **2.05E−27** |
| Stipe Diameter | 19.92 | 2.43 | 17.58 | 1.44 | **3.66E−17** |
| Relative Cap Height | 0.64 | 0.03 | 0.61 | 0.03 | **1.59E−15** |
| Relative Cap Flesh Thickness | 0.35 | 0.04 | 0.30 | 0.03 | **2.71E−28** |
| Relative Stipe Diameter | 0.45 | 0.05 | 0.40 | 0.04 | **2.36E−18** |
| Second Break | | | | | |
| Cap L* Value (dark-light) | 68.87 | 3.95 | 68.52 | 4.46 | 6.36E−01 |
| Cap a* Value (green-red) | 6.66 | 0.95 | 7.88 | 1.49 | **7.36E−09** |
| Cap b* Value (blue-yellow) | 26.77 | 1.64 | 28.55 | 1.65 | **1.30E−08** |
| Cap Diameter | 42.13 | 3.35 | 44.86 | 3.59 | **1.67E−05** |
| Cap Height | 26.36 | 2.27 | 26.29 | 1.72 | 8.51E−01 |

TABLE 18B-continued

| Characteristic | 'RO14176' Average | 'RO14176' St. Dev. | 'B14528' Average | 'B14528' St. Dev. | p-value |
|---|---|---|---|---|---|
| Cap Flesh Thickness | 14.15 | 1.77 | 12.60 | 1.32 | **8.12E-07** |
| Stipe Diameter | 17.80 | 2.58 | 18.11 | 3.29 | 5.33E-01 |
| Relative Cap Height | 0.63 | 0.05 | 0.59 | 0.04 | **1.36E-05** |
| Relative Cap Flesh Thickness | 0.34 | 0.04 | 0.28 | 0.03 | **9.66E-13** |
| Relative Stipe Diameter | 0.42 | 0.05 | 0.40 | 0.07 | 9.03E-02 |

Additional Trials

Tray-Level Comparisons

Several additional trials were conducted for characterizing 'RO14176'. In further evidence of the distinctness and superiority of mushroom strain 'RO14176', provided below are the results of trials conducted across multiple strains' yielded trays of mushrooms. These trials compare timing for trays to reach pinset and harvestable maturity, and yield at each break.

Table 19A below provides qualitative comparisons between mushroom strain 'RO14176' and strain 'BR06'. Traits of particular interest are bolded. Column 1 lists the tray-level characteristic (as described in Table 1), column 2 shows the qualitative descriptor for the characteristic for mushroom strain 'RO14176' relative to 'BR06', and column 3 shows the qualitative descriptor for mushroom strain 'BR06' relative to 'RO14176'.

TABLE 19A

| Characteristic | 'RO14176' | 'BR06' |
|---|---|---|
| Before First Break | | |
| Days to Pinset | Faster | Slower |
| First Break | | |
| Days to 1st Break | Faster | Slower |
| Percent Harvested Speed | Faster | Slower |
| Yield (kg/m$^2$) | Similar | Similar |
| Second Break | | |
| Days to 2nd Break | Faster | Slower |
| Yield (kg/m$^2$) | Similar | Similar |
| Third Break | | |
| Yield (kg/m$^2$) | Higher | Lower |
| All Breaks Combined | | |
| Yield (kg/m$^2$) | Higher | Lower |

Table 19B below provides further quantitative comparisons between mushroom strain 'RO14176' and strain 'BR06'.

The first part of analyzing trait measurements in the additional trials herein included making comparisons between all three of instant strain 'RO14176', comparative strain 'BR06', and comparative strain 'B14528'. For these three strains, a Shapiro-Wilk test and a Levene test were performed first to assess if the data satisfy the assumptions of normality and equal variances among groups, respectively, of a standard ANOVA. The Shapiro-Wilk test and Levene test determined that most of these traits satisfied neither assumption. Therefore, a Kruskal-Wallis test (Kruskal, W. H., & Wallis, W. A. (1952). Use of ranks in one-criterion variance analysis. Journal of the American statistical Association, 47(260), 583-621), a non-parametric variation of ANOVA that does not assume normality, equal variances among groups, or equal sample sizes among groups, was performed. Medians and interquartile ranges (IQR) were reported, as these metrics are robust to non-normal distributions. Means are also reported for consistency with normally-distributed traits.

The Shapiro-Wilk test and Levene test determined that most developmental timing traits (Days to Pinset, Days to 1st Break, and Days to 2nd Break) and yield traits were not normally distributed and variances among groups were not equal. The Kruskal-Wallis test and Dunn post-hoc test ("Dunn's Test"; Dunn, O. J. (1964). Multiple comparisons using rank sums. Technometrics, 6(3), 241-252) were used in these cases. When the Kruskal-Wallis test results were significant based on a threshold of $p<0.05$, Dunn's test was performed post-hoc to make pairwise strain comparisons (Dunn, 1964). P-values were adjusted using the Bonferroni correction to minimize risk of Type 1 error (false significance). An exception to this trend was Percent Harvested Speed, which was normally distributed and exhibited equal variance for all strains. For assessing Percent Harvested Speed, a standard ANOVA was used and a Tukey Honestly Significant Difference (HSD) test was performed post-hoc for pairwise strain comparisons. Standard deviations multiplied by 100 for consistency alongside percentages ("SD*100") were reported for this trait. This testing was performed on groups of three strains, but the results show a pairwise subset of the tests for consistency with the initial trials.

In Table 19B, column 1 shows each trait and the strains compared for said trait, column 2 shows the mean value for that strain's measurements of that trait, column 3 shows the median value of the same measurements, column 4 shows the interquartile range ("IQR") for the same measurements, column 5 shows the number of trials conducted, and column 6 shows the statistical significance group calculated for that strain for that trait according to Dunn's Test. Traits of particular interest are bolded.

TABLE 19B

| Variety | Mean | Median | IQR | Number of Trials | Significance Group (Dunn's Test) |
|---|---|---|---|---|---|
| Before First Break<br>Days to Pinset | | | | | |
| 'RO14176' | 11.4 | 12.0 | 1.00 | 7 | a |
| 'BR06' | 12.7 | 12.5 | 1.00 | 7 | b |
| First Break<br>Days to 1st Break | | | | | |
| 'RO14176' | 17.7 | 18.0 | 1.00 | 7 | a |
| 'BR06' | 18.8 | 18.0 | 2.00 | 7 | b |
| Yield (kg/m$^2$) | | | | | |
| 'RO14176' | 12.40 | 12.25 | 4.69 | 6 | a |
| 'BR06' | 10.99 | 11.03 | 8.10 | 6 | a |
| Second Break<br>Days to 2nd Break | | | | | |
| 'RO14176' | 25.3 | 25.0 | 2.00 | 7 | a |
| 'BR06' | 25.9 | 26.0 | 2.00 | 7 | b |
| Yield (kg/m$^2$) | | | | | |
| 'RO14176' | 8.45 | 8.50 | 3.52 | 6 | a |
| 'BR06' | 7.37 | 6.59 | 5.13 | 6 | a |
| Third Break<br>Yield (kg/m$^2$) | | | | | |
| 'RO14176' | 4.20 | 3.71 | 2.69 | 6 | a |
| 'BR06' | 3.27 | 2.34 | 3.03 | 6 | b |

TABLE 19B-continued

| | | | | | |
|---|---|---|---|---|---|
| All Breaks Combined Yield (kg/m$^2$) | | | | | |
| 'RO14176' | 25.05 | 23.88 | 3.66 | 6 | a |
| 'BR06' | 21.58 | 22.02 | 4.39 | 6 | b |
| Percent Harvested Speed (measured in First Break) | | | SD * 100 | | Significance Group (Tukey HSD) |
| 'RO14176' | 38.7% | 39.9% | 13.10 | 5 | b |
| 'BR06' | 14.5% | 12.9% | 16.90 | 5 | a |

Table 20A below provides qualitative comparisons between mushroom strain 'RO14176' and strain 'B14528'. Traits of particular interest are bolded. Column 1 lists the tray-level characteristic (as described in Table 1), column 2 shows the qualitative descriptor for the characteristic for mushroom strain 'RO14176' relative to 'B14528', and column 3 shows the qualitative descriptor for mushroom strain 'B14528' relative to 'RO14176'.

TABLE 20A

| Characteristic | 'RO14176' | 'B14528' |
|---|---|---|
| Before First Break | | |
| Days to Pinset | Similar | Similar |
| First Break | | |
| Days to 1st Break | Similar | Similar |
| Percent Harvested Speed | Similar | Similar |
| Yield (kg/m$^2$) | Similar | Similar |
| Second Break | | |
| Days to 2nd Break | Similar | Similar |
| Yield (kg/m$^2$) | Similar | Similar |
| Third Break | | |
| Yield (kg/m$^2$) | Similar | Similar |
| All Breaks Combined | | |
| Yield (kg/m$^2$) | Similar | Similar |

Table 20B below provides additional quantitative comparison between mushroom strain 'RO14176' and strain 'B14528'. Column 1 shows the strains compared for each trait, column 2 shows the mean value for that strain's measurements, column 3 shows the median value of the same measurements, column 4 shows either the interquartile range ("IQR") or the standard deviation multiplied by 100 for consistency alongside percentages ("SD*100") for the same measurements, column 5 shows the number of trials conducted, and column 6 shows the statistical significance group calculated for that strain for that trait according to either Dunn's Test or Tukey HSD.

TABLE 20B

| Characteristic | Mean | Median | IQR | Number of Trials | Significance Group (Dunn's Test) |
|---|---|---|---|---|---|
| Before First Break Days to Pinset | | | | | |
| 'RO14176' | 11.4 | 12.0 | 1.00 | 7 | a |
| 'B14528' | 11.2 | 11.0 | 1.50 | 7 | a |
| First Break Days to 1st Break | | | | | |
| 'RO14176' | 17.7 | 18.0 | 1.00 | 7 | a |
| 'B14528' | 17.6 | 18.0 | 1.00 | 7 | a |
| Yield (kg/m$^2$) | | | | | |
| 'RO14176' | 12.40 | 12.25 | 4.69 | 6 | a |
| 'B14528' | 11.91 | 12.21 | 4.35 | 6 | a |
| Second Break Days to 2nd Break | | | | | |
| 'RO14176' | 25.3 | 25.0 | 2.00 | 7 | a |
| 'B14528' | 25.5 | 25.0 | 1.00 | 7 | ab |
| Yield (kg/m$^2$) | | | | | |
| 'RO14176' | 8.45 | 8.50 | 3.52 | 6 | a |
| 'B14528' | 7.47 | 7.76 | 2.93 | 6 | a |
| Third Break Yield (kg/m$^2$) | | | | | |
| 'RO14176' | 4.20 | 3.71 | 2.69 | 6 | a |
| 'B14528' | 4.49 | 3.95 | 2.59 | 6 | a |
| All Breaks Combined Yield (kg/m$^2$) | | | | | |
| 'RO14176' | 25.05 | 23.88 | 3.66 | 6 | a |
| 'B14528' | 23.88 | 23.97 | 6.69 | 6 | a |
| Percent Harvested Speed (measured in First Break) | Mean | Median | SD * 100 | | Significance Group (Tukey HSD) |
| 'RO14176' | 38.7% | 39.9% | 13.10 | 5 | b |
| 'B14528' | 41.8% | 40.3% | 7.60 | 5 | b |

Individual Mushroom-Level Comparisons

In additional evidence of the distinctness and superiority of mushroom strain 'RO14176', provided below is a summary of precise quantitative measurements of individual mushrooms at first and second breaks. These data compare Cap L* Value, Cap a* Value, and Cap b* Values in the International Commission on Illumination (CIELAB) color space, Cap Apex Flesh Thickness, Cap Edge Flesh Thickness, and Cap Roundness (Calculated) (as described in Table 1). Measurements were taken for hundreds of mushrooms per trait, noted as sample size (n) in Tables 21B and 22B.

Table 21A below provides qualitative comparisons between mushroom strain 'RO14176' and strain 'BR06'. Traits of particular interest are bolded. Column 1 lists the mushroom-level characteristics (as described in Table 1), column 2 shows the qualitative descriptor for the characteristic for mushroom strain 'RO14176' relative to 'BR06', and column 3 shows the qualitative descriptor for mushroom strain 'BR06' relative to 'RO14176'.

TABLE 21A

| Characteristic | 'RO14176' | 'BR06' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |
| Cap Edge Flesh Thickness | Thicker | Thinner |
| Cap Roundness (Calculated) | Rounder | Flatter |
| Second Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |

TABLE 21A-continued

| Characteristic | 'RO14176' | 'BR06' |
|---|---|---|
| Cap Edge Flesh Thickness | Thicker | Thinner |
| Cap Roundness (Calculated) | Rounder | Flatter |

Table 21B below provides additional quantitative comparisons between mushroom strain 'RO14176' and strain 'BR06'. Column 1 shows each trait and the strains compared for said trait, column 2 shows the mean value for that strain's measurements of that trait, column 3 shows the median value of the same measurements, column 4 shows the interquartile range ("IQR") for the same measurements, column 5 shows the number of mushrooms assessed (n), and column 6 shows the statistical significance group calculated for that strain for that trait according to Dunn's Test.

TABLE 21B

| Variety | Mean | Median | IQR | Number of Mushrooms (n) | Significance Group (Dunn's Test) |
|---|---|---|---|---|---|
| First Break | | | | | |
| Cap L* Value (dark-light) | | | | | |
| 'RO14176' | 65.76 | 65.82 | 5.82 | 469 | a |
| 'BR06' | 63.30 | 62.74 | 9.83 | 797 | b |
| Cap a* Value (green-red) | | | | | |
| 'RO14176' | 7.45 | 7.47 | 1.58 | 469 | a |
| 'BR06' | 8.67 | 8.96 | 2.58 | 787 | b |
| Cap b* Value (blue-yellow) | | | | | |
| 'RO14176' | 28.17 | 28.03 | 2.64 | 469 | a |
| 'BR06' | 28.72 | 29.04 | 3.17 | 776 | b |
| Cap Apex Flesh Thickness | | | | | |
| 'RO14176' | 0.54 | 0.54 | 0.06 | 453 | a |
| 'BR06' | 0.52 | 0.52 | 0.05 | 541 | b |
| Cap Edge Flesh Thickness | | | | | |
| 'RO14176' | 0.27 | 0.26 | 0.07 | 449 | a |
| 'BR06' | 0.21 | 0.21 | 0.09 | 537 | b |
| Cap Roundness (Calculated) | | | | | |
| 'RO14176' | 0.64 | 0.64 | 0.05 | 453 | a |
| 'BR06' | 0.61 | 0.61 | 0.04 | 541 | b |
| Second Break | | | | | |
| Cap L* Value (dark-light) | | | | | |
| 'RO14176' | 68.92 | 68.86 | 6.39 | 263 | a |
| 'BR06' | 65.68 | 65.49 | 5.90 | 340 | b |
| Cap a* Value (green-red) | | | | | |
| 'RO14176' | 6.37 | 6.43 | 1.60 | 261 | a |
| 'BR06' | 7.21 | 7.31 | 2.42 | 340 | b |
| Cap b* Value (blue-yellow) | | | | | |
| 'RO14176' | 27.36 | 27.35 | 2.11 | 261 | a |
| 'BR06' | 28.15 | 28.49 | 2.86 | 340 | b |
| Cap Apex Flesh Thickness | | | | | |
| 'RO14176' | 0.54 | 0.54 | 0.04 | 235 | a |
| 'BR06' | 0.51 | 0.52 | 0.07 | 362 | b |
| Cap Edge Flesh Thickness | | | | | |
| 'RO14176' | 0.31 | 0.31 | 0.06 | 235 | a |
| 'BR06' | 0.23 | 0.23 | 0.09 | 362 | b |
| Cap Roundness (Calculated) | | | | | |
| 'RO14176' | 0.61 | 0.60 | 0.05 | 235 | a |
| 'BR06' | 0.60 | 0.59 | 0.06 | 363 | b |

Table 22A below provides qualitative comparisons between mushroom strain 'RO14176' and strain 'B14528'. Column 1 lists the mushroom-level characteristics (as described in Table 1), column 2 shows the qualitative descriptor for the characteristic for mushroom strain 'RO14176' relative to 'B 14528', and column 3 shows the qualitative descriptor for mushroom strain 'B14528' relative to 'RO14176'.

TABLE 22A

| Characteristic | 'RO14176' | 'B14528' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |
| Cap Edge Flesh Thickness | Thicker | Thinner |
| Cap Roundness (Calculated) | Rounder | Flatter |
| Second Break | | |
| Cap L* Value (dark-light) | Similar | Similar |
| Cap a* Value (green-red) | Redder | Greener |
| Cap b* Value (blue-yellow) | Similar | Similar |
| Cap Apex Flesh Thickness | Thicker | Thinner |
| Cap Edge Flesh Thickness | Thicker | Thinner |
| Cap Roundness (Calculated) | Rounder | Flatter |

Table 22B shows additional quantitative comparisons between mushroom strain 'RO14176' and strain 'B14528'. Column 1 shows each trait and the strains compared for said trait, column 2 shows the mean value for that strain's measurements of that trait, column 3 shows the median value of the characteristic, column 4 shows the interquartile range (IQR) for the characteristic, column 5 shows the number of mushrooms assessed (n), and column 6 shows the statistical significance group calculated according to Dunn's Test.

TABLE 22B

| Variety | Mean | Median | IQR | Number of Mushrooms (n) | Significance Group (Dunn's Test) |
|---|---|---|---|---|---|
| First Break | | | | | |
| Cap L* Value (dark-light) | | | | | |
| 'RO14176' | 65.76 | 65.82 | 5.82 | 469 | a |
| 'B14528' | 64.06 | 64.13 | 6.56 | 340 | c |
| Cap a* Value (green-red) | | | | | |
| 'RO14176' | 7.45 | 7.47 | 1.58 | 469 | a |
| 'B14528' | 8.26 | 8.31 | 2.13 | 340 | c |
| Cap b* Value (blue-yellow) | | | | | |
| 'RO14176' | 28.17 | 28.03 | 2.64 | 469 | a |
| 'B14528' | 30.31 | 30.16 | 3.39 | 340 | c |
| Cap Apex Flesh Thickness | | | | | |
| 'RO14176' | 0.54 | 0.54 | 0.06 | 453 | a |
| 'B14528' | 0.47 | 0.46 | 0.06 | 387 | c |
| Cap Edge Flesh Thickness | | | | | |
| 'RO14176' | 0.27 | 0.26 | 0.07 | 449 | a |
| 'B14528' | 0.22 | 0.22 | 0.08 | 387 | b |
| Cap Roundness (Calculated) | | | | | |
| 'RO14176' | 0.64 | 0.64 | 0.05 | 455 | a |
| 'B14528' | 0.61 | 0.61 | 0.05 | 389 | b |
| Second Break | | | | | |
| Cap L* Value (dark-light) | | | | | |
| 'RO14176' | 68.92 | 68.86 | 6.39 | 263 | a |
| 'B14528' | 68.56 | 69.02 | 6.54 | 170 | a |

TABLE 22B-continued

| Variety | Mean | Median | IQR | Number of Mushrooms (n) | Significance Group (Dunn's Test) |
|---|---|---|---|---|---|
| Cap a* Value (green-red) | | | | | |
| 'RO14176' | 6.37 | 6.43 | 1.60 | 261 | a |
| 'B14528' | 6.09 | 5.96 | 2.05 | 170 | c |
| Cap b* Value (blue-yellow) | | | | | |
| 'RO14176' | 27.36 | 27.35 | 2.11 | 261 | a |
| 'B14528' | 27.37 | 27.78 | 3.22 | 170 | a |
| Cap Apex Flesh Thickness | | | | | |
| 'RO14176' | 0.54 | 0.54 | 0.04 | 235 | a |
| 'B14528' | 0.46 | 0.46 | 0.05 | 198 | c |
| Cap Edge Flesh Thickness | | | | | |
| 'RO14176' | 0.31 | 0.31 | 0.06 | 235 | a |
| 'B14528' | 0.23 | 0.23 | 0.06 | 198 | b |
| Cap Roundness (Calculated) | | | | | |
| 'RO14176' | 0.61 | 0.60 | 0.05 | 235 | a |
| 'B14528' | 0.60 | 0.60 | 0.05 | 198 | b |

One of the advantages of the strain 'RO14176' is its incompatibility with other commercial strains. Table 23 below provides results of compatibility tests between strain 'RO14176' and commercial strain 'BR16', commercial strain 'B14528', or related strain 'RO10425'. These results indicate that strain 'RO14176' is incompatible with strain 'BR06' and strain 'B14528', and compatible with related strain 'RO10425'. This was true regardless of which tested strain served as the compost variety and which tested strain served as the casing variety.

TABLE 23

| Strains (compost variety/ | Mean | | Median | | SD | | | Significance |
|---|---|---|---|---|---|---|---|---|
| casing variety) | lb/ft$^2$ | kg/m$^2$ | lb/ft$^2$ | kg/m$^2$ | lb/ft$^2$ | kg/m$^2$ | Trials | Group |
| RO14176'/'RO14176' | 2.66 | 12.99 | 2.41 | 11.77 | 0.61 | 2.98 | 3 | a |
| RO10425'/'RO10425' | 2.71 | 13.23 | 2.86 | 13.94 | 0.50 | 2.44 | 3 | a |
| BR06'/'BR06' | 2.62 | 12.79 | 2.46 | 11.99 | 1.15 | 5.61 | 2 | a |
| B14528'/'B14528' | 2.93 | 14.31 | 2.92 | 14.23 | 0.34 | 1.66 | 1 | a |
| RO10425'/'RO14176', 'RO14176'/'RO10425' | 2.43 | 11.86 | 2.75 | 13.40 | 0.77 | 3.76 | 1 | a |
| RO14176'/'BR06', 'BR06'/'RO14176' | 1.19 | 5.81 | 1.20 | 5.86 | 0.37 | 1.81 | 1 | b |
| RO14176'/'B14528', 'B14528'/'RO14176' | 0.70 | 3.42 | 0.76 | 3.69 | 0.21 | 1.03 | 1 | b |

Example 3: Characterization of 'RO12756'

The following example describes the characterization of strain 'RO12756' compared to commercial varieties.

Methodology

The measurements and calculations were conducted as in Example 1.

Results

Objective Description of the Variety 'RO12756'

The following detailed description sets forth the breeding procedures and the characteristics of new cultivar designated 'RO12756'. The strain is maintained and propagated as vegetative mycelium. Spawn (inoculum for the substrate compost) is prepared from the vegetative mycelium. The new variety was tested on a scale of hundreds of individual mushrooms. The variety has shown uniformity and stability for the traits, within the limits of environmental influence for the traits.

All homokaryons utilized are strains of *Agaricus bisporus*.

In a first cross, a bridging cross strain 4×29 slow grower (sg) was crossed with a commercial off-white hybrid strain protoplast.

'RO12756' was produced through the cross of a homokaryon SSI of the first cross to a homokaryon SSI of strain 'RO10425'.

'RO12756' sets pins and produces harvestable mushrooms as fast or faster than available brown commercial strains. 'RO12756' also exhibits high tray coverage, high yield, a desirably light brown cap color, medium firmness, and thick stipes and cap flesh relative to cap diameter. 'RO12756' additionally exhibits rounder cap shape, thicker cap apex flesh, thicker cap edge flesh, and percent harvested speed faster or as fast as other available brown commercial strains.

Other characteristics of 'RO12756' distinguishable from other varieties are described below (compared to commercial line 'BR06' and commercial line 'B14528').

Comparisons to Commercial Mushroom Varieties

Initial Trials

Tray-Level Comparisons

In further evidence of the distinctness and superiority of mushroom strain 'RO12756', provided below are the results of trials conducted across multiple strains' yielded trays of mushrooms. These trials compare timing for trays to reach pinset and harvestable maturity, tray coverage, cap color darkness, cap firmness, cap roundness (visual), yield at each break, and percentage of each break's yield harvested by 17 days post-casing (1st break), 24 days post-casing (2nd break), and 32 days post-casing (3rd break). Characteristics were measured from 74-147 trays of strain 'RO12756' mushrooms with corresponding measurements taken of 94-166 trays of strain 'BR06' mushrooms (Table 24A and 24B) and 12-28 trays of strain 'B14528' mushrooms (Table 25A and 25B). Percent Harvest Speed characteristics were measured for 34-36 trials containing strain 'RO12756', 33-36 trials containing strain 'BR06', and 3-4 trials containing strain 'B14528'.

Figure 4:
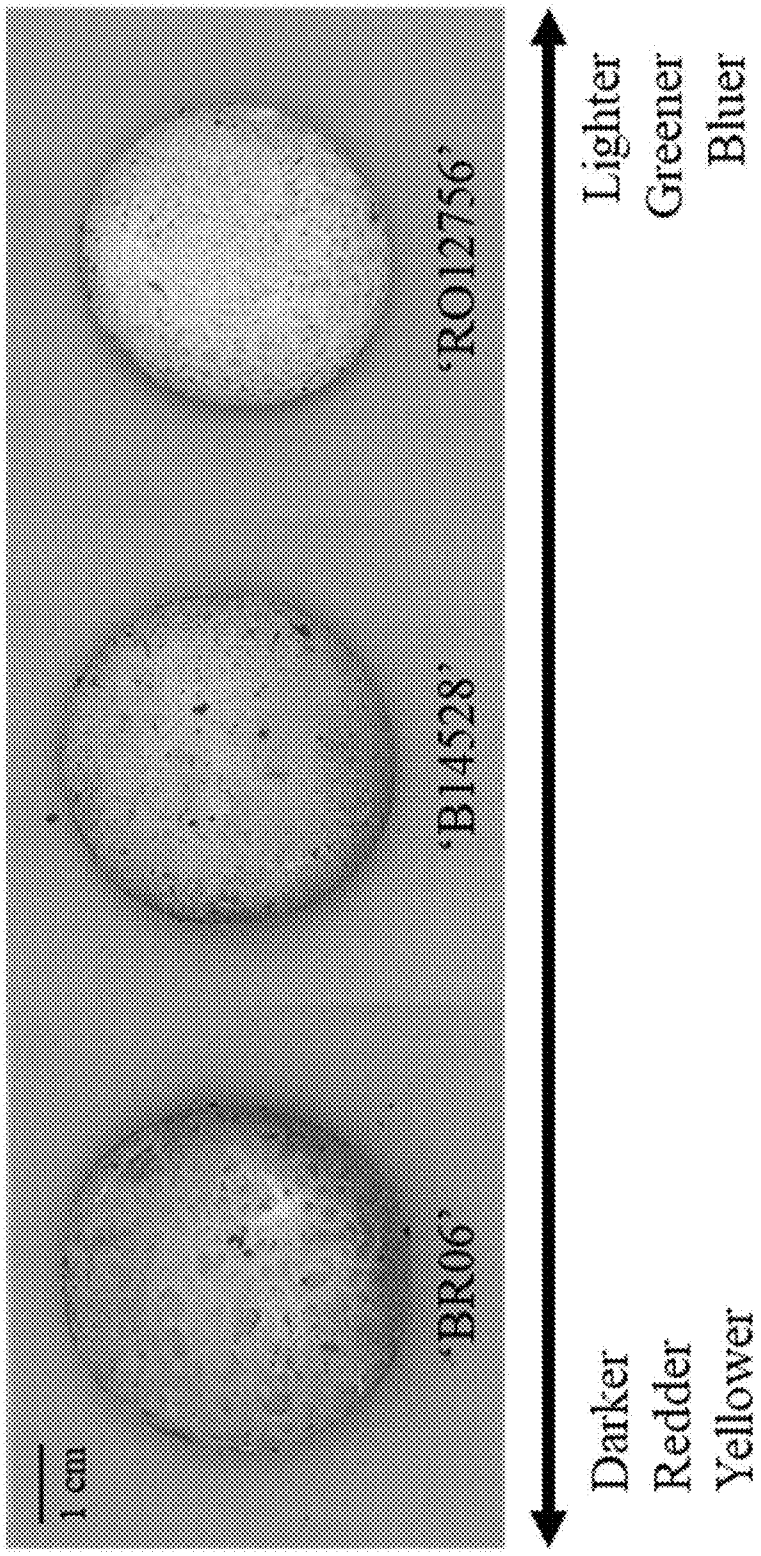
FIG. 4 shows a representative comparison of cap colors for variety 'BR06' (left), variety 'B14528' (center), and variety 'RO12756' (right) cap colors based on Cap L* Value, Cap a* Value, and Cap b* Value at first break. Mushrooms pictured were grown in the same room, under the same environmental conditions, and were harvested from the same trial in May 2025. All photos have the same scale. Scale bar=1 cm.
Figure 5:
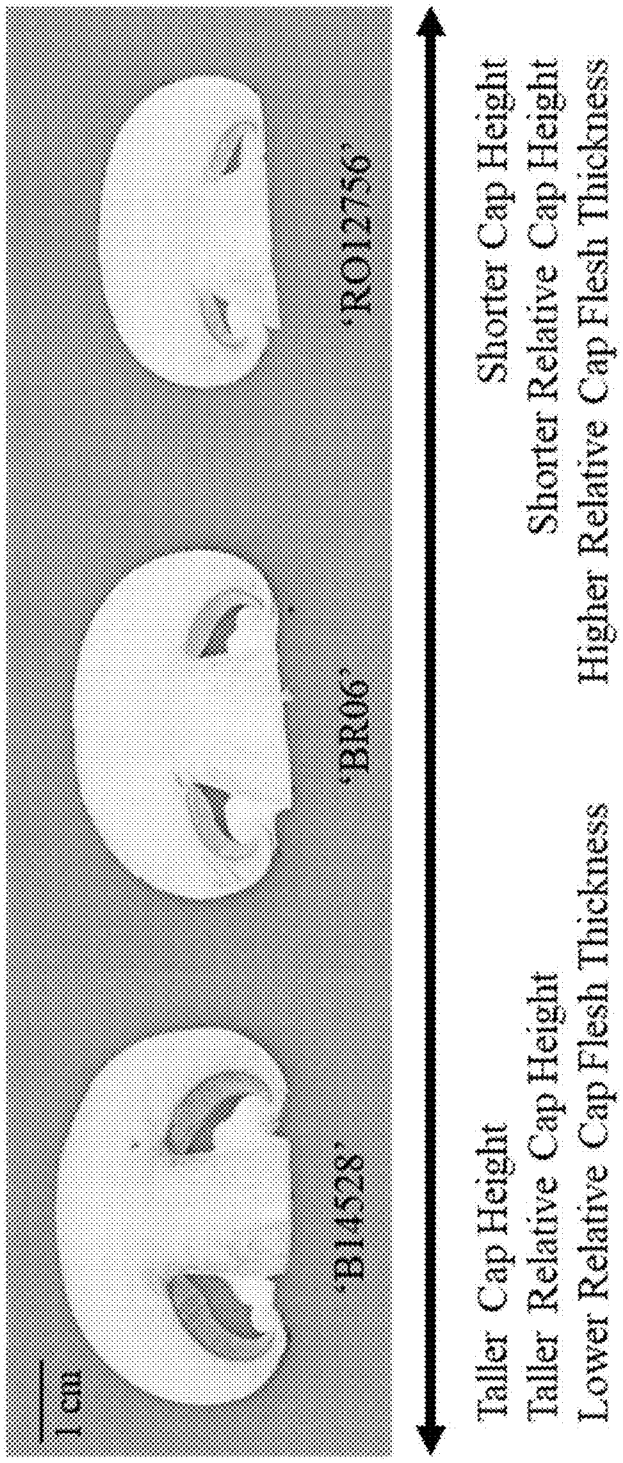
FIG. 5 shows representative comparisons of cap height, relative cap height, and relative cap flesh thickness for variety 'B14528' (left), variety 'BR06' (center), and variety 'RO12756' (right) at first break. Mushrooms pictured were grown in the same room, under the same environmental conditions, and were harvested from the same trial in May 2025. All photos have the same scale. Scale bar=1 cm.

In addition to the comparisons made below, FIGS. 1 and FIGS. 4-5 visually compare variety 'RO12756' to other varieties in tray coverage (FIG. 1), cap color (FIG. 4), and qualities regarding cap height and cap flesh thickness (FIG. 5).

Table 24A below provides qualitative comparisons between mushroom strain 'RO12756' and strain 'BR06'. Column 1 lists the tray-level or trial-level characteristic (as described in Table 1), column 2 shows the qualitative descriptor for the characteristic for mushroom strain 'RO12756' relative to 'BR06', and column 3 shows the qualitative descriptor for mushroom strain 'BR06' relative to 'RO12756'.

TABLE 24A

| Characteristic | 'RO12756' | 'BR06' |
|---|---|---|
| Before First Break | | |
| Days to Pinset | Faster | Slower |
| First Break | | |
| Days to 1st Break | Faster | Slower |
| Tray Coverage | Higher | Lower |
| Cap Color Darkness | Lighter | Darker |
| Cap Firmness | Softer | Firmer |
| Cap Roundness (Visual) | Flatter | Rounder |
| Percent Harvested Speed | Similar | Similar |
| Yield (lb/ft$^2$) | Similar | Similar |
| Second Break | | |
| Days to 2nd Break | Faster | Slower |
| Tray Coverage | Similar | Similar |
| Cap Color Darkness | Lighter | Darker |
| Cap Firmness | Softer | Firmer |
| Cap Roundness (Visual) | Flatter | Rounder |
| Percent Harvested Speed | Higher | Lower |
| Yield (lb/ft$^2$) | Similar | Similar |
| Third Break | | |
| Percent Harvested Speed | Higher | Lower |
| Yield (lb/ft$^2$) | Higher | Lower |
| All Breaks Combined | | |
| Yield (lb/ft$^2$) | Higher | Lower |

Table 24B below provides initial quantitative comparisons between mushroom strain 'RO12756' and strain 'BR06'. Column 1 lists the tray-level or trial-level characteristics (as described in Table 1), column 2 shows the average value of the characteristic for mushroom strain 'RO12756', column 3 shows the standard deviation of the characteristic for mushroom strain 'RO12756', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate $p<0.05$.

TABLE 24B

| | 'RO12756' | | 'BR06' | | |
|---|---|---|---|---|---|
| Characteristic | Average | St. Dev. | Average | St. Dev. | p-value |
| Before First Break | | | | | |
| Days to Pinset | 11.722 | 0.999 | 12.316 | 0.880 | **4.139E−05** |
| First Break | | | | | |
| Days to 1st Break | 17.317 | 0.752 | 17.598 | 0.735 | **1.153E−02** |
| Tray Coverage | 4.178 | 0.799 | 3.935 | 0.866 | **2.900E−02** |
| Cap Color Darkness | 2.916 | 0.601 | 3.872 | 0.380 | **6.840E−35** |
| Cap Firmness | 3.543 | 0.519 | 4.154 | 0.425 | **4.790E−19** |
| Cap Roundness (Visual) | 2.848 | 0.387 | 2.984 | 0.127 | **2.930E−04** |
| Percent Harvested Speed | 24.105% | 23.663 | 16.868% | 19.090 | 1.241E−01 |
| Yield (lb/ft$^2$) | 2.483 | 0.701 | 2.523 | 1.017 | 6.860E−01 |
| Second Break | | | | | |
| Days to 2nd Break | 24.824 | 0.800 | 25.274 | 0.675 | **1.122E−04** |
| Tray Coverage | 4.000 | 0.611 | 4.150 | 0.605 | 6.140E−02 |
| Cap Color Darkness | 3.009 | 0.427 | 3.859 | 0.349 | **9.160E−45** |
| Cap Firmness | 3.509 | 0.553 | 3.969 | 0.435 | **9.200E−12** |
| Cap Roundness (Visual) | 2.634 | 0.484 | 2.992 | 0.154 | **1.030E−13** |
| Percent Harvested Speed | 42.447% | 25.152 | 25.151% | 23.811 | **1.431E−03** |
| Yield (lb/ft$^2$) | 1.606 | 0.537 | 1.601 | 0.617 | 9.340E−01 |
| Third Break | | | | | |
| Percent Harvested Speed | 63.200% | 26.702 | 34.306% | 32.035 | **2.320E−05** |
| Yield (lb/ft$^2$) | 1.038 | 0.313 | 0.747 | 0.371 | **9.180E−13** |
| All Breaks Combined | | | | | |
| Yield (lb/ft$^2$) | 5.127 | 0.792 | 4.871 | 0.918 | **9.080E−03** |

Table 25A below provides qualitative comparisons between mushroom strain 'RO12756' and strain 'B14528'. Column 1 lists the tray-level or trial-level characteristic (as described in Table 1), column 2 shows the qualitative descriptor for the characteristic for mushroom strain 'RO12756' relative to 'B14528', and column 3 shows the qualitative descriptor for mushroom strain 'B14528' relative to 'RO12756'.

TABLE 25A

| Characteristic | 'RO12756' | 'B14528' |
|---|---|---|
| Before First Break | | |
| Compost Colonization | Higher | Lower |
| First Break | | |
| Days to 1st Break | Similar | Similar |
| Tray Coverage | Similar | Similar |
| Cap Color Darkness | Lighter | Darker |
| Cap Firmness | Softer | Firmer |
| Cap Roundness (Visual) | Similar | Similar |
| Percent Harvested Speed | Similar | Similar |

TABLE 25A-continued

| Characteristic | 'RO12756' | 'B14528' |
|---|---|---|
| Second Break | | |
| Days to 2nd Break | Similar | Similar |
| Tray Coverage | Higher | Lower |
| Cap Color Darkness | Lighter | Darker |
| Cap Firmness | Softer | Firmer |
| Cap Roundness (Visual) | Similar | Similar |
| Percent Harvested Speed | Similar | Similar |

Table 25B below provides initial quantitative comparisons between mushroom strain 'RO12756' and strain 'B14528'. Column 1 lists the tray-level or trial-level characteristics (as described in Table 1), column 2 shows the average value of the characteristic for mushroom strain 'RO12756', column 3 shows the standard deviation of the characteristic for mushroom strain 'RO12756', column 4 shows the average value of the characteristic for mushroom strain 'B14528', column 5 shows the standard deviation of the characteristic for mushroom strain 'B14528', and column 6 shows the p-values of two-sample, two-sided t-tests. Bolded p-values indicate p<0.05.

TABLE 25B

| | 'RO12756' | | 'B14528' | | |
|---|---|---|---|---|---|
| Characteristic | Average | St. Dev. | Average | St. Dev. | p-value |
| Before First Break | | | | | |
| Compost Colonization | 4.350 | 0.737 | 3.643 | 1.026 | **6.920E−05** |
| First Break | | | | | |
| Days to 1st Break | 17.317 | 0.752 | 17.000 | 0.649 | 8.599E−02 |
| Tray Coverage | 4.178 | 0.799 | 4.000 | 0.471 | 2.630E−01 |
| Cap Color Darkness | 2.916 | 0.601 | 4.000 | 0.272 | **4.050E−16** |
| Cap Firmness | 3.543 | 0.519 | 3.786 | 0.418 | **2.400E−02** |
| Cap Roundness (Visual) | 2.848 | 0.387 | 2.929 | 0.262 | 2.990E−01 |
| Percent Harvested Speed | 24.105% | 23.660 | 19.000% | 11.247 | 4.392E−01 |
| Second Break | | | | | |
| Days to 2nd Break | 24.824 | 0.800 | 24.417 | 0.669 | 9.848E−02 |
| Tray Coverage | 4.000 | 0.611 | 3.250 | 0.550 | **1.150E−06** |
| Cap Color Darkness | 3.009 | 0.427 | 3.929 | 0.378 | **2.670E−19** |
| Cap Firmness | 3.509 | 0.553 | 3.857 | 0.448 | **2.470E−03** |
| Before First Break | | | | | |
| Compost Colonization | 4.350 | 0.737 | 3.643 | 1.026 | **6.920E−05** |
| First Break | | | | | |
| Cap Roundness (Visual) | 2.634 | 0.484 | 2.536 | 0.508 | 3.430E−01 |
| Percent Harvested Speed | 42.447% | 25.152 | 39.000% | 34.438 | 8.380E−01 |

Individual Mushroom-Level Comparisons

In additional evidence of the distinctness and superiority of mushroom strain 'RO12756', provided below is a summary of precise quantitative measurements of individual mushrooms at first and second breaks. These data compare Cap L* Value, Cap a* Value, and Cap b* Values in the International Commission on Illumination (CIELAB) color space, Cap Diameter, Cap Height, Cap Flesh Thickness, Stipe Diameter, Relative Cap Height, Relative Cap Flesh Thickness, and Relative Stipe Diameter (as described in Table 1). Measurements from 390 first break and 100 second break 'RO12756' mushrooms were compared to 400 first break and 120 second break 'BR06' mushrooms (Tables 26A and 26B) and 150 first break and 80 second break 'B14528' mushrooms (Tables 27A and 27B).

Table 26A below provides qualitative comparisons between mushroom strain 'RO12756' and strain 'BR06'. Column 1 lists the mushroom-level characteristics (as described in Table 1), column 2 shows the qualitative descriptor for the characteristic for mushroom strain 'RO12756' relative to 'BR06', and column 3 shows the qualitative descriptor for mushroom strain 'BR06' relative to 'RO12756'.

TABLE 26A

| Characteristic | 'RO12756' | 'BR06' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Smaller | Larger |
| Cap Height | Shorter | Taller |
| Cap Flesh Thickness | Similar | Similar |
| Stipe Diameter | Smaller | Larger |
| Relative Cap Height | Shorter | Taller |
| Relative Cap Flesh Thickness | Thicker | Thinner |
| Relative Stipe Diameter | Smaller | Larger |

TABLE 26A-continued

| Characteristic | 'RO12756' | 'BR06' |
|---|---|---|
| Second Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Similar | Similar |
| Cap Height | Shorter | Taller |
| Cap Flesh Thickness | Similar | Similar |
| Stipe Diameter | Similar | Similar |
| Relative Cap Height | Shorter | Taller |
| Relative Cap Flesh Thickness | Similar | Similar |
| Relative Stipe Diameter | Similar | Similar |

Table 26B below provides initial quantitative comparisons between mushroom strain 'RO12756' and strain 'BR06'. Column 1 lists the mushroom-level characteristics (as described in Table 1), column 2 shows the average value of the characteristic for mushroom strain 'RO12756', column 3 shows the standard deviation of the characteristic for mushroom strain 'RO12756', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate p<0.05.

TABLE 26B

| | 'RO12756' | | 'BR06' | | |
|---|---|---|---|---|---|
| Characteristic | Average | St. Dev. | Average | St. Dev. | p-value |
| First Break | | | | | |
| Cap L* Value (dark-light) | 74.237 | 3.524 | 64.335 | 5.707 | **5.943E−128** |
| Cap a* Value (green-red) | 3.899 | 1.581 | 7.605 | 1.770 | **1.242E−138** |
| Cap b* Value (blue-yellow) | 24.770 | 2.559 | 28.453 | 2.451 | **3.905E−76** |
| Cap Diameter | 40.571 | 3.829 | 42.200 | 4.005 | **7.566E−09** |
| Cap Height | 24.199 | 1.994 | 25.455 | 2.059 | **1.797E−17** |
| Cap Flesh Thickness | 13.069 | 1.395 | 13.130 | 1.313 | 5.270E−01 |
| Stipe Diameter | 18.258 | 2.139 | 19.546 | 2.585 | **1.130E−13** |
| Relative Cap Height | 0.598 | 0.033 | 0.605 | 0.031 | **3.410E−03** |
| Relative Cap Flesh Thickness | 0.323 | 0.028 | 0.312 | 0.026 | **3.060E−08** |
| Relative Stipe Diameter | 0.451 | 0.040 | 0.464 | 0.054 | **9.166E−05** |
| Second Break | | | | | |
| Cap L* Value (dark-light) | 73.318 | 3.497 | 66.428 | 4.274 | **1.03E−28** |
| Cap a* Value (green-red) | 4.282 | 1.216 | 6.359 | 1.461 | **1.17E−23** |
| Cap b* Value (blue-yellow) | 24.796 | 3.168 | 27.600 | 2.440 | **2.72E−12** |
| Cap Diameter | 42.833 | 5.946 | 43.005 | 4.063 | 8.00E−01 |
| Cap Height | 24.156 | 2.112 | 25.313 | 2.234 | **1.19E−04** |
| Cap Flesh Thickness | 12.359 | 1.048 | 12.526 | 1.163 | 2.71E−01 |
| Stipe Diameter | 16.115 | 1.904 | 15.878 | 2.022 | 3.75E−01 |
| Relative Cap Height | 0.569 | 0.053 | 0.590 | 0.035 | **6.90E−04** |
| Relative Cap Flesh Thickness | 0.293 | 0.040 | 0.292 | 0.025 | 9.06E−01 |
| Relative Stipe Diameter | 0.379 | 0.038 | 0.370 | 0.035 | 5.72E−02 |

Table 27A below provides qualitative comparisons between mushroom strain 'RO12756' and strain 'B14528'. Column 1 lists the mushroom-level characteristics (as described in Table 1), column 2 shows the qualitative descriptor for the characteristic for mushroom strain 'RO12756' relative to 'B14528', and column 3 shows the qualitative descriptor for mushroom strain 'B14528' relative to 'RO12756'.

TABLE 27A

| Characteristic | 'RO12756' | 'B14528' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Smaller | Larger |
| Cap Height | Shorter | Taller |
| Cap Flesh Thickness | Similar | Similar |
| Stipe Diameter | Larger | Smaller |
| Relative Cap Height | Shorter | Taller |
| Relative Cap Flesh Thickness | Thicker | Thinner |
| Relative Stipe Diameter | Larger | Smaller |
| Second Break | | |
| Cap L* Value (dark-light) | Lighter | Darker |
| Cap a* Value (green-red) | Greener | Redder |
| Cap b* Value (blue-yellow) | Bluer | Yellower |
| Cap Diameter | Similar | Similar |
| Cap Height | Shorter | Taller |
| Cap Flesh Thickness | Thicker | Thinner |
| Stipe Diameter | Larger | Smaller |
| Relative Cap Height | Shorter | Taller |
| Relative Cap Flesh Thickness | Similar | Similar |
| Relative Stipe Diameter | Larger | Smaller |

Table 27B below provides quantitative comparisons between mushroom strain 'RO12756' and strain 'B14528'. Column 1 lists the mushroom-level characteristics (as described in Table 1), column 2 shows the average value of the characteristic for mushroom strain 'RO12756', column 3 shows the standard deviation of the characteristic for mushroom strain 'RO12756', column 4 shows the average value of the characteristic for mushroom strain 'B14528', column 5 shows the standard deviation of the characteristic for mushroom strain 'B14528', and column 6 shows the p-values of two-sample, two-sided t-tests. Bolded p-values indicate p<0.05.

TABLE 27B

| Characteristic | 'RO12756' Average | 'RO12756' St. Dev. | 'B14528' Average | 'B14528' St. Dev. | p-value |
|---|---|---|---|---|---|
| First Break | | | | | |
| Cap L* Value (dark-light) | 74.237 | 3.524 | 67.579 | 5.925 | **1.560E−47** |
| Cap a* Value (green-red) | 3.899 | 1.581 | 5.987 | 1.854 | **3.850E−34** |
| Cap b* Value (blue-yellow) | 24.770 | 2.559 | 27.637 | 2.363 | **3.510E−29** |
| Cap Diameter | 40.571 | 3.829 | 43.218 | 3.827 | **6.590E−13** |
| Cap Height | 24.199 | 1.994 | 26.568 | 1.872 | **2.430E−33** |
| Cap Flesh Thickness | 13.069 | 1.395 | 13.057 | 1.012 | 9.210E−01 |
| Stipe Diameter | 18.258 | 2.139 | 17.787 | 2.018 | **1.790E−02** |
| Relative Cap Height | 0.598 | 0.033 | 0.616 | 0.030 | **2.260E−09** |
| Relative Cap Flesh Thickness | 0.323 | 0.028 | 0.303 | 0.024 | **3.050E−14** |
| Relative Stipe Diameter | 0.451 | 0.040 | 0.413 | 0.042 | **1.900E−21** |
| Second Break | | | | | |
| Cap L* Value (dark-light) | 73.318 | 3.497 | 68.288 | 5.217 | **8.20E−13** |
| Cap a* Value (green-red) | 4.282 | 1.216 | 5.256 | 1.241 | **3.51E−07** |
| Cap b* Value (blue-yellow) | 24.796 | 3.168 | 26.285 | 2.185 | **4.48E−04** |
| Cap Diameter | 42.833 | 5.946 | 41.712 | 3.417 | 1.35E−01 |
| Cap Height | 24.156 | 2.112 | 25.062 | 2.039 | **4.14E−03** |
| Cap Flesh Thickness | 12.359 | 1.048 | 11.868 | 1.370 | **7.02E−03** |
| Stipe Diameter | 16.115 | 1.904 | 14.725 | 1.442 | **2.04E−07** |
| Relative Cap Height | 0.569 | 0.053 | 0.602 | 0.033 | **4.09E−06** |
| Relative Cap Flesh Thickness | 0.293 | 0.040 | 0.286 | 0.036 | 2.14E−01 |
| Relative Stipe Diameter | 0.379 | 0.038 | 0.355 | 0.044 | **1.48E−04** |

Additional Trials

Tray-Level Comparisons

Table 28A below provides qualitative comparisons between mushroom strain 'RO12756' and strain 'BR06'. Traits of particular interest are bolded. Column 1 lists the tray-level or trial-level characteristic (as described in Table 1), column 2 shows the qualitative descriptor for the characteristic for mushroom strain 'RO12756' relative to 'BR06', and column 3 shows the qualitative descriptor for mushroom strain 'BR06' relative to 'RO12756'.

TABLE 28A

| Characteristic | 'RO12756' | 'BR06' |
|---|---|---|
| Before First Break | | |
| Days to Pinset | Faster | Slower |
| First Break | | |
| Days to 1st Break | Faster | Slower |
| Percent Harvested Speed | Faster | Slower |
| Yield (kg/$m^2$) | Similar | Similar |
| Second Break | | |
| Days to 2nd Break | Faster | Slower |
| Yield (kg/$m^2$) | Higher | Lower |
| Third Break | | |
| Yield (kg/$m^2$) | Higher | Lower |
| All Breaks Combined | | |
| Yield (kg/$m^2$) | Higher | Lower |

Table 28B below provides quantitative comparisons between mushroom strain 'RO12756' and strain 'BR06'.

The first part of analyzing trait measurements in the additional trials herein included making comparisons between all three of instant strain 'RO12756', comparative strain 'BR06', and comparative strain 'B14528'. For these three strains, a Shapiro-Wilk test and a Levene test were performed first to assess if the data satisfy the assumptions of normality and equal variances among groups, respectively, of a standard ANOVA. The Shapiro-Wilk test and Levene test determined that most of these traits satisfied neither assumption. Therefore, a Kruskal-Wallis test (Kruskal, W. H., & Wallis, W. A. (1952). Use of ranks in one-criterion variance analysis. Journal of the American statistical Association, 47(260), 583-621), a non-parametric variation of ANOVA that does not assume normality, equal variances among groups, or equal sample sizes among groups, was performed. Medians and interquartile ranges (IQR) were reported, as these metrics are robust to non-normal distributions. Means are also reported for consistency with normally-distributed traits.

The Shapiro-Wilk test and Levene test determined that most developmental timing traits (Days to Pinset, Days to 1st Break, and Days to 2nd Break) and yield traits were not normally distributed and variances among groups were not equal. The Kruskal-Wallis test and Dunn post-hoc test ("Dunn's Test"; Dunn, O. J. (1964). Multiple comparisons using rank sums. Technometrics, 6(3), 241-252) were used in these cases. When the Kruskal-Wallis test results were significant based on a threshold of $p<0.05$, Dunn's test was performed post-hoc to make pairwise strain comparisons (Dunn, 1964). P-values were adjusted using the Bonferroni correction to minimize risk of Type 1 error (false significance). An exception to this trend was Percent Harvested Speed, which was normally distributed and exhibited equal variance for all strains. For assessing Percent Harvested Speed, a standard ANOVA was used and a Tukey Honestly Significant Difference (HSD) test was performed post-hoc for pairwise strain comparisons. Standard deviations multiplied by 100 for consistency alongside percentages ("SD*100") were reported for this trait. This testing was performed on groups of three strains, but the results show a pairwise subset of the tests for consistency with the initial trials.

In Table 28B, column 1 shows each trait and the strains compared for said trait, column 2 shows the mean value for that strain's measurements of that trait, column 3 shows the median value of the same measurements, column 4 shows the interquartile range ("IQR") for the same measurements, column 5 shows the number of trials conducted, and column 6 shows the statistical significance group calculated for that strain for that trait according to Dunn's Test. Traits of particular interest are bolded.

TABLE 28B

| Variety | Mean | Median | IQR | Number of Trials | Significance Group (Dunn's Test) |
|---|---|---|---|---|---|
| Before First Break<br>Days to Pinset | | | | | |
| 'RO12756' | 11.4 | 11.0 | 1.00 | 8 | a |
| 'BR06' | 12.6 | 13.0 | 1.00 | 8 | b |
| First Break<br>Days to 1st Break | | | | | |
| 'RO12756' | 17.5 | 17.0 | 1.00 | 8 | a |
| 'BR06' | 18.5 | 18.0 | 1.00 | 8 | b |
| Yield (kg/m$^2$) | | | | | |
| 'RO12756' | 11.91 | 12.40 | 4.88 | 8 | a |
| 'BR06' | 11.96 | 12.69 | 9.52 | 8 | a |
| Second Break<br>Days to 2nd Break | | | | | |
| 'RO12756' | 24.8 | 25.0 | 2.00 | 7 | a |
| 'BR06' | 25.5 | 25.0 | 1.00 | 7 | b |
| Yield (kg/m$^2$) | | | | | |
| 'RO12756' | 8.54 | 8.15 | 2.64 | 8 | a |
| 'BR06' | 7.37 | 5.96 | 4.39 | 8 | b |
| Third Break<br>Yield (kg/m$^2$) | | | | | |
| 'RO12756' | 4.78 | 4.83 | 1.86 | 8 | a |
| 'BR06' | 3.66 | 2.78 | 2.78 | 8 | b |
| All Breaks Combined<br>Yield (kg/m$^2$) | | | | | |
| 'RO12756' | 25.29 | 24.95 | 4.15 | 8 | a |
| 'BR06' | 23.00 | 23.48 | 5.81 | 8 | b |
| Percent Harvested Speed (measured in First Break) | | | SD * 100 | | Significance Group (Tukey HSD) |
| 'RO12756' | 48.2% | 50.9% | 16.30 | 8 | b |
| 'BR06' | 28.6% | 27.4% | 20.90 | 8 | a |

Table 29A below provides qualitative comparisons between mushroom strain 'RO12756' and strain 'B14528'. Traits of particular interest are bolded. Column 1 lists the tray-level or trial-level characteristic (as described in Table 1), column 2 shows the qualitative descriptor for the characteristic for mushroom strain 'RO12756' relative to 'B14528', and column 3 shows the qualitative descriptor for mushroom strain 'B14528' relative to 'RO12756'.

TABLE 29A

| Characteristic | 'RO12756' | 'B14528' |
|---|---|---|
| Before First Break | | |
| Days to Pinset | Similar | Similar |
| First Break | | |
| Days to 1st Break | Similar | Similar |
| Percent Harvested Speed | Similar | Similar |
| Yield (kg/m$^2$) | Similar | Similar |
| Second Break | | |
| Days to 2nd Break | Similar | Similar |
| Yield (kg/m$^2$) | Similar | Similar |

TABLE 29A-continued

| Characteristic | 'RO12756' | 'B14528' |
|---|---|---|
| Third Break | | |
| Yield (kg/m$^2$) | Similar | Similar |
| All Breaks Combined | | |
| Yield (kg/m$^2$) | Similar | Similar |

Table 29B below provides additional quantitative comparison between mushroom strain 'RO12756' and strain 'B14528'. Column 1 shows the strains compared for each trait, column 2 shows the mean value for that strain's measurements, column 3 shows the median value of the same measurements, column 4 shows either the interquartile range ("IQR") or the standard deviation multiplied by 100 for consistency alongside percentages ("SD*100") for the same measurements, column 5 shows the number of trials conducted, and column 6 shows the statistical significance group calculated for that strain for that trait according to either Dunn's Test or Tukey HSD.

TABLE 29B

| Characteristic | Mean | Median | IQR | Number of Trials | Significance Group (Dunn's Test) |
|---|---|---|---|---|---|
| Before First Break<br>Days to Pinset | | | | | |
| 'RO12756' | 11.40 | 11.00 | 1.00 | 8 | a |
| 'B14528' | 11.40 | 11.00 | 1.00 | 8 | a |
| First Break<br>Days to 1st Break | | | | | |
| 'RO12756' | 17.50 | 17.00 | 1.00 | 8 | a |
| 'B14528' | 17.50 | 17.00 | 1.00 | 8 | a |
| Yield (kg/m$^2$) | | | | | |
| 'RO12756' | 11.91 | 12.40 | 4.88 | 8 | a |
| 'B14528' | 12.55 | 12.25 | 5.27 | 8 | a |
| Second Break<br>Days to 2nd Break | | | | | |
| 'RO12756' | 24.80 | 25.00 | 2.00 | 7 | a |
| 'B14528' | 25.00 | 25.00 | 0.50 | 7 | a |
| Yield (kg/m$^2$) | | | | | |
| 'RO12756' | 8.54 | 8.15 | 2.64 | 8 | a |
| 'B14528' | 8.45 | 8.01 | 2.39 | 8 | a |
| Third Break<br>Yield (kg/m$^2$) | | | | | |
| 'RO12756' | 4.78 | 4.83 | 1.86 | 8 | a |
| 'B14528' | 5.52 | 5.57 | 2.88 | 8 | a |
| All Breaks Combined<br>Yield (kg/m$^2$) | | | | | |
| 'RO12756' | 25.29 | 24.95 | 4.15 | 8 | a |
| 'B14528' | 26.51 | 27.10 | 5.76 | 8 | a |
| Percent Harvested Speed (measured in First Break) | Mean | Median | SD * 100 | | Significance Group (Tukey HSD) |
| 'RO12756' | 48.2% | 50.9% | 16.30 | 8 | b |
| 'B14528' | 53.5% | 55.7% | 14.00 | 8 | b |

Individual Mushroom-Level Comparisons

In additional evidence of the distinctness and superiority of mushroom strain 'RO12756', provided below is a summary of precise quantitative measurements of individual mushrooms at first and second breaks. These data compare Cap L* Value, Cap a* Value, and Cap b* Values in the International Commission on Illumination (CIELAB) color space, Cap Apex Flesh Thickness, Cap Edge Flesh Thickness, and Cap Roundness (Calculated) (as described in Table 1). Measurements were taken for hundreds of mushrooms per trait, noted as sample size (n) in Tables 30B and 31B.

Table 30A below provides qualitative comparisons between mushroom strain 'RO12756' and strain 'BR06'. Traits of particular interest are bolded. Column 1 lists the mushroom-level characteristics (as described in Table 1), column 2 shows the qualitative descriptor for the characteristic for mushroom strain 'RO12756' relative to 'BR06', and column 3 shows the qualitative descriptor for mushroom strain 'BR06' relative to 'RO12756'.

TABLE 30A

| Characteristic | 'RO12756' | 'BR06' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |
| Cap Edge Flesh Thickness | Similar | Similar |
| Cap Roundness (Calculated) | Similar | Similar |
| Second Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |
| Cap Edge Flesh Thickness | Thicker | Thinner |
| Cap Roundness (Calculated) | Flatter | Rounder |

Table 30B below provides additional quantitative comparisons between mushroom strain 'RO12756' and strain 'BR06'. Column 1 shows each trait and the strains compared for said trait, column 2 shows the mean value for that strain's measurements of that trait, column 3 shows the median value of the same measurements, column 4 shows the interquartile range ("IQR") for the same measurements, column 5 shows the number of mushrooms assessed (n), and column 6 shows the statistical significance group calculated for that strain for that trait according to Dunn's Test.

TABLE 30B

| Variety | Mean | Median | IQR | Number of Mushrooms (n) | Significance Group (Dunn's Test) |
|---|---|---|---|---|---|
| First Break | | | | | |
| Cap L* Value (dark-light) | | | | | |
| 'RO12756' | 72.12 | 72.29 | 4.81 | 580 | a |
| 'BR06' | 63.30 | 62.74 | 9.83 | 797 | b |
| Cap a* Value (green-red) | | | | | |
| 'RO12756' | 5.62 | 5.66 | 1.88 | 580 | a |
| 'BR06' | 8.67 | 8.96 | 2.58 | 787 | b |
| Cap b* Value (blue-yellow) | | | | | |
| 'RO12756' | 26.98 | 27.06 | 4.11 | 580 | a |
| 'BR06' | 28.72 | 29.04 | 3.17 | 776 | b |
| Cap Apex Flesh Thickness | | | | | |
| 'RO12756' | 0.55 | 0.55 | 0.06 | 575 | a |
| 'BR06' | 0.52 | 0.52 | 0.05 | 541 | b |

TABLE 30B-continued

| Variety | Mean | Median | IQR | Number of Mushrooms (n) | Significance Group (Dunn's Test) |
|---|---|---|---|---|---|
| Cap Edge Flesh Thickness | | | | | |
| 'RO12756' | 0.22 | 0.23 | 0.10 | 569 | a |
| 'BR06' | 0.21 | 0.21 | 0.09 | 537 | a |
| Cap Roundness (Calculated) | | | | | |
| 'RO12756' | 0.61 | 0.61 | 0.04 | 579 | a |
| 'BR06' | 0.61 | 0.61 | 0.04 | 541 | a |
| Second Break | | | | | |
| Cap L* Value (dark-light) | | | | | |
| 'RO12756' | 73.02 | 72.87 | 4.35 | 200 | a |
| 'BR06' | 65.68 | 65.49 | 5.90 | 340 | b |
| Cap a* Value (green-red) | | | | | |
| 'RO12756' | 4.84 | 4.95 | 1.64 | 200 | a |
| 'BR06' | 7.21 | 7.31 | 2.42 | 340 | b |
| Cap b* Value (blue-yellow) | | | | | |
| 'RO12756' | 26.55 | 26.83 | 3.24 | 200 | a |
| 'BR06' | 28.15 | 28.49 | 2.86 | 340 | b |
| Cap Apex Flesh Thickness | | | | | |
| 'RO12756' | 0.54 | 0.54 | 0.04 | 198 | a |
| 'BR06' | 0.51 | 0.52 | 0.07 | 362 | b |
| Cap Edge Flesh Thickness | | | | | |
| 'RO12756' | 0.27 | 0.27 | 0.10 | 199 | a |
| 'BR06' | 0.23 | 0.23 | 0.09 | 362 | b |
| Cap Roundness (Calculated) | | | | | |
| 'RO12756' | 0.56 | 0.56 | 0.05 | 199 | a |
| 'BR06' | 0.60 | 0.59 | 0.06 | 363 | b |

Table 31A below provides qualitative comparisons between mushroom strain 'RO12756' and strain 'B14528'. Column 1 lists the mushroom-level characteristics (as described in Table 1), column 2 shows the qualitative descriptor for the characteristic for mushroom strain 'RO12756' relative to 'B14528', and column 3 shows the qualitative descriptor for mushroom strain 'B14528' relative to 'RO12756'.

TABLE 31A

| Characteristic | 'RO12756' | 'B14528' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |
| Cap Edge Flesh Thickness | Similar | Similar |
| Cap Roundness (Calculated) | Similar | Similar |
| Second Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |
| Cap Edge Flesh Thickness | Thicker | Thinner |
| Cap Roundness (Calculated) | Flatter | Rounder |

Table 31B shows additional quantitative comparisons between mushroom strain 'RO12756' and strain 'B14528'. Column 1 lists the mushroom-level characteristics (as described in Table 1) and each strain, column 2 shows the mean value of the characteristic, column 3 shows the median value of the characteristic, column 4 shows the interquartile range (IQR) for the characteristic, column 5 shows the number of mushrooms assessed (n), and column 6 shows the statistical significance group calculated according to Dunn's Test.

TABLE 31B

| Variety | Mean | Median | IQR | Number of Mushrooms (n) | Significance Group (Dunn's Test) |
|---|---|---|---|---|---|
| First Break | | | | | |
| Cap L* Value (dark-light) | | | | | |
| 'RO12756' | 72.12 | 72.29 | 4.81 | 580 | a |
| 'B14528' | 64.06 | 64.13 | 6.56 | 340 | b |
| Cap a* Value (green-red) | | | | | |
| 'RO12756' | 5.62 | 5.66 | 1.88 | 580 | a |
| 'B14528' | 8.26 | 8.31 | 2.13 | 340 | c |
| Cap b* Value (blue-yellow) | | | | | |
| 'RO12756' | 26.98 | 27.06 | 4.11 | 580 | a |
| 'B14528' | 30.31 | 30.16 | 3.39 | 340 | c |
| Cap Roundness (Calculated) | | | | | |
| 'RO12756' | 0.61 | 0.61 | 0.04 | 579 | a |
| 'B14528' | 0.61 | 0.61 | 0.05 | 389 | a |
| Cap Apex Flesh Thickness | | | | | |
| 'RO12756' | 0.55 | 0.55 | 0.06 | 575 | a |
| 'B14528' | 0.47 | 0.46 | 0.06 | 387 | c |
| Cap Edge Flesh Thickness | | | | | |
| 'RO12756' | 0.22 | 0.23 | 0.10 | 569 | a |
| 'B14528' | 0.22 | 0.22 | 0.08 | 387 | a |

TABLE 31B-continued

| Variety | Mean | Median | IQR | Number of Mushrooms (n) | Significance Group (Dunn's Test) |
|---|---|---|---|---|---|
| Second Break | | | | | |
| Cap L* Value (dark-light) | | | | | |
| 'RO12756' | 73.02 | 72.87 | 4.35 | 200 | a |
| 'B14528' | 68.56 | 69.02 | 6.54 | 170 | c |
| Cap a* Value (green-red) | | | | | |
| 'RO12756' | 4.84 | 4.95 | 1.64 | 200 | a |
| 'B14528' | 6.09 | 5.96 | 2.05 | 170 | c |
| Cap b* Value (blue-yellow) | | | | | |
| 'RO12756' | 26.55 | 26.83 | 3.24 | 200 | a |
| 'B14528' | 27.37 | 27.78 | 3.22 | 170 | c |
| Cap Roundness (Calculated) | | | | | |
| 'RO12756' | 0.56 | 0.56 | 0.05 | 199 | a |
| 'B14528' | 0.60 | 0.60 | 0.05 | 198 | b |
| Cap Apex Flesh Thickness | | | | | |
| 'RO12756' | 0.54 | 0.54 | 0.04 | 198 | a |
| 'B14528' | 0.46 | 0.46 | 0.05 | 198 | c |
| Cap Edge Flesh Thickness | | | | | |
| 'RO12756' | 0.27 | 0.27 | 0.10 | 199 | a |
| 'B14528' | 0.23 | 0.23 | 0.06 | 198 | b |

One of the advantages of the strain 'RO12756' is its incompatibility with other commercial strains. Table 32 below provides results of compatibility tests between strain 'RO12756' and commercial strain 'BR26', commercial strain 'B14528', or related strain 'RO10425'. These results indicate that strain 'RO12756' is incompatible with strain 'BR06', strain 'B14528', and related strain 'RO10425'. This was true regardless of which tested strain served as the compost variety and which tested strain served as the casing variety.

TABLE 32

| Strains (compost variety/ | Mean | | Median | | SD | | | Significance |
|---|---|---|---|---|---|---|---|---|
| casing variety) | lb/ft$^2$ | kg/m$^2$ | lb/ft$^2$ | kg/m$^2$ | lb/ft$^2$ | kg/m$^2$ | Trials | Group |
| RO12756'/'RO12756' | 2.62 | 12.79 | 2.61 | 12.74 | 0.41 | 2.00 | 3 | a |
| RO10425'/'RO10425' | 2.71 | 13.23 | 2.86 | 13.94 | 0.50 | 2.44 | 3 | a |
| BR06'/'BR06' | 2.62 | 12.79 | 2.46 | 11.99 | 1.15 | 5.61 | 2 | a |
| B14528'/'B14528' | 2.93 | 14.31 | 2.92 | 14.23 | 0.34 | 1.66 | 1 | a |
| RO12756'/'BR06', 'BR06'/'RO12756' | 0.70 | 3.42 | 0.62 | 3.03 | 0.25 | 1.22 | 2 | b |
| RO12756'/'B14528', 'B14528'/'RO12756' | 0.68 | 3.32 | 0.60 | 2.91 | 0.43 | 2.10 | 1 | b |
| RO12756'/'RO10425', 'RO10425'/'RO12756' | 0.91 | 4.44 | 1.04 | 5.08 | 0.35 | 1.71 | 1 | b |

Deposit Information

Hybrid mushroom variety 'RO10425'

A deposit of the hybrid mushroom variety 'RO10425' is maintained by Amycel, LLC, having an address of 260 Westgate Drive, Watsonville CA, 95076. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 25 cryopreserved or freeze-dried vials from same harvest (0.5 ml per vial) of the same variety made according to the Budapest Treaty in the American Type Culture Collection, (ATCC), ATCC Patent Depository, 10801 University Boulevard, Manassas, Virginia, 20110, USA.

The hybrid mushroom variety 'RO10425' was deposited on Apr. 18, 2025, according to the Budapest Treaty in the American Type Culture Collection (ATCC), ATCC Patent Depository, 10801 University Boulevard, Manassas, Virginia, 20110, USA. The deposit has been assigned ATCC number PTA-127856. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

Hybrid Mushroom Variety 'RO14176'

A deposit of the hybrid mushroom variety 'RO14176' is maintained by Amycel, LLC, having an address of 260 Westgate Drive, Watsonville CA, 95076. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 25 cryopreserved or freeze-dried vials from same harvest (0.5 ml per vial) of the same variety made according to the Budapest Treaty in the American Type Culture Collection, (ATCC), ATCC Patent Depository, 10801 University Boulevard, Manassas, Virginia, 20110, USA.

The hybrid mushroom variety 'RO14176' was deposited on Feb. 6, 2025, according to the Budapest Treaty in the American Type Culture Collection (ATCC), ATCC Patent Depository, 10801 University Boulevard, Manassas, Virginia, 20110, USA. The deposit has been assigned ATCC number PTA-127855. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

Hybrid Mushroom Variety 'RO12756'

A deposit of the hybrid mushroom variety 'RO12756' is maintained by Amycel, LLC, having an address of 260 Westgate Drive, Watsonville CA, 95076. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 25 cryopreserved or freeze-dried vials from same harvest (0.5 ml per vial) of the same variety made according to the Budapest Treaty in the American Type Culture Collection, (ATCC), ATCC Patent Depository, 10801 University Boulevard, Manassas, Virginia, 20110, USA.

The hybrid mushroom variety 'RO12756' was deposited on Feb. 13, 2025, according to the Budapest Treaty in the American Type Culture Collection (ATCC), ATCC Patent Depository, 10801 University Boulevard, Manassas, Virginia, 20110, USA. The deposit has been assigned ATCC number PTA-127857. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

STATEMENT OF EMBODIMENTS

Embodiment 1. A mushroom variety selected from the group consisting of 'RO10425', 'RO14176', and 'RO12756', representative culture of which having been deposited under ATCC Nos. PTA-127856, PTA-127855, and PTA-127857 respectively.

Embodiment 2. An *Agaricus bisporus* culture designated as *Agaricus bisporus* line 'RO10425', a representative culture of the line having been deposited under ATCC No. PTA-127856.

Embodiment 3. An *Agaricus bisporus* culture designated as *Agaricus bisporus* line 'RO12756', a representative culture of the line having been deposited under ATCC No. PTA-127857.

Embodiment 4. A new and distinct variety of *Agaricus bisporus* Imbach mushroom selected from the group consisting of 'RO10425', 'RO14176', and 'RO12756', as shown and described herein.

Embodiment 5. A new and distinct variety of *Agaricus bisporus* Imbach mushroom named 'RO10425', as illustrated and described.

Embodiment 6. A method of producing a hybrid mushroom culture of *Agaricus bisporus*, the method comprising the steps of:

(a) providing a first homokaryon selected from a wild strain, designated AA-0096, or a progeny thereof, wherein said wild strain AA-0096 is available from ATCC under Accession No. PTA-6903;

(b) providing a second homokaryon selected from a commercial off-white hybrid strain, which is compatible with first homokaryon;
(c) crossing the first homokaryon with the second homokaryon to form a first culture of intermediate hybrid homokaryons;
(d) backcrossing the first culture to the second homokaryon to form a second culture of intermediate hybrid homokaryons; and
(e) crossing the second culture to a bridging cross strain to form the hybrid mushroom culture, designated 'RO10425', a culture of which has been deposited under ATCC Accession No. PTA-127856.

Embodiment 7. The method of embodiment 6, wherein the bridging cross strain is '4×29', representative sample of '4×29' being available under ATCC Accession No. PTA-6877.

Embodiment 8. The method of embodiment 6 or 7, wherein the commercial off-white hybrid strain is derived from a U1 mushroom strain.

Embodiment 9. The method according to embodiments 6-8, further including the steps of producing at least one hybrid mushroom, said steps comprising:
(f) inoculating a mushroom growth medium with the hybrid mushroom culture;
(g) maintaining said inoculated growth medium under conditions conducive to mushroom fruiting; and
(h) collecting at least one hybrid mushroom from said growth medium.

Embodiment 10. A hybrid *Agaricus bisporus* mushroom strain designated 'RO10425', a culture of which having been deposited under ATCC Accession No. PTA-127856.

Embodiment 11. A hybrid *Agaricus bisporus* mushroom strain, wherein the hybrid strain is a cross of a parental hybrid *Agaricus bisporus* mushroom strain with an *Agaricus bisporus* bridging cross strain, wherein the parental hybrid strain is derived from wild strain AA-0096 and a commercial off-white hybrid strain, and wherein a representative culture of said wild strain AA-0096 is available from ATCC under Accession No. PTA-6903.

Embodiment 12. The hybrid mushroom strain of embodiment 11, wherein the commercial off-white hybrid strain is derived from a U1 mushroom strain.

Embodiment 13. A hybrid mushroom strain designated 'RO10425', representative culture of which having been deposited under ATCC Accession No. PTA-127856, wherein cells from the hybrid mushroom culture have at least one marker presented herein.

Embodiment 14. A hybrid mushroom produced by the method of embodiment 9 or the hybrid mushroom strain of any one of embodiments 10-13, wherein said hybrid mushroom has at least one physical characteristic selected from the group consisting of darker cap color, higher yield, and thicker cap as compared to the corresponding physical characteristics of 'BR06', 'BR06' having representative sample accessible under ATCC under Accession No. PTA-6876.

Embodiment 15. A mushroom part from the hybrid mushroom produced by the method of embodiment 9 or 14, or produced by the hybrid mushroom strain of any one of embodiments 10-14.

Embodiment 16. The mushroom part of embodiment 15, wherein the mushroom part is a fruiting body, cap, stipe, basidium, spore, mycelium, mixed or unmixed spawn, inoculated substrate, or product produced from the mushroom.

Embodiment 17. A new and distinct variety of *Agaricus bisporus* Imbach mushroom named 'RO12756', as illustrated and described.

Embodiment 18. A method of producing a hybrid mushroom culture of *Agaricus bisporus*, the method comprising the steps of:
(a) providing a first homokaryon selected from a hybrid mushroom strain designated 'RO10425', or a progeny thereof, representative sample of 'RO10425' having been deposited under ATCC under Accession No. PTA-127856;
(b) providing a second homokaryon selected from the cross of a bridging cross strain and a commercial off-white hybrid strain, which is compatible with first homokaryon; and
(c) crossing the first homokaryon with the second homokaryon to form the hybrid mushroom culture, designated 'RO12756', a culture of which has been deposited under ATCC Accession No. PTA-127857.

Embodiment 19. The method of embodiment 18, wherein the bridging cross strain is '4×29', representative sample of '4×29' being available under ATCC Accession No. PTA-6877.

Embodiment 20. The method of embodiment 18 or 19, wherein the commercial off-white hybrid is distinct from the hybrid mushroom strain 'RO10425'.

Embodiment 21. The method of any one of embodiments 18-20, wherein the commercial off-white hybrid strain is derived from a U1 mushroom strain.

Embodiment 22. The method according to embodiments 18-21, further including the steps of producing at least one hybrid mushroom, said steps comprising:
(d) inoculating a mushroom growth medium with the hybrid mushroom culture;
(e) maintaining said inoculated growth medium under conditions conducive to mushroom fruiting; and
(f) collecting at least one hybrid mushroom from said growth medium.

Embodiment 23. A hybrid *Agaricus bisporus* mushroom strain designated 'RO12756', a culture of which having been deposited under ATCC Accession No. PTA-127857.

Embodiment 24. A hybrid *Agaricus bisporus* mushroom strain, wherein the hybrid strain is a cross of a parental hybrid *Agaricus bisporus* mushroom strain with hybrid mushroom strain designated 'RO10425', wherein the parental hybrid strain is a cross of a bridging cross strain to a commercial off-white hybrid strain, and wherein a representative culture of said strain 'RO10425' is available from ATCC under Accession No. PTA-127856.

Embodiment 25. A hybrid *Agaricus bisporus* mushroom strain, wherein the hybrid strain is a cross of a parental hybrid *Agaricus bisporus* mushroom strain with hybrid mushroom strain designated 'RO10425', wherein the parental hybrid strain is derived from a U1 type off-white hybrid, and wherein a representative culture of said strain 'RO10425' is available from ATCC under Accession No. PTA-127856.

Embodiment 26. The hybrid mushroom strain of embodiment 25, wherein the commercial off-white hybrid strain is derived from a U1 mushroom strain.

Embodiment 27. A hybrid mushroom strain designated 'RO12756', representative sample of which having been deposited under ATCC Accession No. PTA-127857, wherein cells from the hybrid mushroom strain have at least one marker presented herein.

Embodiment 28. A hybrid mushroom produced by the method of embodiment 22 or produced by the hybrid mushroom strain of any one of embodiments 23-27, wherein said hybrid mushroom has at least one physical characteristic selected from the group consisting of light brown cap color as exhibited by a higher L* (lighter) value, lower a* (greener) value, and lower b* (bluer) value;

as high or higher tray coverage;

softer cap firmness;

shorter cap height relative to cap diameter;

as thick or thicker cap flesh relative to cap diameter; and as thick or thicker stipes relative to cap diameter when compared to the corresponding physical characteristics of 'B14528', 'B14528' having representative sample accessible under NRRL Accession No. 50900.

Embodiment 29. A hybrid mushroom produced by the method of embodiment 22 or produced by the hybrid mushroom strain of any one of embodiments 23-27, wherein said hybrid mushroom has at least one physical characteristic selected from the group consisting of faster speed to reach pinset and harvestable maturity;

as high or higher tray coverage;

as high or higher percent of 2nd break yield harvested by 24 after casing;

as high or higher 3rd break yield by 32 days after casing;

higher overall 3rd break yield;

higher overall yield across all breaks;

light brown cap color exhibited by a higher L* (lighter) value, lower a* (greener) value, and lower b* (bluer) value;

softer cap firmness;

shorter cap height relative to cap diameter:

as thick or thicker cap flesh relative to cap diameter; and as thick or thicker stipes relative to cap diameter when compared to the corresponding physical characteristics of 'BR06', 'BR06' having representative sample accessible under ATCC under Accession No. PTA-6876.

Embodiment 30. A mushroom or part of a mushroom grown from the hybrid mushroom of embodiment 28 or embodiment 29.

Embodiment 31. The mushroom part of embodiment 30, wherein the mushroom part is a fruiting body, cap, stipe, basidium, spore, mycelium, mixed or unmixed spawn, inoculated substrate, or product produced from the mushroom.

Embodiment 32. Use of a spore, protoplast, heterokaryon of 'RO14176', or homokaryon of 'RO10425' or 'RO12756', said use comprising isolation of the spore, protoplast, heterokaryon, or homokaryon by any method disclosed herein, representative sample of 'RO10425' having been deposited under ATCC Accession No. PTA-127856;

representative sample of 'RO14176' having been deposited under ATCC Accession No. PTA-127855; and representative sample of 'RO12756' having been deposited under ATCC Accession No. PTA-127857.

Embodiment 33. A new and distinct variety of *Agaricus bisporus* Imbach mushroom named 'RO14176', as illustrated and described.

Embodiment 34. A method of producing a heterokaryotic hybrid mushroom culture of *Agaricus bisporus*, the method comprising the steps of:

(a) providing a first homokaryon selected from a wild strain, designated AA-0096, or a progeny thereof, wherein said wild strain AA-0096 is available from ATCC under Accession No. PTA-6903;

(b) providing a second homokaryon selected from a commercial off-white hybrid strain, which is compatible with first homokaryon;

(c) crossing the first homokaryon with the second homokaryon to form a first culture of intermediate hybrid homokaryons;

(d) backcrossing the first culture to the second homokaryon to form a second culture of intermediate hybrid homokaryons;

(e) crossing the second culture to a bridging cross strain to form a hybrid mushroom culture, designated 'RO10425', a culture of which has been deposited under ATCC Accession No. PTA-127856;

(f) allowing the hybrid mushroom culture, designated 'RO10425', to undergo plasmogamy; and (g) selecting a heterokaryotic single spore isolate from the result of the plasmogamy, said heterokaryotic single spore isolate designated 'RO14176', thereby producing the heterokaryotic hybrid mushroom culture.

Embodiment 35. The method of embodiment 34, wherein the bridging cross strain is '4×29', representative sample of '4×29' being available under ATCC Accession No. PTA-6877.

Embodiment 36. The method of embodiment 34 or 35, wherein the commercial off-white hybrid strain is derived from a U1 mushroom strain.

Embodiment 37. The method according to embodiments 34-36, further including the steps of producing at least one hybrid mushroom, said steps comprising:

(h) inoculating a mushroom growth medium with the hybrid mushroom culture;

(i) maintaining said inoculated growth medium under conditions conducive to mushroom fruiting; and (j) collecting at least one heterokaryotic hybrid mushroom from said growth medium.

Embodiment 38. A hybrid *Agaricus bisporus* mushroom strain designated 'RO14176', a culture of which having been deposited under ATCC Accession No. PTA-127855.

Embodiment 39. A hybrid mushroom strain designated 'RO14176', representative culture of which having been deposited under ATCC Accession No. PTA-127855, wherein cells from the hybrid mushroom culture have at least one marker presented herein.

Embodiment 40. A hybrid mushroom produced by the method of embodiment 37 or the hybrid mushroom strain of any one of embodiments 38-39, wherein said hybrid mushroom has at least one physical characteristic selected from the group consisting of faster timing to reach pinset and harvestable maturity, higher tray coverage, softer cap firmness, different cap color, higher yield, taller cap, and thicker cap flesh, as compared to the corresponding physical characteristics of 'BR06', 'BR06' having representative sample accessible under ATCC under Accession No. PTA-6876.

Embodiment 41. A mushroom part from the hybrid mushroom produced by the method of embodiment 37 or produced by the hybrid mushroom strain of any one of embodiments 38-39.

Embodiment 42. The mushroom part of embodiment 41, wherein the mushroom part is a fruiting body, cap, stipe, basidium, spore, mycelium, mixed or unmixed spawn, inoculated substrate, or product produced from the mushroom.

Embodiment 43. A method of producing a hybrid mushroom culture of *Agaricus bisporus*, the method comprising the steps of:

(a) providing a homokaryon selected from a hybrid mushroom strain designated 'RO10425', or a progeny thereof, representative sample of 'RO10425' having been deposited under ATCC Accession No. PTA-127856;

(b) producing at least one heterokaryotic single spore isolate (SSI) from the homokaryon;

(c) selecting, from among the at least one SSI, a desirable single spore isolate; and (d) producing the hybrid mushroom culture from the selected single spore isolate, wherein the hybrid mushroom culture is designated 'RO14176', representative sample of 'RO14176' having been deposited under ATCC Accession No. PTA-127855.

Embodiment 44. The method according to embodiment 43, further including the steps of producing at least one hybrid mushroom, said steps comprising:

(e) inoculating a mushroom growth medium with the hybrid mushroom culture;

(f) maintaining said inoculated growth medium under conditions conducive to mushroom fruiting; and (g) collecting at least one hybrid mushroom from said growth medium.

Embodiment 45. A hybrid mushroom produced by the method of embodiment 34 or produced by the hybrid mushroom strain of any one of embodiments 38-39, wherein said hybrid mushroom has at least one physical characteristic selected from the group consisting of faster timing to reach second break, higher tray coverage, different cap color, larger stipe diameter, taller cap, and thicker cap flesh when compared to the corresponding physical characteristics of 'B14528', 'B14528' having representative sample accessible under NRRL Accession No. 50900.

Embodiment 46. A mushroom or part of a mushroom grown from the hybrid mushroom of embodiment 40 or embodiment 45.

Embodiment 47. The mushroom part of embodiment 46, wherein the mushroom part is a fruiting body, cap, stipe, basidium, spore, mycelium, mixed or unmixed spawn, inoculated substrate, or product produced from the mushroom.

What is claimed is:

1. A hybrid *Agaricus bisporus* mushroom strain designated as 'RO14176', a representative culture of which having been deposited under ATCC No. PTA-127855.

2. A mushroom of the hybrid *Agaricus bisporus* mushroom strain of claim 1.

3. A mushroom part from the mushroom of claim 2.

4. The mushroom part of claim 3, wherein the mushroom part is a fruiting body, cap, stipe, basidium, spore, mycelium, mixed or unmixed spawn, inoculated substrate, protoplast, gill, cell, or product produced from the mushroom.

5. The mushroom of claim 2, wherein the mushroom has at least one physical characteristic selected from the group consisting of:

lighter cap color as exhibited by a higher L* (lighter) value, lower a* (greener) value, and lower b* (bluer) value;

higher yield;

rounder cap;

faster time to pinset, first break, and/or second break;

thicker cap flesh as exhibited by thicker cap apex flesh and thicker cap edge flesh; and faster percent harvested speed, when compared to the corresponding physical characteristics of 'BR06', 'BR06' having a representative sample accessible under ATCC under Accession No. PTA-6876.

6. The mushroom of claim 2, wherein the mushroom has at least one physical characteristic selected from the group consisting of:

light brown cap color as exhibited by a higher L* (lighter) value, lower a* (greener) value, and lower b* (bluer) value;

as high or higher tray coverage;

thicker cap flesh as exhibited by thicker cap apex flesh and thicker cap edge flesh; and rounder cap, when compared to the corresponding physical characteristics of 'B14528', 'B14528' having representative sample accessible under NRRL Accession No. 50900.

* * * * *